US007642250B2

(12) United States Patent
Williams

(10) Patent No.: US 7,642,250 B2
(45) Date of Patent: Jan. 5, 2010

(54) N-BENZYL SUBSTITUTED PYRIDYL PORPHYRIN COMPOUNDS AND METHODS OF USE THEREOF

(75) Inventor: William Williams, Ipswich, MA (US)

(73) Assignee: Inotek Pharmaceuticals Corporation, Beverly, MA (US)

( * ) Notice: Subject to any disclaimer, the term of this patent is extended or adjusted under 35 U.S.C. 154(b) by 321 days.

(21) Appl. No.: 11/528,082

(22) Filed: Sep. 26, 2006

(65) Prior Publication Data
US 2007/0072825 A1     Mar. 29, 2007

Related U.S. Application Data

(60) Provisional application No. 60/721,388, filed on Sep. 28, 2005.

(51) Int. Cl.
*A61K 38/02*     (2006.01)
(52) U.S. Cl. ....................................... 514/185; 540/145
(58) Field of Classification Search ................... 540/145
See application file for complete search history.

(56) References Cited

U.S. PATENT DOCUMENTS

| 6,573,258 | B2 | 6/2003 | Bommer et al. |
| 6,730,666 | B1 | 5/2004 | Yayon et al. |
| 6,916,799 | B2 | 7/2005 | Fridovich et al. |
| 2006/0003982 | A1 | 1/2006 | Williams et al. |
| 2008/0009473 | A1 | 1/2008 | Williams et al. |
| 2008/0021007 | A1 | 1/2008 | Batinic-Haberle et al. |
| 2008/0085883 | A1 | 4/2008 | Piganelli et al. |
| 2008/0113956 | A1 | 5/2008 | Fridovich et al. |

FOREIGN PATENT DOCUMENTS

| WO | WO-96/40223 A1 | 12/1996 |
| WO | WO-98/33503 A1 | 8/1998 |
| WO | WO-00/75144 A2 | 12/2000 |
| WO | WO-08/045358 A1 | 4/2008 |

OTHER PUBLICATIONS

International Search Report and Written Opinion issued for International Patent Application No. PCT/US2006/037742.

*Primary Examiner*—James O Wilson
*Assistant Examiner*—Brian McDowell
(74) *Attorney, Agent, or Firm*—Lahive & Cockfield, LLP; Jane E. Remillard; Brian C. Trinque

(57) ABSTRACT

The present invention relates to N-Benzyl-Substituted Pyridyl Porphyrin Compounds and compositions comprising an effective amount of N-Benzyl-Substituted Pyridyl Porphyrin Compounds. The N-Benzyl-Substituted Pyridyl Porphyrin Compounds include compounds of the following formula:

Formula (A)

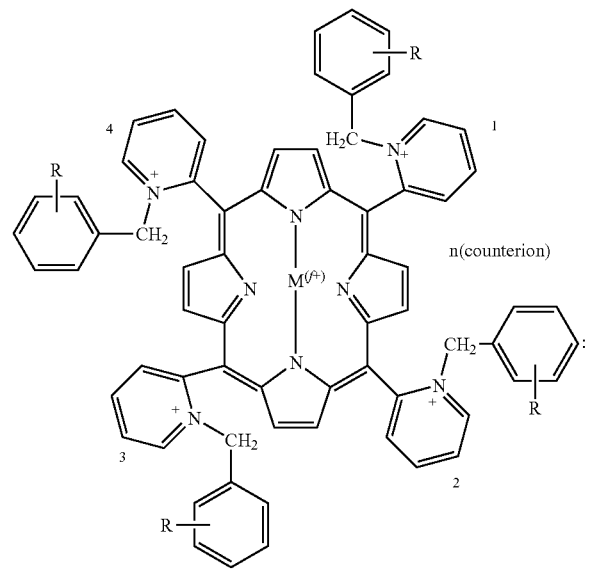

wherein:
M is Fe or Mn;
f is 0 or 1;
each R is independently —C(O)(amino acid residue) or —SO$_2$(amino acid residue); and
n is the number of counterions sufficient to balance the charges of the compound of Formula (A).

22 Claims, 12 Drawing Sheets

N-BENZYL SUBSTITUTED PYRIDYL PORPHYRIN COMPOUNDS AND METHODS OF USE THEREOF

This application claims the benefit of U.S. Provisional Application No. 60/721,388, filed Sep. 28, 2005, the entire disclosure of which is incorporated by reference herein.

1. FIELD OF THE INVENTION

The present invention relates to N-Benzyl-Substituted Pyridyl Porphyrin Compounds, compositions comprising an effective amount of an N-Benzyl-Substituted Pyridyl Porphyrin Compound and methods for treating or preventing injury due to exposure to a reactive species, erectile dysfunction, urinary incontinence, lung disease, hyperoxia, neurodegenerative disease, liver disease, myocardial damage during cardioplegia, an inflammatory condition, a reperfusion injury, an ischemic condition, a cardiovascular disease, diabetes, a diabetic complication, cancer, a side effect of cancer chemotherapy, or a radiation-induced injury, and methods for prolonging the half-life of an oxidation-prone compound, comprising administering to a subject in need thereof an effective amount of an N-Benzyl-Substituted Pyridyl Porphyrin Compound.

2. BACKGROUND OF THE INVENTION

Oxidants are normal by-products of cell metabolism. However, reactive oxygen species such as superoxide ("$O_2^-$") and reactive intermediates formed from $O_2^-$ are known to damage biological targets. For example, J. Lee et al., *J. Am. Chem. Soc.* 120:7493-7501 (1998) discloses that reactive oxygen and nitrogen species play a role in the regulation and inhibition of mitochondrial respiration and apoptosis.

S. Cuzzocrea et al., Pharm. *Rev.*, 53:135-159 (2001) discloses that biologically relevant free-radicals derived from oxygen include $O_2^-$, perhydroxyl radical ("$HO_2^-$"), and nitric oxide ("NO"). One source of $O_2^-$ is a proinflammatory cytokine, which produces $O_2^-$ during reperfusion following ischemia. This reference discloses that reaction of NO with $O_2^-$ forms the reactive peroxynitrite ion ("$ONOO^-$") according to the reaction:

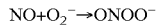

The reference further discloses that formation of ONOO— enhances the cytotoxic potential of NO and $O_2^-$.

In animals, a superoxide dismutase ("SOD") counters the effects of these reactive species. SODs are metalloenzymes that catalyze the conversion of $O_2^-$ to hydrogen peroxide and oxygen according to the reaction:

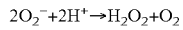

It is reported that certain synthetic metallomacrocyles also catalyze the transformation of reactive species into less reactive products. U.S. Pat. No. 6,204,259 to Riley et al. discloses that a pentazamacrocycle comprising a Mn(II) or Mn(III) metal can catalyze the conversion of $O_2^-$ into oxygen and hydrogen peroxide.

Spasojevic et al., *Biology and Chemistry* 4(5):526-533 (2000) discloses that tetrakis-5,10,15,20-(2-N-ethylpyridinium)porphyrinato complexes of manganese(II) and manganese(III) are catalytic scavengers of oxygen.

J. Lee et al., *J. Am. Chem. Soc.* 120:7493-7501 (1998) discloses that $O_2^-$ and $ONOO^-$ are decomposed by the metalloporphyrin 5,10,15,20-tetrakis(N-methyl-4-pyridyl)porphinatoiron(III).

Lee et al., *Bioorg. Med. Chem. Letters* 7:2913-2918 (1997) discloses that 5,10,15,20-tetrakis(N-methyl-4-pyridinium) porphinatomanganese(III) catalyzes the reduction of $ONOO^-$ in the presence of biological antioxidants such as vitamin C, gluthionate, and vitamin E.

U.S. Pat. No. 5,630,137 to Nguyen et al. discloses a cosmetic composition containing SODs in combination with metalloporphyrins. The composition is allegedly useful to treat skin and hair disorders caused by free radicals. This patent discloses the use of naturally occurring metalloporphyrins such as chlorophyll, chlorophyllin and hemoglobin to allegedly reinforce the anti-free-radical action of the SOD.

German Patent Publication No. DE 19647640 A1 discloses a metalloporphyrin dimer in which two metalloporphyrin compounds are covalently joined at the meso position of the porphyrin rings. The patent publication alleges that the dimer is useful for catalyzing oxygen-transfer processes.

International Publication No. WO 99/55388 discloses meso-substituted metalloporphyrin complexes in which the meso substituents are ester, alkyl, alkyl halide, and amide groups. This publication further alleges that such compounds are useful for modulating the cellular levels of oxidants and the processes in which these oxidants participate.

Metalloporphyrins are also reported to inhibit telomerase activity by binding to quadraplex DNA. For example, Shi et al., *J. Med. Chem.* 44:4509-4523 (2002) discloses that cationic forms of meso-tetrakis(N-methylpyridinium)metalloporphyrins interact with the quadraplex structure of DNA.

U.S. Pat. No. 6,087,493 to Wheelhouse et al. discloses meso-tetrakis(pyridyl)metalloporphyrins in which the nitrogen atom of the pyridyl rings are substituted with a hydrogen, alkyl, alkylhydroxy, alkylamine, alkylacetate or alkylsulfate group. This patent alleges that such compounds are useful as telomerase inhibitors.

U.S. Pat. No. 6,204,259 to Riley et al. discloses that pentazamacrocycles comprising a Mn(II) or Mn(III) metal are allegedly useful for treating inflammatory disease states and reperfusion injury.

U.S. Pat. No. 6,127,356 to Crapo et al. discloses meso-substituted metalloporphyrins in which the meso substituents are aryl, substituted aryl, cycloalkyl, 4-pyridyl or N-substituted 4-pyridyl groups. This patent further discloses meso-tetrakis(pyridinium)metalloporphyrins in which the nitrogen atom of the pyridyl ring is substituted with an alkyl group, alkylhydroxy, alkylamine, alkylcarboxylate, alkysulfate or alkylphosphate. The patent alleges that the disclosed metalloporphyrins act as mimetics of SODs.

Misko et al., *J. Biol. Chem.* 273:15646-15653 (1998) discloses that 5,10,15,20-tetrakis(N-methyl-4-pyridinium)porphinatoiron(III) catalyzes the conversion of $ONOO^-$ into nitrate. The authors also disclose that 5,10,15,20-tetrakis(N-methyl-4-pyridinium)porphinatoiron(III) is allegedly useful for reducing cellular damage at sites of inflammation.

International Publication No. WO 00/75144 A2 discloses 5,10,15,20-tetrakis(N-alkylpyridinum)metalloporphyrins in which its pyridyl moieties are joined to the meso carbon atoms of the porphyrin ring at the 2("ortho"), 3("meta") or 4("para") position of the pyridyl ring relative to the nitrogen atom. The publication alleges that the meso-tetrakis(N-alkylpyridinium)metalloporphyrins are useful for treating inflammation diseases including arthritis, inflammatory bowel disease and acute respiratory disease syndrome, and for the treatment of ischemia-reperfusion injury.

U.S. Pat. No. 5,994,339 to Crapo et al. discloses Mn—, Fe— and Cu-based 5,10,15,20-tetrakis(N-alkyl-4-pyridinium)metalloporphyrins in which the nitrogen atom of the pyridyl ring is substituted with an alkyl, alkylhydroxy, alkylamine, alkylcarboxylate, alkylsulfate or alkyphosphate group. This patent also alleges that 5,10,15,20-tetrakis(N-alkyl-4-pyridinium)metalloporphyrins are useful as mimetics of SODs and for the treatment of an inflammatory condition.

U.S. Pat. No. 6,245,758 B1 to Stern et al. discloses the use of 5,10,15,20-tetrakis(pyridyl)metalloporphyrins, and their corresponding N-alkylpyridinium salts, to allegedly treat disorders including inflammation disease and ischemic reperfusion. Metals allegedly useful in the metalloporphyrins include Mn, Fe, Ni and V.

U.S. Patent Application Publication 2002/0042407 to Fridovich et al. discloses that 5,10,15,20-tetrakis(N-alkylpyridinium)metalloporphyrins are allegedly useful for modulating the intracellular or extracellular levels of oxidants such as $O_2^-$. Metals that are allegedly useful in the metalloporphyrins include Fe, Mn, Co, Ni and Zn. The publication also discloses methods for using these 5,10,15,20-tetrakis(N-alkylpyridinium)metalloporphyrins to allegedly treat disorders such as inflammatory diseases of the skin and lungs, ischemia reperfusion injury; eye disorders such as glaucoma, macular degeneration and cataracts; and diseases of the central nervous system.

There remains, however, a clear need for new compounds, compositions and methods for that are useful for treating or preventing injury due to exposure to a reactive species, erectile dysfunction, urinary incontinence, lung disease, hyperoxia, neurodegenerative disease, liver disease, myocardial damage during cardioplegia, an inflammatory condition, a reperfusion injury, an ischemic condition, a cardiovascular disease, diabetes, a diabetic complication, cancer, a side-effect of cancer chemotherapy, or a radiation-induced injury, or for prolonging the half-life of an oxidation-prone compound.

Citation of any reference in Section 2 of this application is not an admission that the reference is prior art to this application.

3. SUMMARY OF THE INVENTION

The present invention relates to compounds having the Formula (A):

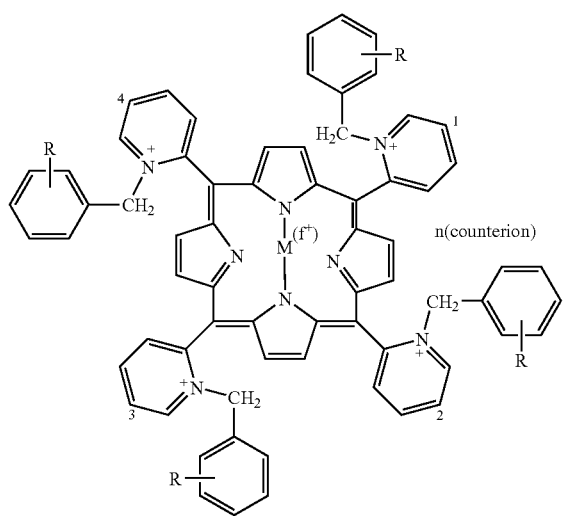

Formula (A)

n(counterion)

wherein:
  M is Fe or Mn;
  f is 0 or 1;
  each R is independently —C(O)(amino acid residue) or —SO$_2$(amino acid residue); and
  n is the number of counterions sufficient to balance the charges of the compound of Formula (A).

A compound of Formula (A) (an "N-Benzyl-Substituted Pyridyl Porphyrin Compound") is useful for treating or preventing injury due to exposure to a reactive species, erectile dysfunction, urinary incontinence, lung disease, hyperoxia, neurodegenerative disease, liver disease, myocardial damage during cardioplegia, an inflammatory condition, a reperfusion injury, an ischemic condition, a cardiovascular disease, diabetes, a diabetic complication, cancer, a side effect of cancer chemotherapy, or a radiation-induced injury (each being a "Condition"), or for prolonging the half-life of an oxidation-prone compound, in a subject.

The invention also relates to compositions comprising an effective amount of an N-Benzyl-Substituted Pyridyl Porphyrin Compound, and a physiologically acceptable carrier or vehicle. The compositions are useful for treating or preventing a Condition or for prolonging the half-life of an oxidation-prone compound in a subject.

The invention further relates to methods for treating or preventing a Condition, comprising administering to a subject in need thereof an effective amount of an N-Benzyl-Substituted Pyridyl Porphyrin Compound.

The invention further relates to methods for prolonging the half-life of an oxidation-prone compound, comprising administering to a subject in need thereof an effective amount of an N-Benzyl-Substituted Pyridyl Porphyrin Compound.

The present invention may be understood more fully by reference to the following detailed description, figures, and illustrative examples, which are intended to exemplify non-limiting embodiments of the invention.

4. BRIEF DESCRIPTION OF THE FIGURES

FIG. 1 shows the effect of Compounds 163, 165, 162, 161, 166, 167, and 134, respectively, on cell viability of murine RAW cells exposed to 2 mM H$_2$O$_2$ ("H2O2").

FIG. 2 shows the effect of Compounds 105, 103, 122 isomer 1, 122 isomer 2, 122 isomer 3, 101, and 102, respectively, on cell viability of murine RAW cells exposed to 2 mM H2O2.

Figure 1:
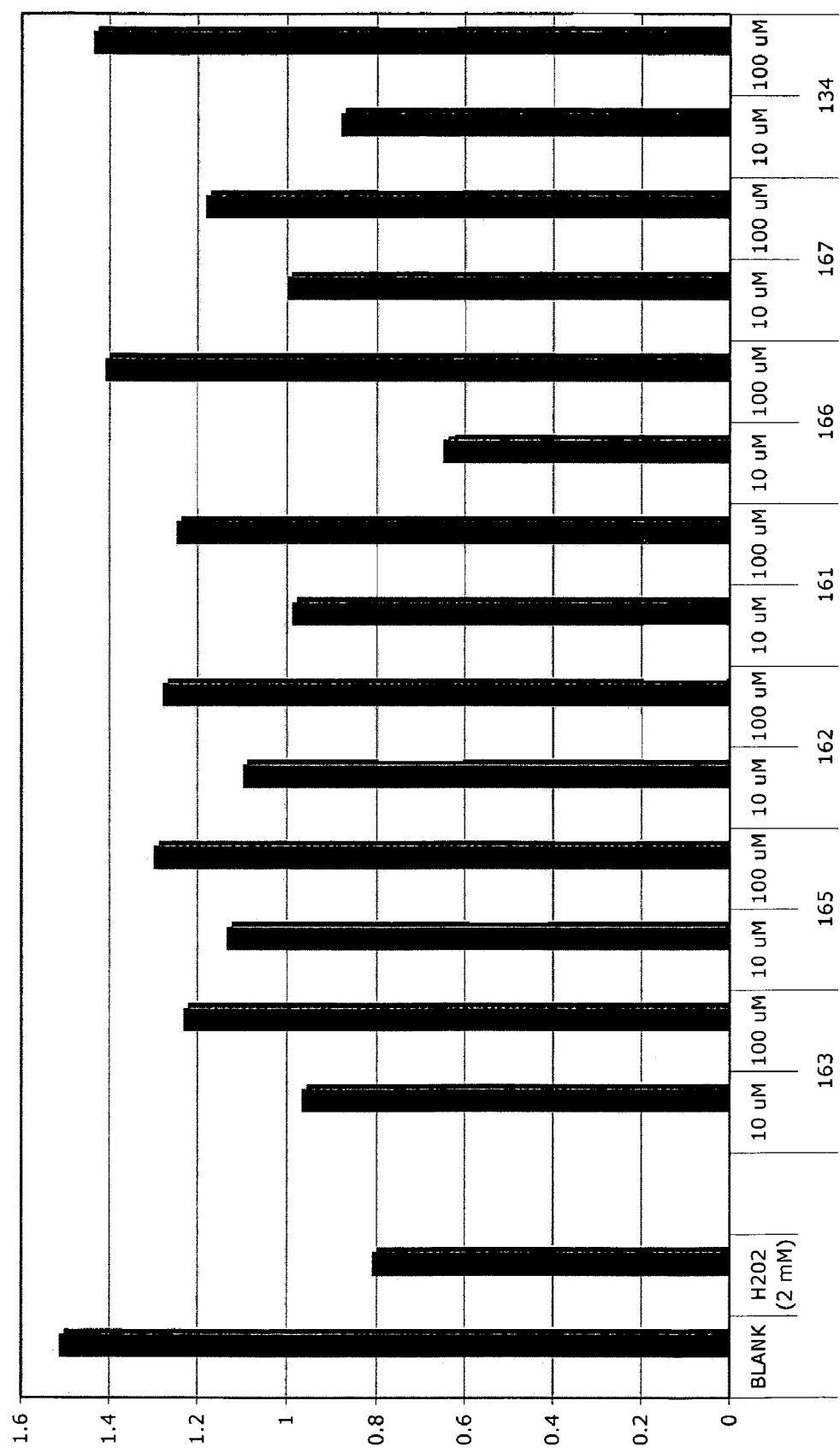
Figure 2:
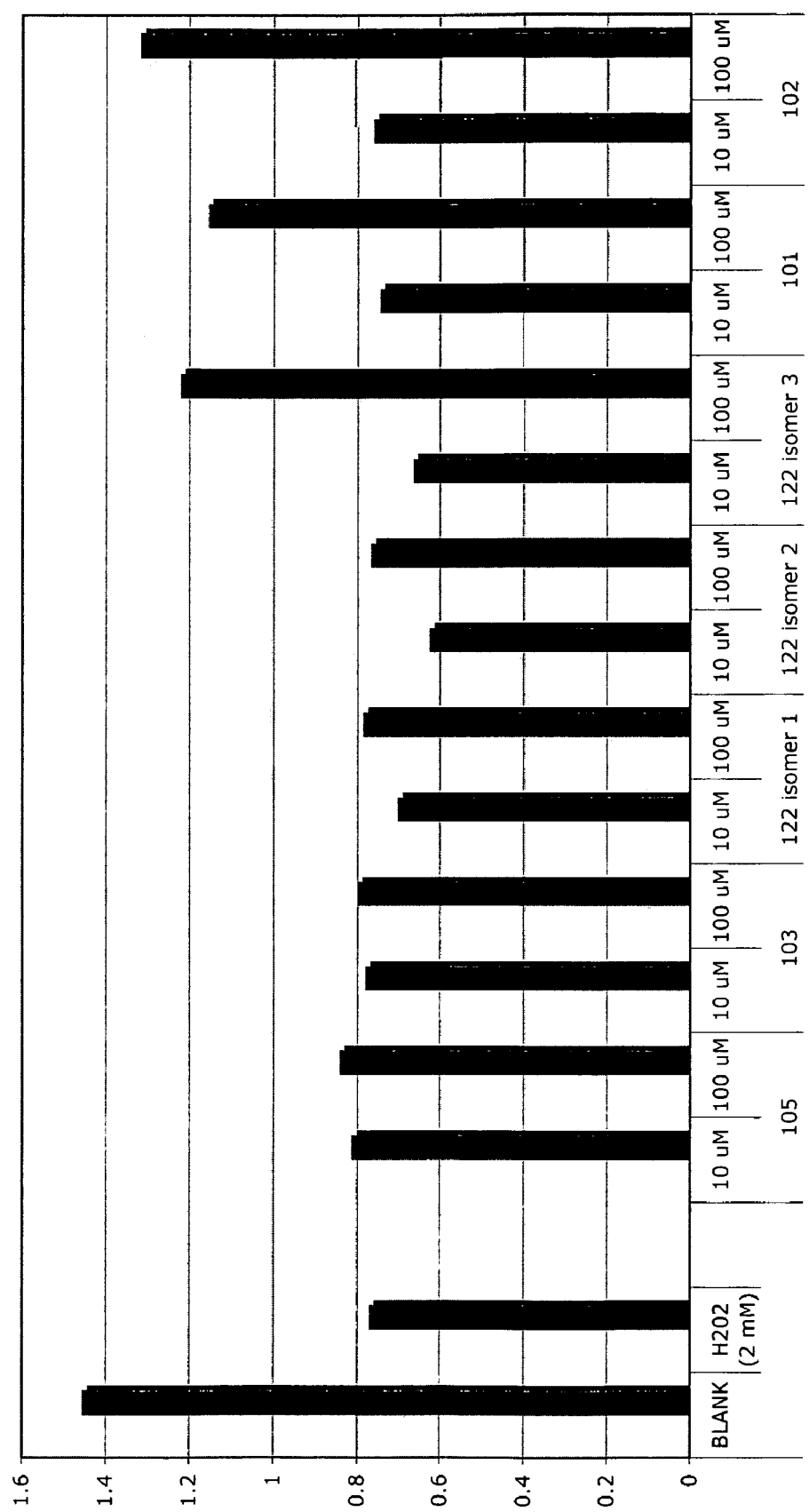
Figure 3:
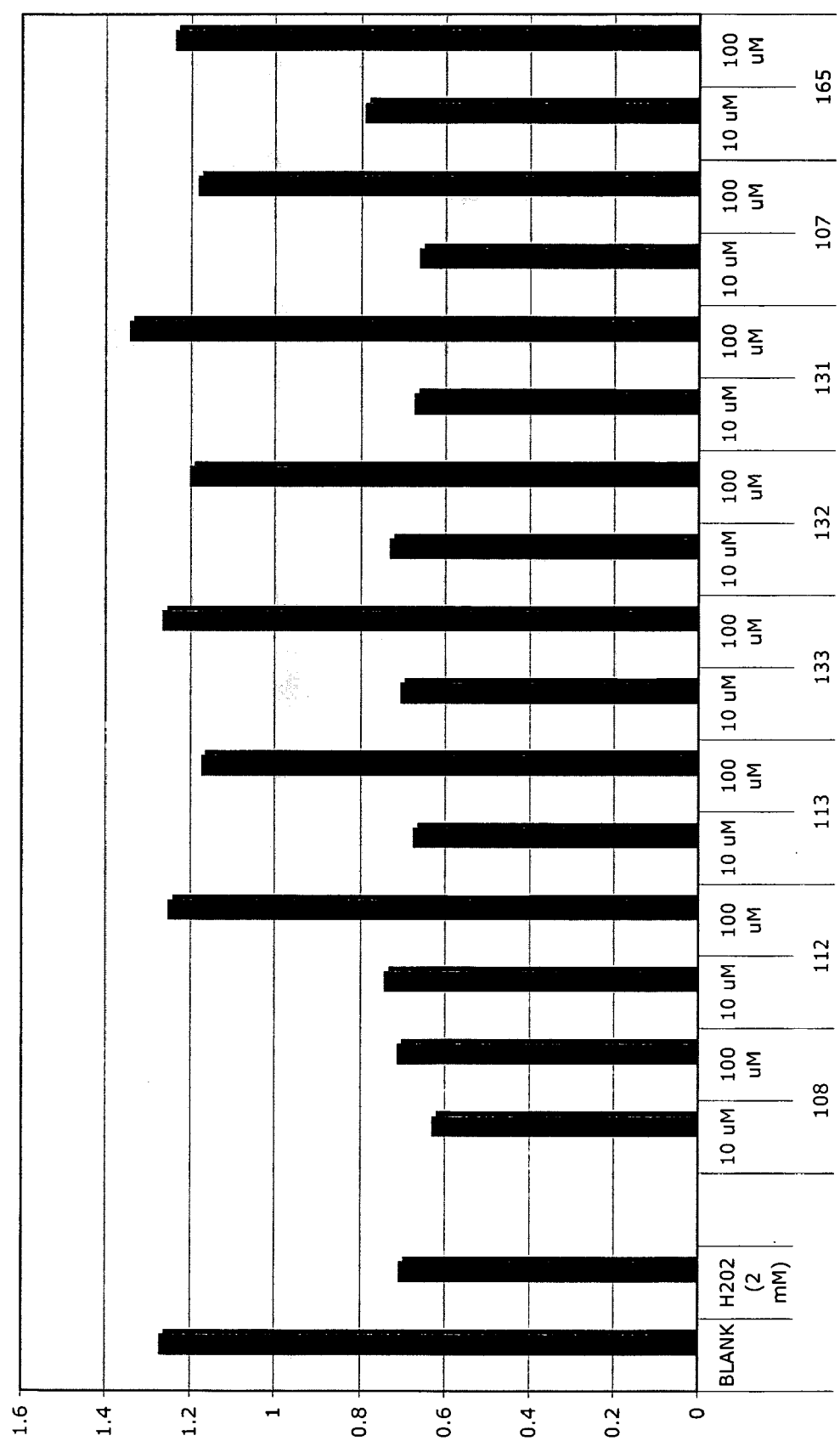
FIG. 3 shows the effect of Compounds 108, 112, 113, 133, 132, 131, 107, and 165, respectively, on cell viability of murine RAW cells exposed to 2 mM H2O2.
Figure 4:
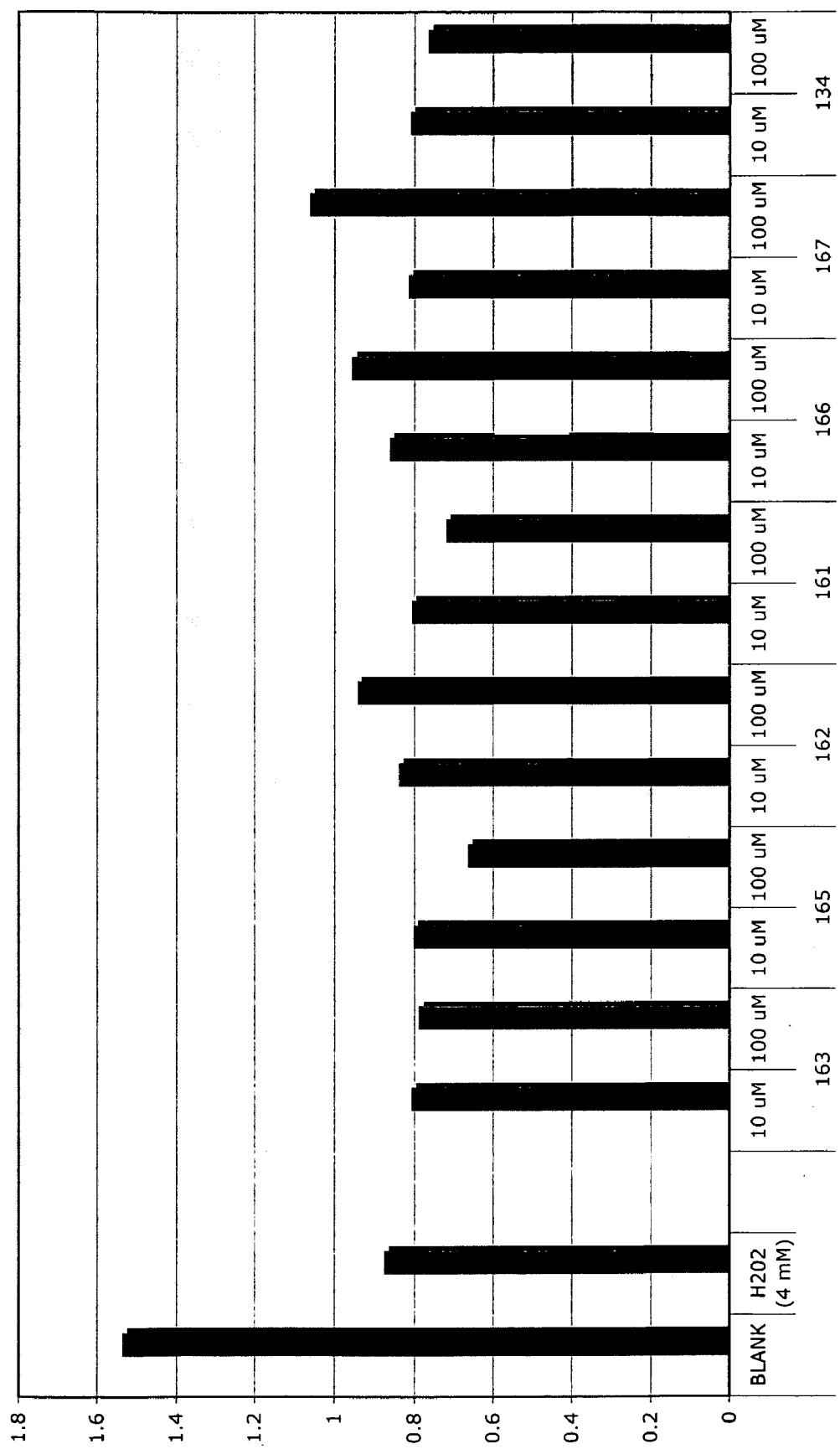
FIG. 4 shows the effect of Compounds 163, 165, 162, 161, 166, 167, and 134, respectively, on cell viability of murine RAW cells exposed to 4 mM H2O2.
Figure 5:
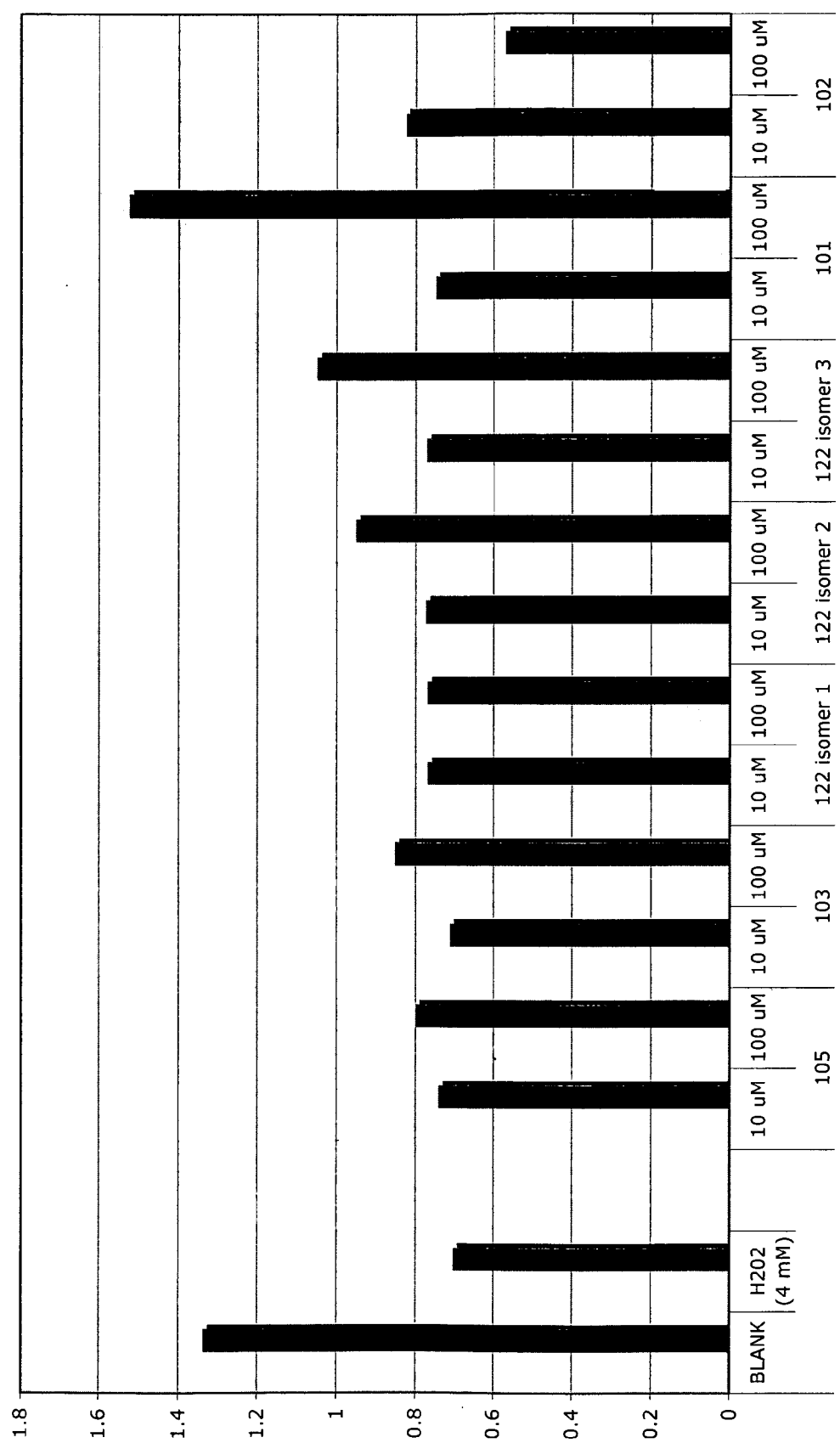

FIG. 5 shows the effect of Compounds 105, 103, 122 isomer 1, 122 isomer 2, 122 isomer 3, 101, and 102, respectively, on cell viability of murine RAW cells exposed to 4 mM H2O2.

Figure 6:
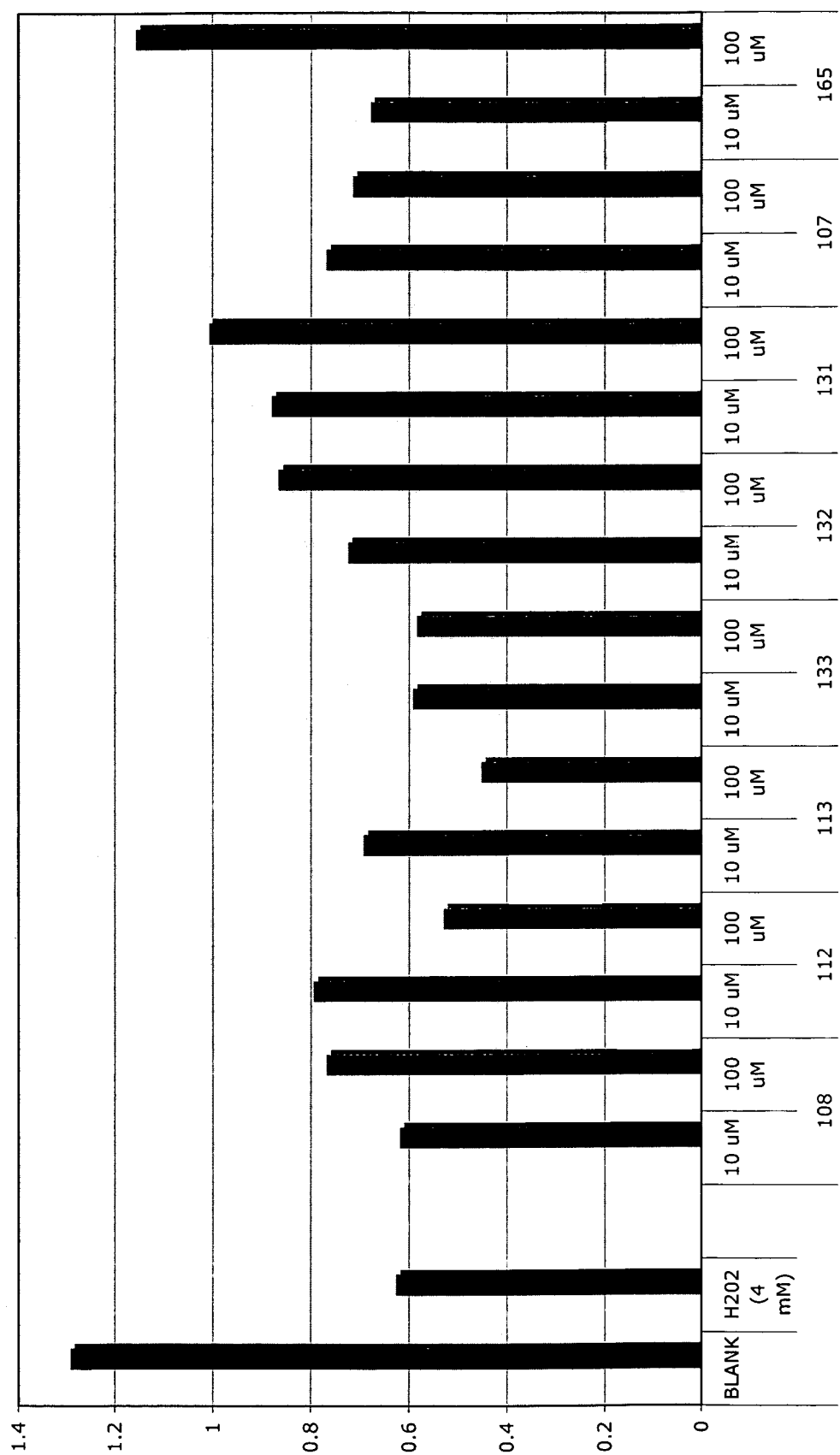

FIG. 6 shows the effect of Compounds 108, 112, 113, 133, 132, 131, 107, and 165, respectively, on cell viability of murine RAW cells exposed to 4 mM H2O2.

Figure 7:
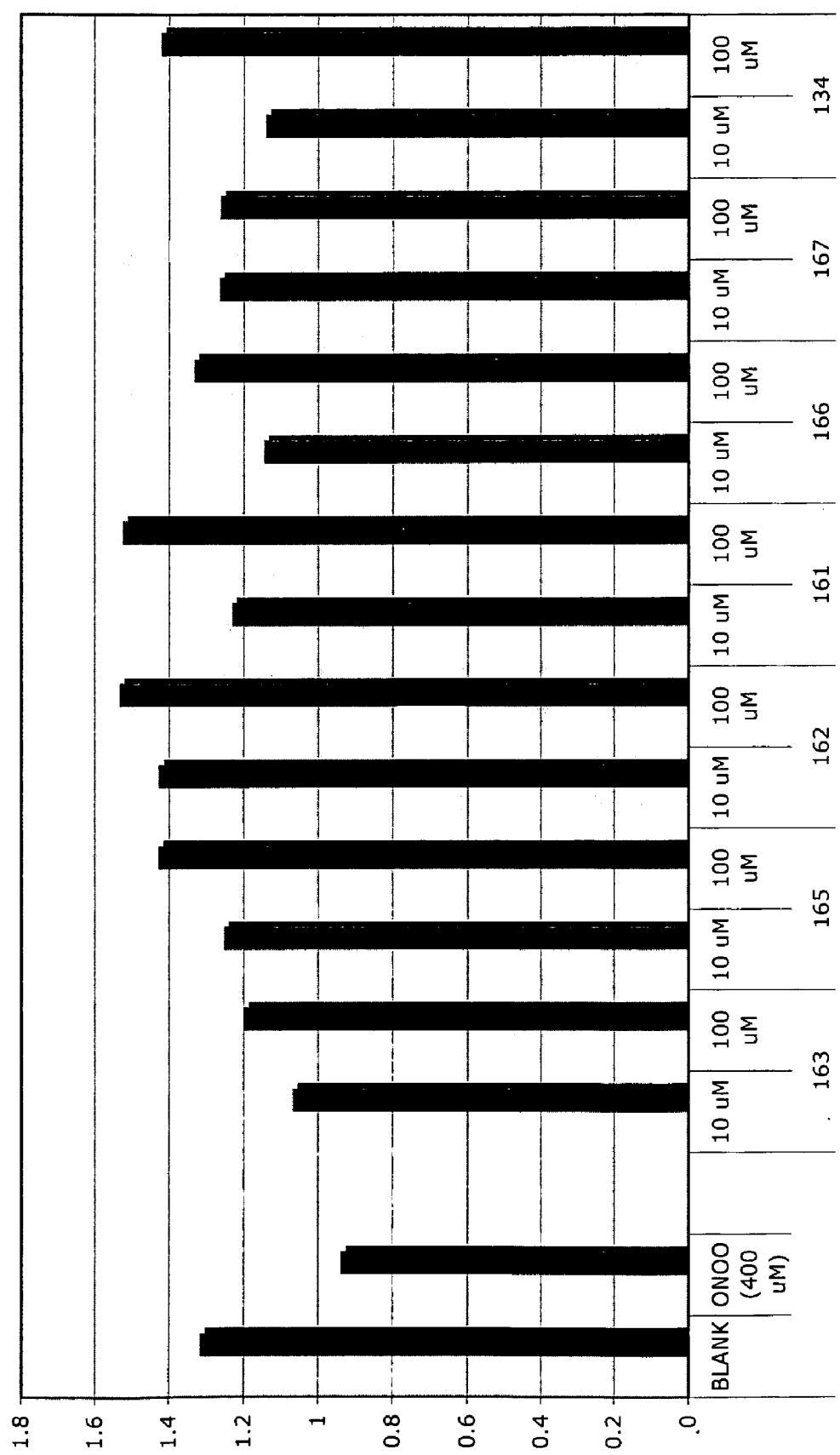

FIG. 7 shows the effect of Compounds 163, 165, 162, 161, 166, 167, and 134, respectively, on cell viability of murine RAW cells exposed to 400 µM ONOO$^-$.

Figure 8:
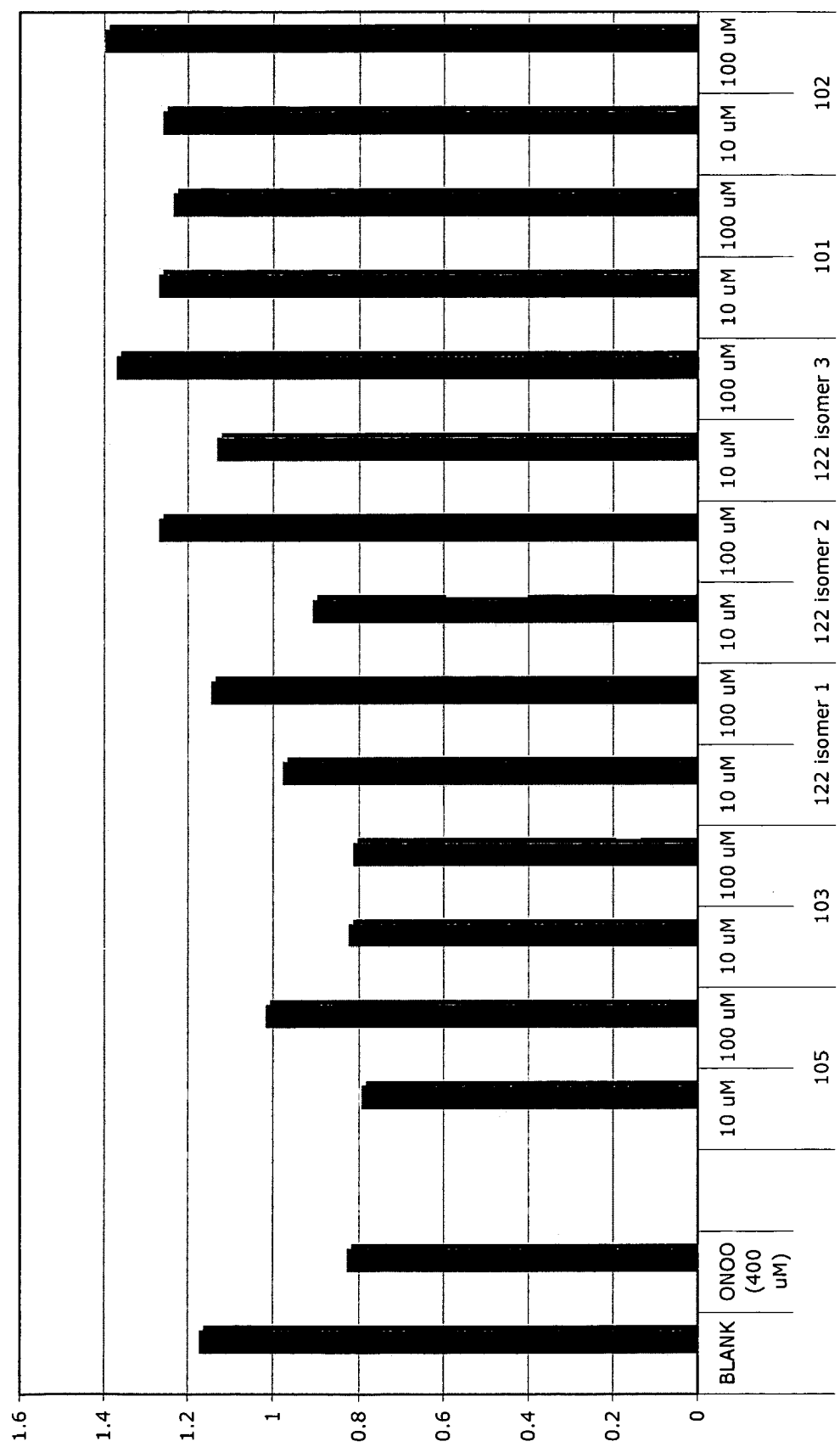

FIG. 8 shows the effect of Compounds 105, 103, 122 isomer 1, 122 isomer 2, 122 isomer 3, 101, and 102, respectively, on cell viability of murine RAW cells exposed to 400 µM ONOO$^-$.

Figure 9:
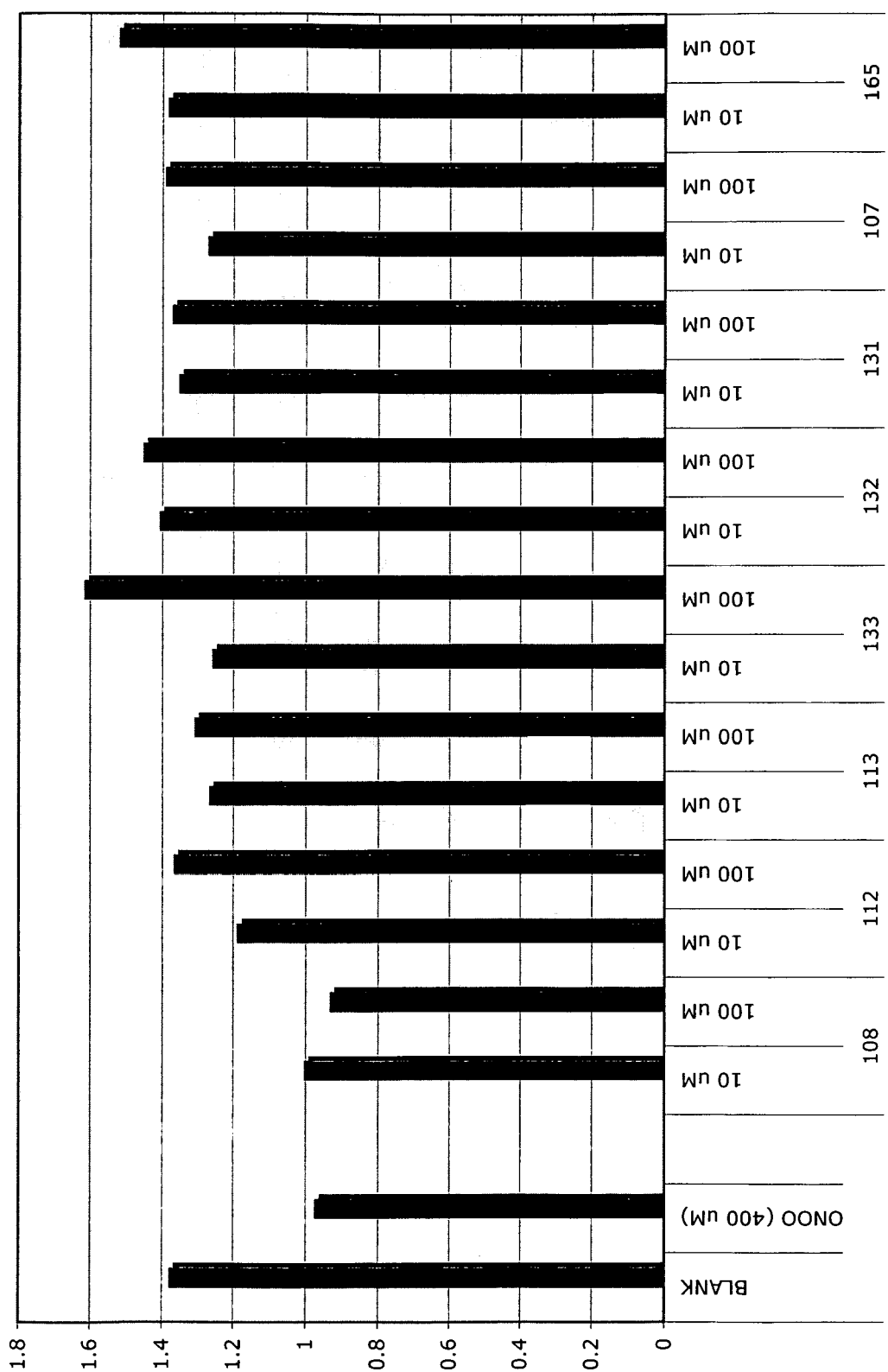

FIG. 9 shows the effect of Compounds 108, 112, 113, 133, 132, 131, 107, and 165, respectively, on cell viability of murine RAW cells exposed to 400 μM ONOO⁻.

Figure 10:
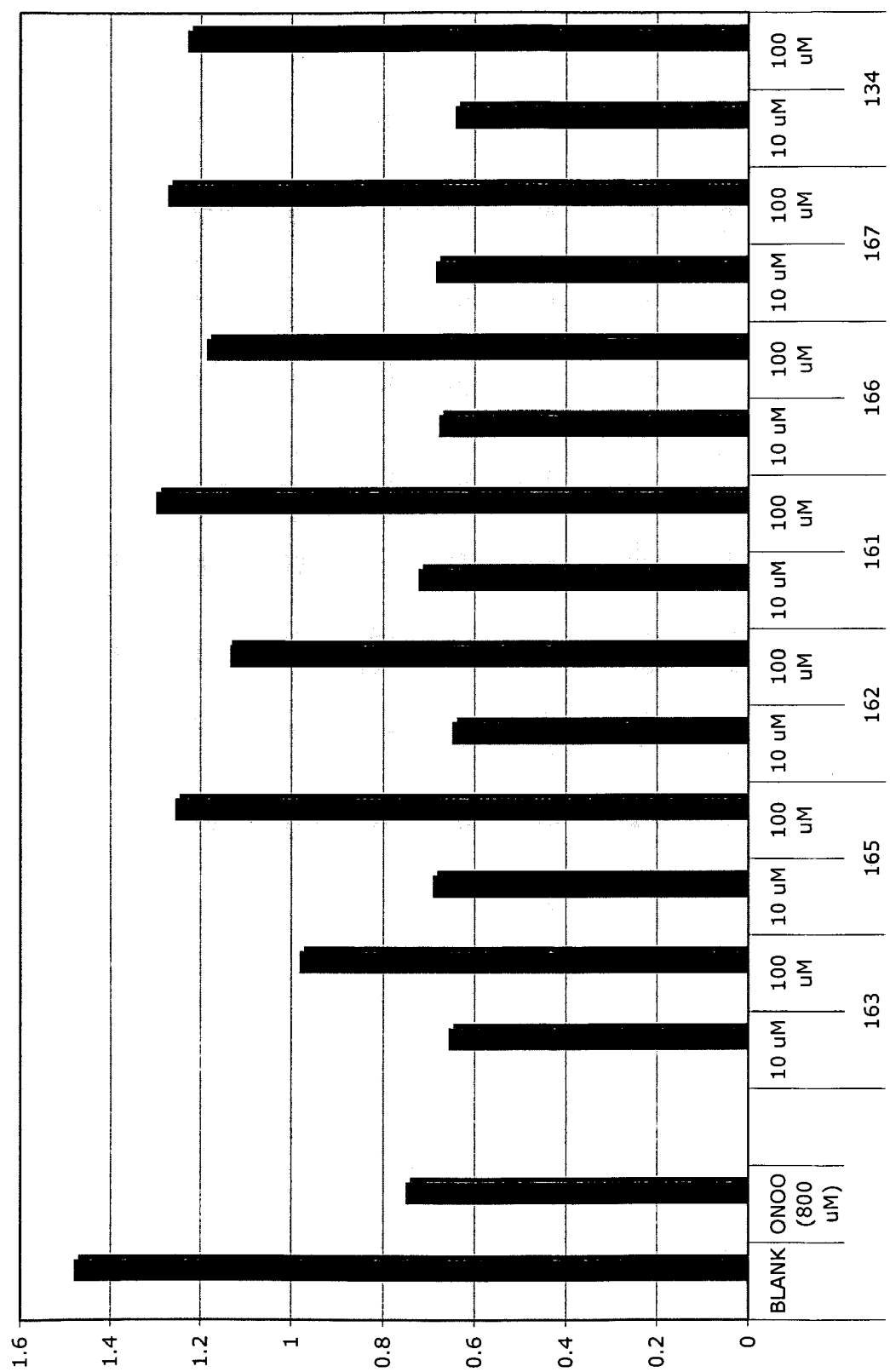

FIG. 10 shows the effect of Compounds 163, 165, 162, 161, 166, 167, and 134, respectively, on cell viability of murine RAW cells exposed to 800 μM ONOO⁻.

Figure 11:
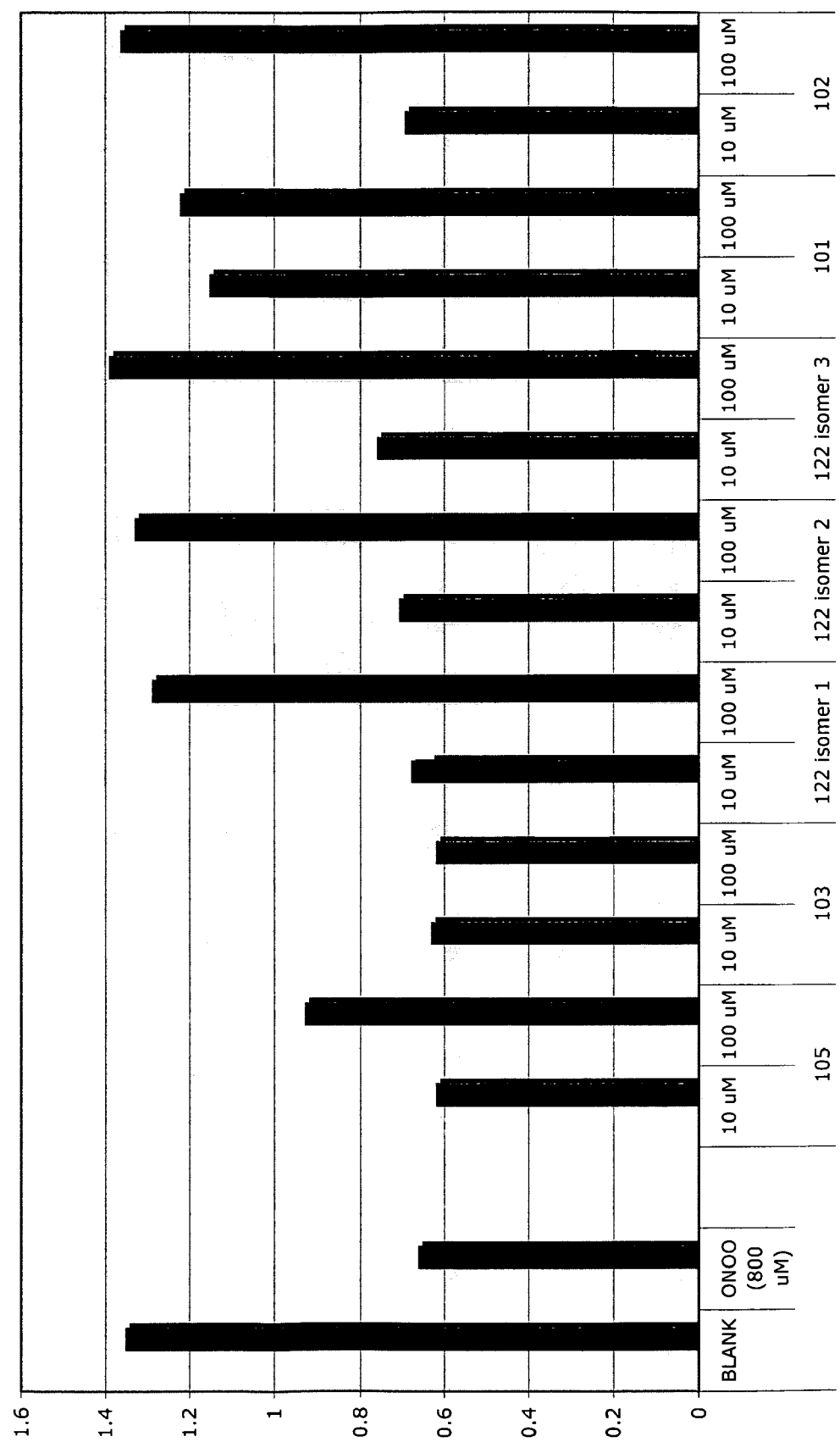

FIG. 11 shows the effect of Compounds 105, 103, 122 isomer 1, 122 isomer 2, 122 isomer 3, 101, and 102, respectively, on cell viability of murine RAW cells exposed to 800 μM ONOO⁻.

Figure 12:
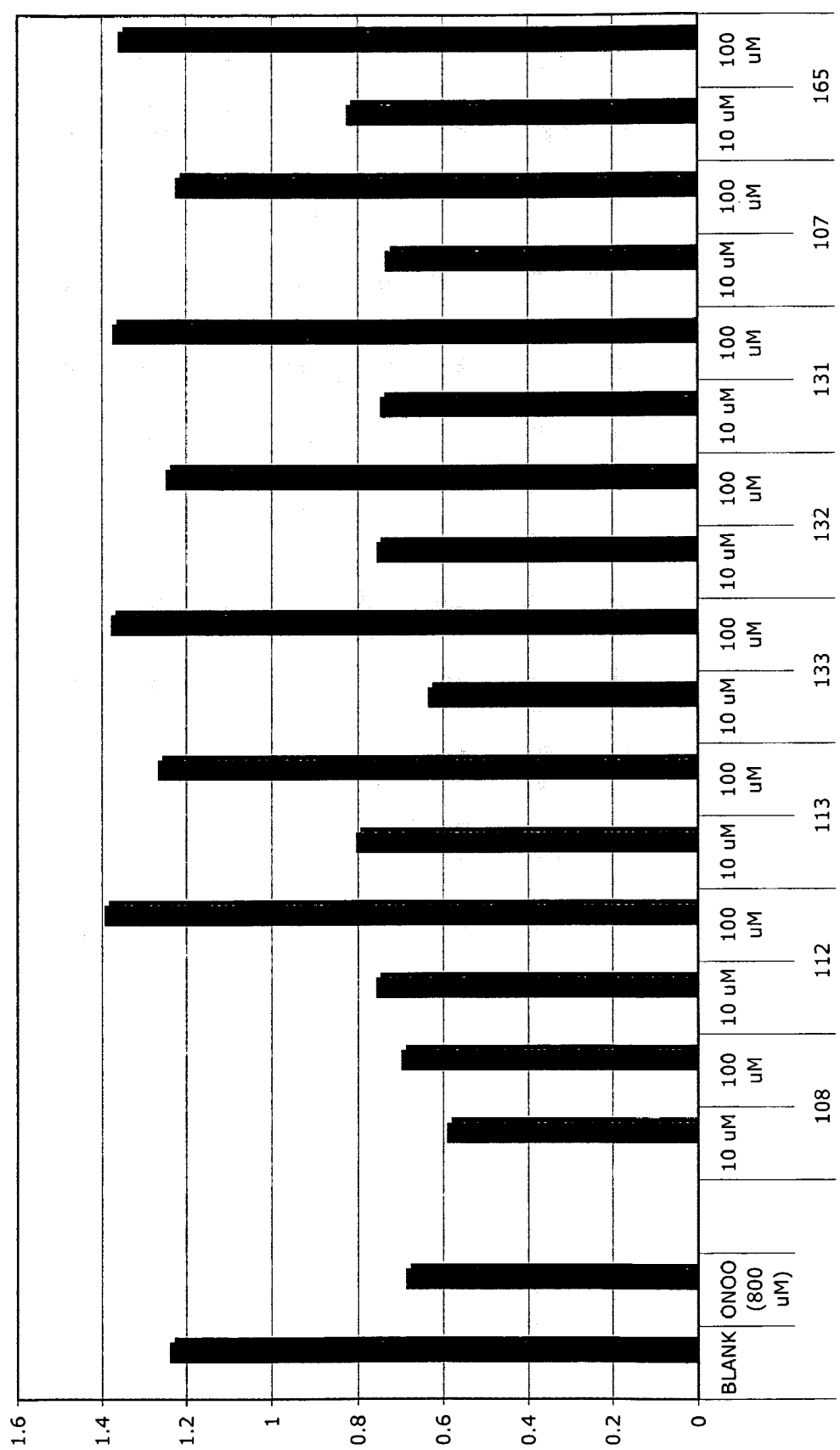

FIG. 12 shows the effect of Compounds 108, 112, 113, 133, 132, 131, 107, and 165, respectively, on cell viability of murine RAW cells exposed to 800 μM ONOO⁻.

5. DETAILED DESCRIPTION OF THE INVENTION

5.1 N-benzyl-substituted Pyridyl Porphyrin Compounds of Formula (A)

As stated above, the present invention encompasses N-Benzyl-Substituted Pyridyl Porphyrin Compounds having the formula:

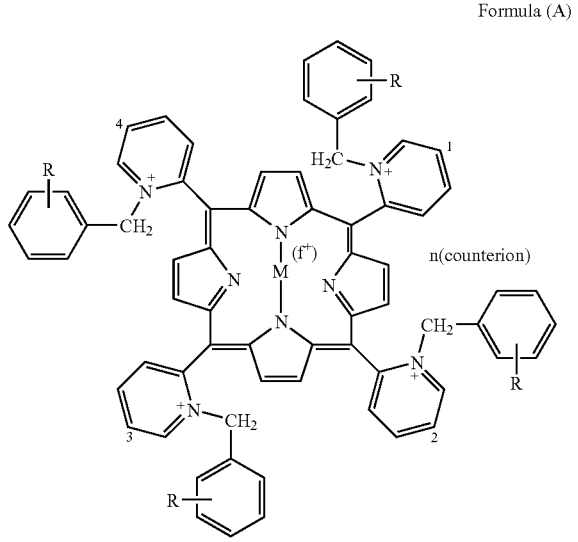

Formula (A)

wherein M, f, R, and n are defined above.

In one embodiment, f is 1, each counterion is monovalent, n is 5, and each amino acid residue is uncharged.

In one embodiment, f is 1, the counterion is monovalent, n is 1, and each amino acid residue has a —CO₂⁻ moiety as its only charged group.

In one embodiment, M is Fe.

In another embodiment, M is Mn.

In one embodiment, f is 1.

In another embodiment, f is 0.

In one embodiment, each counterion is Cl⁻ or Br⁻.

In one embodiment, each counterion is CH₃C(O)O⁻, 2-methylbenzoate, 3-methylbenzoate, or 4-methylbenzoate.

In one embodiment, a counterion forms a bond with M.

In one embodiment, a counterion that forms a bond with M is the same as a counterion that does not form a bond with M.

In one embodiment, a counterion that forms a bond with M is different from a counterion that does not form a bond with M.

In one embodiment, a counterion that does not form a bond with M is different from another counterion that does not form a bond with M.

In another embodiment, each counterion is independently F⁻, Cl⁻, Br⁻, I⁻, HO⁻, or CH₃C(O)O⁻.

In one embodiment, each R is —C(O)(amino acid residue).

In another embodiment, each R is —SO₂(amino acid residue).

In one embodiment, n is 0.

In one embodiment, n is 1.

In another embodiment, n is 5.

In one embodiment M is Fe, f is 1, and each counterion is Cl⁻.

In another embodiment, M is Fe, f is 1, each counterion is Cl⁻, and each occurrence of R is —C(O)(amino acid residue).

In another embodiment, M is Fe, f is 1, each counterion is Cl⁻, and each occurrence of R is —SO₂(amino acid residue).

In one embodiment, the amino acid of the amino acid residue is β-alanine, γ-aminobutyric acid, 6-aminohexanoic acid, 5-aminovaleric acid, L-aspartic acid, L-glutamine, L-glutamic acid, glycine, L-phenylalanine, L-tyrosine, or L-valine.

In one embodiment, each R is in the ortho position.

In one embodiment, each R is in the meta position.

In one embodiment, each R is in the para position.

In one embodiment, the N-Benzyl-Substituted Pyridyl Porphyrin Compounds of Formula (A) are in isolated and purified form.

The N-Benzyl-Substituted Pyridyl Porphyrin Compounds have four pyridyl groups. Due to steric factors, each pyridyl group's nitrogen atom can exist: (1) above the plane of the porphyrin ring (this conformation is herein referred to as the β-position); or (2) below the plane of the porphyrin ring (this conformation is herein referred to as the α-position).

In certain embodiments, the N-Benzyl-Substituted Pyridyl Porphyrin Compounds can exist in one of the following isomeric forms, denoted as Isomer Nos. 1-8, as described in the table below, or a mixture thereof, with the pyridyl groups being numbered 1-4 as shown in Formula (A):

|            | Pyridyl Group # |   |   |   |
| ---------- | --- | --- | --- | --- |
| Isomer No. | 1   | 2   | 3   | 4   |
| 1 | α | α | α | α |
| 2 | α | α | α | β |
| 3 | α | α | β | α |
| 4 | α | β | α | α |
| 5 | β | α | α | α |
| 6 | α | α | β | β |
| 7 | α | β | β | α |
| 8 | α | β | α | β |

In the above table, "α" signifies that the pyridyl group's nitrogen atom is in the α-position, and "β" signifies that the pyridyl group's nitrogen atom is in the β-position.

In one embodiment, the counterion that forms a bond with M exists above the plane of the porphyrin ring. In another embodiment, the counterion that forms a bond with M exists below the plane of the porphyrin ring.

In one embodiment, an N-Benzyl-Substituted Pyridyl Porphyrin Compound is substantially free of its corresponding other isomers.

In another embodiment, an N-Benzyl-Substituted Pyridyl Porphyrin Compound exists as a mixture of two or more isomers.

5.1.1 N-benzyl-substituted Pyridyl Porphyrin Compounds of Formula (I)

In one embodiment, the N-Benzyl-Substituted Pyridyl Porphyrin Compounds have the Formula (I)

Formula (I)

wherein M, f, R, and n are defined above for the N-Benzyl-Substituted Pyridyl Porphyrin Compounds.

In one embodiment, f is 1, each counterion is monovalent, n is 5, and each amino acid residue is uncharged.

In one embodiment, f is 1, the counterion is monovalent, n is 1, and each amino acid residue has a —$CO_2^-$ moiety as its only charged group.

In one embodiment, M is Fe.

In another embodiment, M is Mn.

In one embodiment, f is 1.

In another embodiment, f is 0.

In one embodiment, each counterion is $Cl^-$ or $Br^-$.

In one embodiment, each counterion is $CH_3C(O)O^-$ or 4-methylbenzoate.

In one embodiment, a counterion forms a bond with M.

In one embodiment, a counterion that forms a bond with M is the same as a counterion that does not form a bond with M.

In one embodiment, a counterion that forms a bond with M is different from a counterion that does not form a bond with M.

In one embodiment, a counterion that does not form a bond with M is different from another counterion that does not form a bond with M.

In another embodiment, each counterion is independently $F^-$, $Cl^-$, $Br^-$, $I^-$, $HO^-$, or $CH_3C(O)O^-$.

In one embodiment, each R is —C(O)(amino acid residue).

In another embodiment, each R is —$SO_2$(amino acid residue).

In one embodiment, n is 0.

In one embodiment, n is 1.

In another embodiment, n is 5.

In one embodiment M is Fe, f is 1, and each counterion is $Cl^-$.

In another embodiment, M is Fe, f is 1, each counterion is $Cl^-$, and each occurrence of R is —C(O)(amino acid residue).

In another embodiment, M is Fe, f is 1, each counterion is $Cl^-$, and each occurrence of R is —$SO_2$(amino acid residue).

In one embodiment, the amino acid of the amino acid residue is β-alanine, γ-aminobutyric acid, 6-aminohexanoic acid, 5-aminovaleric acid, L-aspartic acid, L-glutamine, L-glutamic acid, glycine, L-phenylalanine, L-tyrosine, or L-valine.

In one embodiment, the N-Benzyl-Substituted Pyridyl Porphyrin Compounds of Formula (I) are in isolated and purified form.

In one embodiment, the compounds of Formula (I) are of the Formula (IA):

Formula (IA)

wherein X⁻ and Y⁻ are each independently a counterion; and M is as set forth for Formula (I) above.

Illustrative examples of the compounds of Formula (IA) are as set forth below:

| Compound No. | Amino Acid of the Amino Acid Residue | M | Y⁻ | X⁻ |
|---|---|---|---|---|
| Compound 101 | γ-aminobutyric acid | Fe | OAc⁻ | Br⁻ |
| Compound 102 | 5-aminovaleric acid | Fe | OAc⁻ | Br⁻ |
| Compound 103 | L-aspartic acid | Mn | OAc⁻ | Br⁻ |
| Compound 104 | 5-aminovaleric acid | Mn | OAc⁻ | Br⁻ |
| Compound 105 | L-glutamic acid | Mn | OAc⁻ | Br⁻ |
| Compound 106 | L-phenylalanine | Fe | OAc⁻ | Br⁻ |
| Compound 107 | glycine | Fe | OAc⁻ | Br⁻ |
| Compound 108 | L-tyrosine | Fe | OAc⁻ | Br⁻ |
| Compound 109 | L-aspartic acid | Fe | OAc⁻ | Br⁻ |
| Compound 110 | glycine | Mn | OAc⁻ | Br⁻ |
| Compound 111 | β-alanine | Mn | OAc⁻ | Br⁻ |
| Compound 112 | β-alanine | Fe | OAc⁻ | Br⁻ |
| Compound 113 | L-valine | Fe | OAc⁻ | Br⁻ |
| Compound 114 | L-glutamine | Mn | OAc⁻ | Br⁻ |
| Compound 115 | 6-aminohexanoic acid | Fe | OAc⁻ | Br⁻ |

Additional illustrative examples of the compounds of Formula (IA) are as set forth below:

| Compound No. | Amino Acid of the Amino Acid Residue | M | Y⁻ | X⁻ |
|---|---|---|---|---|
| Compound 116 | γ-aminobutyric acid | Fe | Cl⁻ | Cl⁻ |
| Compound 117 | 5-aminovaleric acid | Fe | Cl⁻ | Cl⁻ |
| Compound 118 | L-aspartic acid | Mn | Cl⁻ | Cl⁻ |
| Compound 119 | 5-aminovaleric acid | Mn | Cl⁻ | Cl⁻ |
| Compound 120 | L-glutamic acid | Mn | Cl⁻ | Cl⁻ |
| Compound 121 | L-phenylalanine | Fe | Cl⁻ | Cl⁻ |
| Compound 122 | glycine | Fe | Cl⁻ | Cl⁻ |
| Compound 123 | L-tyrosine | Fe | Cl⁻ | Cl⁻ |
| Compound 124 | L-aspartic acid | Fe | Cl⁻ | Cl⁻ |
| Compound 125 | glycine | Mn | Cl⁻ | Cl⁻ |
| Compound 126 | β-alanine | Mn | Cl⁻ | Cl⁻ |
| Compound 127 | β-alanine | Fe | Cl⁻ | Cl⁻ |
| Compound 128 | L-valine | Fe | Cl⁻ | Cl⁻ |
| Compound 129 | L-glutamine | Mn | Cl⁻ | Cl⁻ |
| Compound 130 | 6-aminohexanoic acid | Fe | Cl⁻ | Cl⁻ |

In one embodiment, the compounds of Formula (I) are of the Formula (IB):

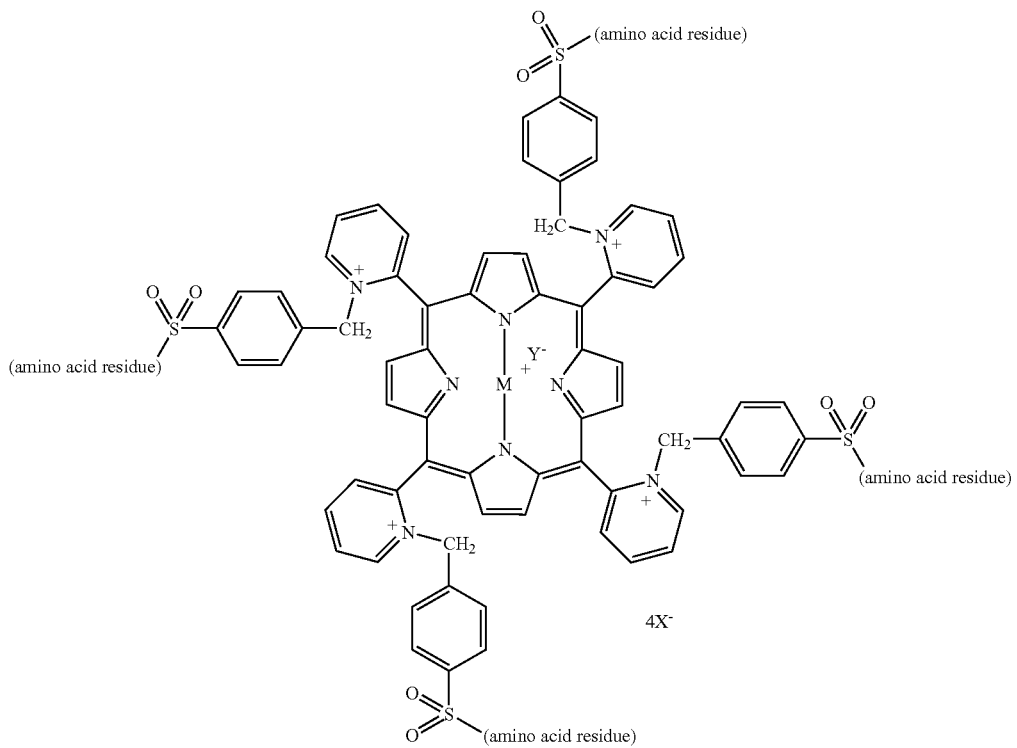

Formula (IB)

wherein X⁻ and Y⁻ are each independently a counterion; and M is as set forth for Formula (I) above.

Illustrative examples of the compounds of Formula (IB) are as set forth below:

| Compound No. | Amino Acid of the Amino Acid Residue | M | Y⁻ | X⁻ |
|---|---|---|---|---|
| Compound 131 | 6-aminohexanoic acid | Fe | OAc⁻ | Br⁻ |
| Compound 132 | β-alanine | Fe | OAc⁻ | Br⁻ |
| Compound 133 | glycine | Fe | OAc⁻ | Br⁻ |
| Compound 134 | γ-aminobutyric acid | Fe | OAc⁻ | Br⁻ |
| Compound 135 | 5-aminovaleric acid | Fe | OAc⁻ | Br⁻ |
| Compound 136 | L-aspartic acid | Mn | OAc⁻ | Br⁻ |
| Compound 137 | 5-aminovaleric acid | Mn | OAc⁻ | Br⁻ |
| Compound 138 | L-glutamic acid | Mn | OAc⁻ | Br⁻ |
| Compound 139 | L-phenylalanine | Fe | OAc⁻ | Br⁻ |
| Compound 140 | L-tyrosine | Fe | OAc⁻ | Br⁻ |
| Compound 141 | L-aspartic acid | Fe | OAc⁻ | Br⁻ |
| Compound 142 | glycine | Mn | OAc⁻ | Br⁻ |
| Compound 143 | β-alanine | Mn | OAc⁻ | Br⁻ |
| Compound 144 | L-valine | Fe | OAc⁻ | Br⁻ |
| Compound 145 | L-glutamine | Mn | OAc⁻ | Br⁻ |

Additional illustrative examples of the compounds of Formula (IB) are as set forth below:

| Compound No. | Amino Acid of the Amino Acid Residue | M | Y⁻ | X⁻ |
|---|---|---|---|---|
| Compound 146 | 6-aminohexanoic acid | Fe | Cl⁻ | Cl⁻ |
| Compound 147 | β-alanine | Fe | Cl⁻ | Cl⁻ |
| Compound 148 | glycine | Fe | Cl⁻ | Cl⁻ |
| Compound 149 | γ-aminobutyric acid | Fe | Cl⁻ | Cl⁻ |
| Compound 150 | 5-aminovaleric acid | Fe | Cl⁻ | Cl⁻ |
| Compound 151 | L-aspartic acid | Mn | Cl⁻ | Cl⁻ |
| Compound 152 | 5-aminovaleric acid | Mn | Cl⁻ | Cl⁻ |
| Compound 153 | L-glutamic acid | Mn | Cl⁻ | Cl⁻ |
| Compound 154 | L-phenylalanine | Fe | Cl⁻ | Cl⁻ |
| Compound 155 | L-tyrosine | Fe | Cl⁻ | Cl⁻ |
| Compound 156 | L-aspartic acid | Fe | Cl⁻ | Cl⁻ |
| Compound 157 | glycine | Mn | Cl⁻ | Cl⁻ |
| Compound 158 | β-alanine | Mn | Cl⁻ | Cl⁻ |
| Compound 159 | L-valine | Fe | Cl⁻ | Cl⁻ |
| Compound 160 | L-glutamine | Mn | Cl⁻ | Cl⁻ |

The N-Benzyl-Substituted Pyridyl Porphyrin Compounds of Formula (I) have four pyridyl groups. Due to steric factors, each pyridyl group's nitrogen atom can exist: (1) above the plane of the porphyrin ring (this conformation is herein referred to as the β-position); or (2) below the plane of the porphyrin ring (this conformation is herein referred to as the α-position).

In certain embodiments, the N-Benzyl-Substituted Pyridyl Porphyrin Compounds of Formula (I) can exist in one of the following isomeric forms, denoted as Isomer Nos. 1-8, as described in the table below, or a mixture thereof, with the pyridyl groups being numbered 1-4 as shown in Formula (I):

| | Pyridyl Group # | | | |
|---|---|---|---|---|
| Isomer No. | 1 | 2 | 3 | 4 |
| 1 | α | α | α | α |
| 2 | α | α | α | β |
| 3 | α | α | β | α |
| 4 | α | β | α | α |
| 5 | β | α | α | α |
| 6 | α | α | β | β |
| 7 | α | β | β | α |
| 8 | α | β | α | β |

In the above table, "α" signifies that the pyridyl group's nitrogen atom is in the α-position, and "β" signifies that the pyridyl group's nitrogen atom is in the β-position.

In one embodiment, the counterion that forms a bond with M exists above the plane of the porphyrin ring. In another embodiment, the counterion that forms a bond with M exists below the plane of the porphyrin ring.

In one embodiment, an N-Benzyl-Substituted Pyridyl Porphyrin Compound of Formula (I) is substantially free of its corresponding other isomers.

In another embodiment, an N-Benzyl-Substituted Pyridyl Porphyrin Compound of Formula (I) exists as a mixture of two or more isomers.

5.1.2 N-benzyl-substituted Pyridyl Porphyrin Compounds of Formula (II)

In one embodiment, the N-Benzyl-Substituted Pyridyl Porphyrin Compounds have the Formula (II)

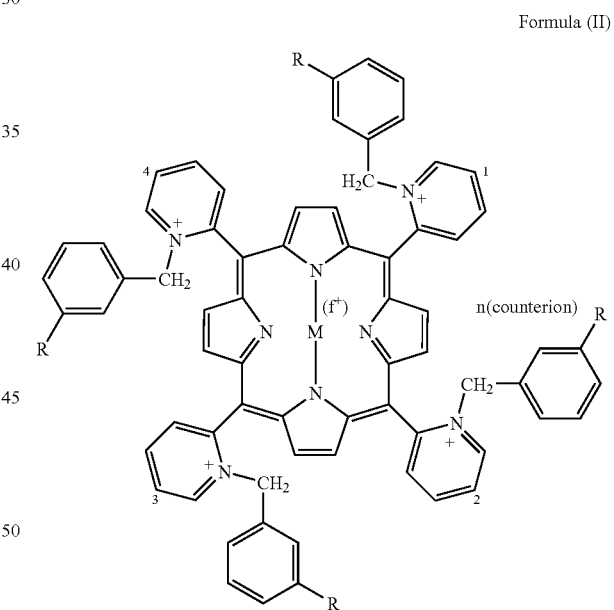

Formula (II)

wherein M, f, R, and n are defined above for the N-Benzyl-Substituted Pyridyl Porphyrin Compounds of Formula (A).

In one embodiment, f is 1, each counterion is monovalent, n is 5, and each amino acid residue is uncharged.

In one embodiment, f is 1, the counterion is monovalent, n is 1, and each amino acid residue has a —$CO_2^-$ moiety as its only charged group.

In one embodiment M is Fe.

In another embodiment, M is Mn.

In one embodiment, f is 1.

In another embodiment, f is 0.

In one embodiment, each counterion is Cl⁻ or Br⁻.

In one embodiment, each counterion is $CH_3C(O)O^-$ or 3-methylbenzoate.

In one embodiment, a counterion forms a bond with M.

In one embodiment, a counterion that forms a bond with M is the same as a counterion that does not form a bond with M.

In one embodiment, a counterion that forms a bond with M is different from a counterion that does not form a bond with M.

In one embodiment, a counterion that does not form a bond with M is different from another counterion that does not form a bond with M.

In another embodiment, each counterion is independently $F^-$, $Cl^-$, $Br^-$, $I^-$, $HO^-$, or $CH_3C(O)O^-$.

In one embodiment, each R is —C(O)(amino acid residue).

In another embodiment, each R is —$SO_2$(amino acid residue).

In one embodiment, n is 0.

In one embodiment, n is 1.

In another embodiment, n is 5.

In one embodiment M is Fe, f is 1, and each counterion is $Cl^-$.

In another embodiment, M is Fe, f is 1, each counterion is $Cl^-$, and each occurrence of R is —C(O)(amino acid residue).

In another embodiment, M is Fe, f is 1, each counterion is $Cl^-$, and each occurrence of R is —$SO_2$(amino acid residue).

In one embodiment, the amino acid of the amino acid residue is β-alanine, γ-aminobutyric acid, 6-aminohexanoic acid, 5-aminovaleric acid, L-aspartic acid, L-glutamine, L-glutamic acid, glycine, L-phenylalanine, L-tyrosine, or L-valine.

In one embodiment, the N-Benzyl-Substituted Pyridyl Porphyrin Compounds of Formula (II) are in isolated and purified form.

In one embodiment, the compound of Formula (II) is of the Formula (IIA):

wherein $X^-$ and $Y^-$ are each independently a counterion; and M is as set forth for Formula (II) above.

Illustrative examples of the compounds of Formula (IIA) are as set forth below:

| Compound No. | Amino Acid of the Amino Acid Residue | M | $Y^-$ | $X^-$ |
|---|---|---|---|---|
| Compound 161 | L-valine | Fe | $OAc^-$ | Br– |
| Compound 162 | L-tyrosine | Fe | $OAc^-$ | Br– |
| Compound 163 | L-phenylalanine | Fe | $OAc^-$ | Br– |
| Compound 164 | β-alanine | Mn | $OAc^-$ | Br– |
| Compound 165 | glycine | Fe | $OAc^-$ | Br– |
| Compound 166 | 6-aminohexanoic acid | Fe | $OAc^-$ | Br– |
| Compound 167 | γ-aminobutyric acid | Fe | $OAc^-$ | Br– |
| Compound 168 | 5-aminovaleric acid | Fe | $OAc^-$ | Br– |
| Compound 169 | L-aspartic acid | Mn | $OAc^-$ | Br– |
| Compound 170 | 5-aminovaleric acid | Mn | $OAc^-$ | Br– |
| Compound 171 | L-glutamic acid | Mn | $OAc^-$ | Br– |
| Compound 172 | L-aspartic acid | Fe | $OAc^-$ | Br– |
| Compound 173 | glycine | Mn | $OAc^-$ | Br– |
| Compound 174 | β-alanine | Fe | $OAc^-$ | Br– |
| Compound 175 | L-glutamine | Mn | $OAc^-$ | Br– |

Additional illustrative examples of the compounds of Formula (IIA) are as set forth below:

| Compound No. | Amino Acid of the Amino Acid Residue | M | $Y^-$ | $X^-$ |
|---|---|---|---|---|
| Compound 176 | L-valine | Fe | $Cl^-$ | $Cl^-$ |
| Compound 177 | L-tyrosine | Fe | $Cl^-$ | $Cl^-$ |
| Compound 178 | L-phenylalanine | Fe | $Cl^-$ | $Cl^-$ |
| Compound 179 | β-alanine | Mn | $Cl^-$ | $Cl^-$ |
| Compound 180 | glycine | Fe | $Cl^-$ | $Cl^-$ |
| Compound 181 | 6-aminohexanoic acid | Fe | $Cl^-$ | $Cl^-$ |
| Compound 182 | γ-aminobutyric acid | Fe | $Cl^-$ | $Cl^-$ |
| Compound 183 | 5-aminovaleric acid | Fe | $Cl^-$ | $Cl^-$ |

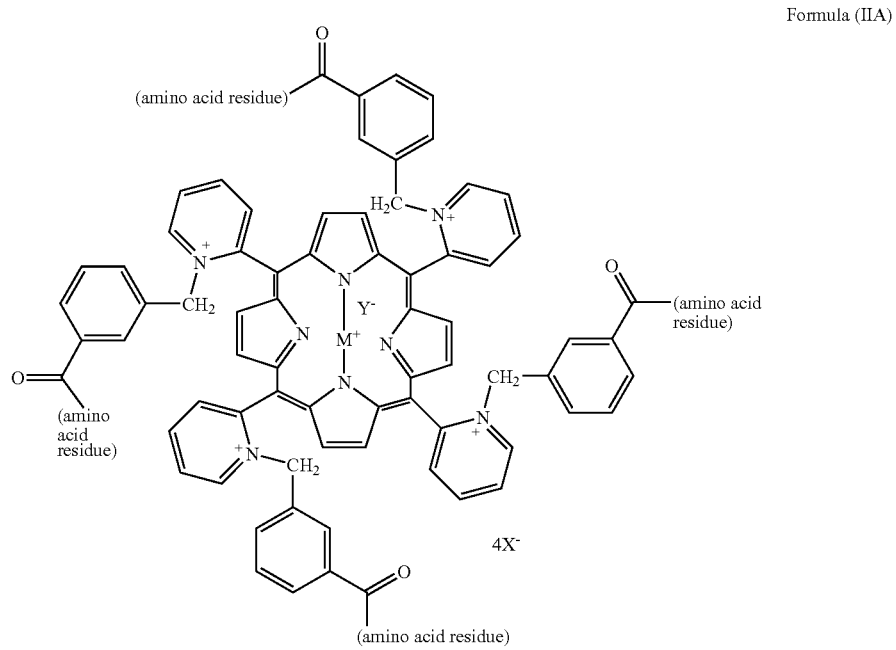

Formula (IIA)

-continued

| Compound No. | Amino Acid of the Amino Acid Residue | M | Y⁻ | X⁻ |
|---|---|---|---|---|
| Compound 184 | L-aspartic acid | Mn | Cl⁻ | Cl⁻ |
| Compound 185 | 5-aminovaleric acid | Mn | Cl⁻ | Cl⁻ |
| Compound 186 | L-glutamic acid | Mn | Cl⁻ | Cl⁻ |
| Compound 187 | L-aspartic acid | Fe | Cl⁻ | Cl⁻ |
| Compound 188 | glycine | Mn | Cl⁻ | Cl⁻ |
| Compound 189 | β-alanine | Fe | Cl⁻ | Cl⁻ |
| Compound 190 | L-glutamine | Mn | Cl⁻ | Cl⁻ |

In one embodiment, the compound of Formula (II) is of the Formula (IIB):

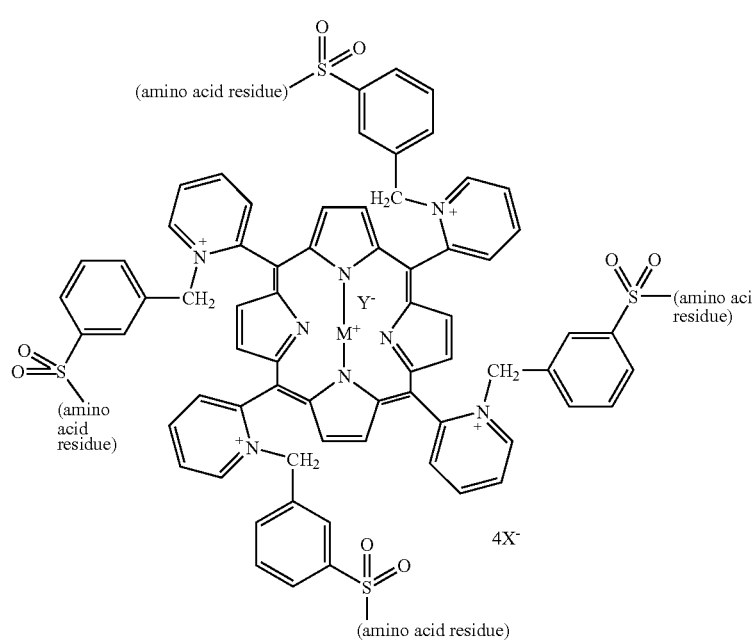

Formula (IIB)

wherein X⁻ and Y⁻ are each independently a counterion; and M is as set forth for Formula (II) above.

Illustrative examples of the compounds of Formula (IIB) are as set forth below:

| Compound No. | Amino Acid of the Amino Acid Residue | M | Y⁻ | X⁻ |
|---|---|---|---|---|
| Compound 191 | γ-aminobutyric acid | Fe | OAc⁻ | Br⁻ |
| Compound 192 | 5-aminovaleric acid | Fe | OAc⁻ | Br⁻ |
| Compound 193 | L-aspartic acid | Mn | OAc⁻ | Br⁻ |
| Compound 194 | 5-aminovaleric acid | Mn | OAc⁻ | Br⁻ |
| Compound 195 | L-glutamic acid | Mn | OAc⁻ | Br⁻ |
| Compound 196 | L-phenylalanine | Fe | OAc⁻ | Br⁻ |
| Compound 197 | glycine | Fe | OAc⁻ | Br⁻ |
| Compound 198 | L-tyrosine | Fe | OAc⁻ | Br⁻ |
| Compound 199 | L-aspartic acid | Fe | OAc⁻ | Br⁻ |
| Compound 200 | glycine | Mn | OAc⁻ | Br⁻ |
| Compound 201 | β-alanine | Mn | OAc⁻ | Br⁻ |
| Compound 202 | β-alanine | Fe | OAc⁻ | Br⁻ |
| Compound 203 | L-valine | Fe | OAc⁻ | Br⁻ |
| Compound 204 | L-glutamine | Mn | OAc⁻ | Br⁻ |
| Compound 205 | 6-aminohexanoic acid | Fe | OAc⁻ | Br⁻ |

Additional illustrative examples of the compounds of Formula (IIB) are as set forth below:

| Compound No. | Amino Acid of the Amino Acid Residue | M | Y⁻ | X⁻ |
|---|---|---|---|---|
| Compound 206 | γ-aminobutyric acid | Fe | Cl⁻ | Cl⁻ |
| Compound 207 | 5-aminovaleric acid | Fe | Cl⁻ | Cl⁻ |
| Compound 208 | L-aspartic acid | Mn | Cl⁻ | Cl⁻ |
| Compound 209 | 5-aminovaleric acid | Mn | Cl⁻ | Cl⁻ |
| Compound 210 | L-glutamic acid | Mn | Cl⁻ | Cl⁻ |
| Compound 211 | L-phenylalanine | Fe | Cl⁻ | Cl⁻ |
| Compound 212 | glycine | Fe | Cl⁻ | Cl⁻ |
| Compound 213 | L-tyrosine | Fe | Cl⁻ | Cl⁻ |
| Compound 214 | L-aspartic acid | Fe | Cl⁻ | Cl⁻ |
| Compound 215 | glycine | Mn | Cl⁻ | Cl⁻ |
| Compound 216 | β-alanine | Mn | Cl⁻ | Cl⁻ |
| Compound 217 | β-alanine | Fe | Cl⁻ | Cl⁻ |
| Compound 218 | L-valine | Fe | Cl⁻ | Cl⁻ |
| Compound 219 | L-glutamine | Mn | Cl⁻ | Cl⁻ |
| Compound 230 | 6-aminohexanoic acid | Fe | Cl⁻ | Cl⁻ |

The N-Benzyl-Substituted Pyridyl Porphyrin Compounds of Formula (II) have four pyridyl groups. Due to steric factors, each pyridyl group's nitrogen atom can exist: (1) above the plane of the porphyrin ring (this conformation is herein referred to as the β-position); or (2) below the plane of the porphyrin ring (this conformation is herein referred to as the α-position).

In certain embodiments, the N-Benzyl-Substituted Pyridyl Porphyrin Compounds of Formula (II) can exist in one of the following isomeric forms, denoted as Isomer Nos. 1-8, as described in the table below, or a mixture thereof, with the pyridyl groups being numbered 1-4 as shown in Formula (II):

|           | Pyridyl Group # |   |   |   |
|-----------|---|---|---|---|
| Isomer No. | 1 | 2 | 3 | 4 |
| 1 | α | α | α | α |
| 2 | α | α | α | β |
| 3 | α | α | β | α |
| 4 | α | β | α | α |
| 5 | β | α | α | α |
| 6 | α | α | β | β |
| 7 | α | β | β | α |
| 8 | α | β | α | β |

In the above table, "α" signifies that the pyridyl group's nitrogen atom is in the α-position, and "β" signifies that the pyridyl group's nitrogen atom is in the β-position.

In one embodiment, the counterion that forms a bond with M exists above the plane of the porphyrin ring. In another embodiment, the counterion that forms a bond with M exists below the plane of the porphyrin ring.

In one embodiment, an N-Benzyl-Substituted Pyridyl Porphyrin Compound of Formula (II) is substantially free of its corresponding other isomers.

In another embodiment, an N-Benzyl-Substituted Pyridyl Porphyrin Compound of Formula (II) exists as a mixture of two or more isomers.

5.1.3 N-benzyl-substituted Pyridyl Porphyrin Compounds of Formula (III)

In one embodiment, the N-Benzyl-Substituted Pyridyl Porphyrin Compounds have the Formula (III)

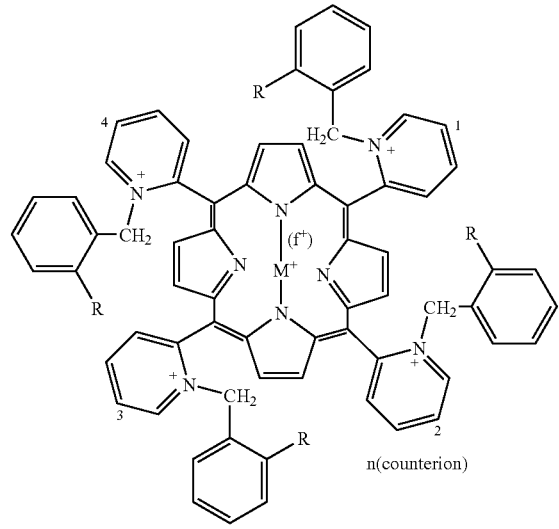

Formula (III)

wherein M, f, R, and n are defined above for the N-Benzyl-Substituted Pyridyl Porphyrin Compounds of Formula (A).

In one embodiment, f is 1, each counterion is monovalent, n is 5, and each amino acid residue is uncharged.

In one embodiment, f is 1, the counterion is monovalent, n is 1, and each amino acid residue has a $—CO_2^-$ moiety as its only charged group.

In one embodiment M is Fe.
In another embodiment, M is Mn.
In one embodiment, f is 1.
In another embodiment, f is 0.
In one embodiment, each counterion is $Cl^-$ or $Br^-$.
In one embodiment, each counterion is $CH_3C(O)O^-$ or 2-methylbenzoate.
In one embodiment, a counterion forms a bond with M.
In one embodiment, a counterion that forms a bond with M is the same as a counterion that does not form a bond with M.
In one embodiment, a counterion that forms a bond with M is a different from a counterion that does not form a bond with M.
In one embodiment, a counterion that does not form a bond with M is different from another counterion that does not form a bond with M.
In another embodiment, each counterion is independently $F^-$, $Cl^-$, $Br^-$, $I^-$, $HO^-$, or $CH_3C(O)O^-$.
In one embodiment, each R is —C(O)(amino acid residue).
In another embodiment, each R is —SO$_2$(amino acid residue).
In one embodiment, n is 0.
In one embodiment, n is 1.
In another embodiment, n is 5.
In one embodiment M is Fe, f is 1, and each counterion is $Cl^-$.
In another embodiment, M is Fe, f is 1, each counterion is $Cl^-$, and each occurrence of R is —C(O)(amino acid residue).
In another embodiment, M is Fe, f is 1, each counterion is $Cl^-$, and each occurrence of R is —SO$_2$(amino acid residue).
In one embodiment, the amino acid of the amino acid residue is β-alanine, γ-aminobutyric acid, 6-aminohexanoic acid, 5-aminovaleric acid, L-aspartic acid, L-glutamine, L-glutamic acid, glycine, L-phenylalanine, L-tyrosine, or L-valine.
In one embodiment, the N-Benzyl Substituted Pyridyl Porphyrin Compounds of Formula (III) are in isolated and purified form.
In one embodiment, the compound of Formula (III) is of the Formula (IIIA):

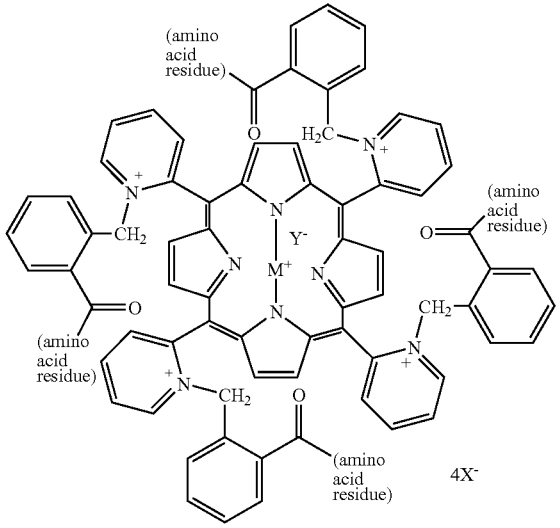

Formula (IIIA)

wherein X⁻ and Y⁻ are each independently a counterion; and M is as set forth for Formula (III) above.

Illustrative examples of the compounds of Formula (IIIA) are as set forth below:

| Compound No. | Amino Acid of the Amino Acid Residue | M | Y⁻ | X⁻ |
|---|---|---|---|---|
| Compound 231 | γ-aminobutyric acid | Fe | OAc⁻ | Br⁻ |
| Compound 232 | 5-aminovaleric acid | Fe | OAc⁻ | Br⁻ |
| Compound 233 | L-aspartic acid | Mn | OAc⁻ | Br⁻ |
| Compound 234 | 5-aminovaleric acid | Mn | OAc⁻ | Br⁻ |
| Compound 235 | L-glutamic acid | Mn | OAc⁻ | Br⁻ |
| Compound 236 | L-phenylalanine | Fe | OAc⁻ | Br⁻ |
| Compound 237 | glycine | Fe | OAc⁻ | Br⁻ |
| Compound 238 | L-tyrosine | Fe | OAc⁻ | Br⁻ |
| Compound 239 | L-aspartic acid | Fe | OAc⁻ | Br⁻ |
| Compound 240 | glycine | Mn | OAc⁻ | Br⁻ |
| Compound 241 | β-alanine | Mn | OAc⁻ | Br⁻ |
| Compound 242 | β-alanine | Fe | OAc⁻ | Br⁻ |
| Compound 243 | L-valine | Fe | OAc⁻ | Br⁻ |
| Compound 244 | L-glutamine | Mn | OAc⁻ | Br⁻ |
| Compound 245 | 6-aminohexanoic acid | Fe | OAc⁻ | Br⁻ |

Additional illustrative examples of the compounds of Formula (IIIA) are as set forth below:

| Compound No. | Amino Acid of the Amino Acid Residue | M | Y⁻ | X⁻ |
|---|---|---|---|---|
| Compound 246 | γ-aminobutyric acid | Fe | Cl⁻ | Cl⁻ |
| Compound 247 | 5-aminovaleric acid | Fe | Cl⁻ | Cl⁻ |
| Compound 248 | L-aspartic acid | Mn | Cl⁻ | Cl⁻ |
| Compound 249 | 5-aminovaleric acid | Mn | Cl⁻ | Cl⁻ |
| Compound 250 | L-glutamic acid | Mn | Cl⁻ | Cl⁻ |
| Compound 251 | L-phenylalanine | Fe | Cl⁻ | Cl⁻ |
| Compound 252 | glycine | Fe | Cl⁻ | Cl⁻ |
| Compound 253 | L-tyrosine | Fe | Cl⁻ | Cl⁻ |
| Compound 254 | L-aspartic acid | Fe | Cl⁻ | Cl⁻ |
| Compound 255 | glycine | Mn | Cl⁻ | Cl⁻ |
| Compound 256 | β-alanine | Mn | Cl⁻ | Cl⁻ |
| Compound 257 | β-alanine | Fe | Cl⁻ | Cl⁻ |
| Compound 258 | L-valine | Fe | Cl⁻ | Cl⁻ |
| Compound 259 | L-glutamine | Mn | Cl⁻ | Cl⁻ |
| Compound 260 | 6-aminohexanoic acid | Fe | Cl⁻ | Cl⁻ |

In one embodiment, the compound of Formula (III) is of the Formula (IIIB):

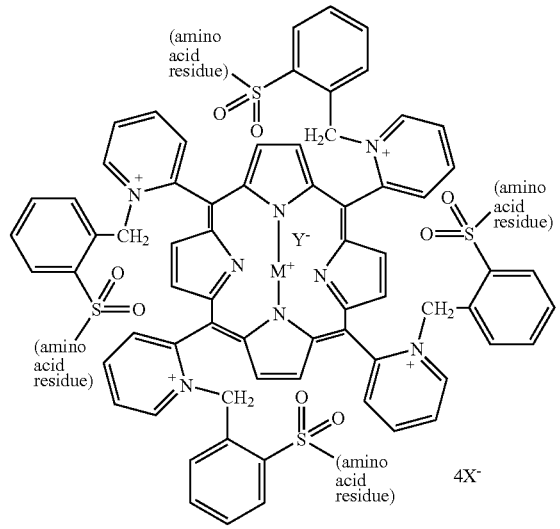

Formula (IIIB)

wherein X⁻ and Y⁻ are each independently a counterion; and M is as set forth for Formula (III) above.

Illustrative examples of the compounds of Formula (IIIB) are as set forth below:

| Compound No. | Amino Acid of the Amino Acid Residue | M | Y⁻ | X⁻ |
|---|---|---|---|---|
| Compound 261 | γ-aminobutyric acid | Fe | OAc⁻ | Br⁻ |
| Compound 262 | 5-aminovaleric acid | Fe | OAc⁻ | Br⁻ |
| Compound 263 | L-aspartic acid | Mn | OAc⁻ | Br⁻ |
| Compound 264 | 5-aminovaleric acid | Mn | OAc⁻ | Br⁻ |
| Compound 265 | L-glutamic acid | Mn | OAc⁻ | Br⁻ |
| Compound 266 | L-phenylalanine | Fe | OAc⁻ | Br⁻ |
| Compound 267 | glycine | Fe | OAc⁻ | Br⁻ |
| Compound 268 | L-tyrosine | Fe | OAc⁻ | Br⁻ |
| Compound 269 | L-aspartic acid | Fe | OAc⁻ | Br⁻ |
| Compound 270 | glycine | Mn | OAc⁻ | Br⁻ |
| Compound 271 | β-alanine | Mn | OAc⁻ | Br⁻ |
| Compound 272 | β-alanine | Fe | OAc⁻ | Br⁻ |
| Compound 273 | L-valine | Fe | OAc⁻ | Br⁻ |
| Compound 274 | L-glutamine | Mn | OAc⁻ | Br⁻ |
| Compound 275 | 6-aminohexanoic acid | Fe | OAc⁻ | Br⁻ |

Additional illustrative examples of the compounds of Formula (IIIB) are as set forth below:

| Compound No. | Amino Acid of the Amino Acid Residue | M | Y⁻ | X⁻ |
|---|---|---|---|---|
| Compound 276 | γ-aminobutyric acid | Fe | Cl⁻ | Cl⁻ |
| Compound 277 | 5-aminovaleric acid | Fe | Cl⁻ | Cl⁻ |
| Compound 278 | L-aspartic acid | Mn | Cl⁻ | Cl⁻ |
| Compound 279 | 5-aminovaleric acid | Mn | Cl⁻ | Cl⁻ |
| Compound 280 | L-glutamic acid | Mn | Cl⁻ | Cl⁻ |
| Compound 281 | L-phenylalanine | Fe | Cl⁻ | Cl⁻ |
| Compound 282 | glycine | Fe | Cl⁻ | Cl⁻ |
| Compound 283 | L-tyrosine | Fe | Cl⁻ | Cl⁻ |
| Compound 284 | L-aspartic acid | Fe | Cl⁻ | Cl⁻ |
| Compound 285 | glycine | Mn | Cl⁻ | Cl⁻ |
| Compound 286 | β-alanine | Mn | Cl⁻ | Cl⁻ |
| Compound 287 | β-alanine | Fe | Cl⁻ | Cl⁻ |
| Compound 288 | L-valine | Fe | Cl⁻ | Cl⁻ |
| Compound 289 | L-glutamine | Mn | Cl⁻ | Cl⁻ |
| Compound 290 | 6-aminohexanoic acid | Fe | Cl⁻ | Cl⁻ |

The N-Benzyl-Substituted Pyridyl Porphyrin Compounds of Formula (III) have four pyridyl groups. Due to steric factors, each pyridyl group's nitrogen atom can exist: (1) above the plane of the porphyrin ring (this conformation is herein referred to as the β-position); or (2) below the plane of the porphyrin ring (this conformation is herein referred to as the α-position).

In certain embodiments, the N-Benzyl-Substituted Pyridyl Porphyrin Compounds of Formula (I) can exist in one of the following isomeric forms, denoted as Isomer Nos. 1-8, as described in the table below, or a mixture thereof, with the pyridyl groups being numbered 1-4 as shown in Formula (III):

| Isomer No. | Pyridyl Group # | | | |
|---|---|---|---|---|
| | 1 | 2 | 3 | 4 |
| 1 | α | α | α | α |
| 2 | α | α | α | β |
| 3 | α | α | β | α |
| 4 | α | β | α | α |
| 5 | β | α | α | α |
| 6 | α | α | β | β |
| 7 | α | β | β | α |
| 8 | α | β | α | β |

In the above table, "α" signifies that the pyridyl group's nitrogen atom is in the α-position, and "β" signifies that the pyridyl group's nitrogen atom is in the β-position.

In one embodiment, the counterion that forms a bond with M exists above the plane of the porphyrin ring. In another embodiment, the counterion that forms a bond with M exists below the plane of the porphyrin ring.

In one embodiment, an N-Benzyl-Substituted Pyridyl Porphyrin Compound of Formula (III) is substantially free of its corresponding other isomers.

In another embodiment, an N-Benzyl-Substituted Pyridyl Porphyrin Compound of Formula (III) exists as a mixture of two or more isomers.

5.2 Definitions

As used herein, the terms used above and below have the following meaning:

The term "amino acid residue," as used herein, refers to a radical derived from a natural or an unnatural amino acid, less a hydrogen atom of the amino acid's terminal amino group. For example, where the amino acid of the amino acid residue is glycine, the amino acid residue has the formula —NHCH$_2$CO$_2$H. Accordingly, in the N-Benzyl-Substituted Pyridyl Porphyrin Compounds, —C(O)(amino acid residue) is an amido group and —SO$_2$(amino acid residue) is a sulfonamide group. Representative examples of amino acids from which an "amino acid residue" is derived include, but are not limited to, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, N-acetyllysine, β-alanine, aminoadipic acid, γ-aminobutyric acid, 6-aminohexanoic acid, 5-aminovaleric acid, azaserine O-diazoacetylserine, betaine, γ-carboxyglutamic acid, L-chloramphenicol, citrulline, cycloserine, epinephrine, histamine, homocysteine, homoserine, 5-hydroxylysine, 4-hydroxyproline, L-lanthionine, 3-methylhistidine, N-methylarginine, N-methylglycine, ε-N-methyllysine, norleucine, ornithine, penicillamine, L-phenylserine, phosphoserine, phospho-threonine, phosphotyrosine, pyroglutamic acid, serotonin, and thyroxine. In one embodiment, the acid of the amino acid is a C$_2$-C$_{20}$ alkanoic acid. In one embodiment, the amino acid is alanine, β-alanine, γ-aminobutyric acid, 6-aminohexanoic acid, 5-aminovaleric acid, arginine, asparagine, aspartic acid, cysteine, glutamic acid, glutamine, glycine, histidine, isoleucine, leucine, lysine, methionine, phenylalanine, proline, serine, threonine, tryptophan, tyrosine, or valine. In one embodiment, the amino acid is a racemic amino acid. In one embodiment, the amino acid is an L-amino acid. In another embodiment, the amino acid is a D-amino acid. In one embodiment, the amino acid is present in its zwitterionic (neutral) form.

The term "subject," as used herein, includes, but is not limited to, a cow, monkey, horse, sheep, pig, chicken, turkey, quail, cat, dog, mouse, rat, rabbit, guinea pig and human. In one embodiment, the subject is a human.

Where n, the number of counterions sufficient to balance the charges of the N-Benzyl-Substituted Pyridyl Porphyrin Compound, is greater than 1, each counterion can be the same or different. Illustrative counterions include, but are not limited to, sulfate, citrate, acetate, oxalate, flouride, chloride, bromide, iodide, nitrate, bisulfate, monophosphate, diphosphate, triphosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, pamoate (i.e., 1,1'-methylene-bis-(2-hydroxy-3-naphthoate)), camphorsulfonate, 2-methylbenzoate, 3-methylbenzoate, and 4-methylbenzoate counterions. In one embodiment, a counterion is monovalent. Examples of monovalent counterions include acetate, chloride, bromide, iodide, nitrate, bisulfate, salicylate, oleate, bitartrate, formate, benzoate, methanesulfonate, ethanesulfonate, benzenesulfonate, p-toluenesulfonate, camphorsulfonate, 2-methylbenzoate, 3-methylbenzoate, and 4-methylbenzoate counterions. In another embodiment, a counterion is divalent.

The term "effective amount" when used in connection with an N-Benzyl-Substituted Pyridyl Porphyrin Compound is an amount that is effective to treat or prevent a Condition or to prolong the half-life of an oxidation-prone compound in a subject alone or in combination with another prophylactic or therapeutic agent.

The term "isolated and purified" as used herein means separated from other components of a reaction mixture or natural source. In certain embodiments, the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of an N-Benzyl-Substituted Pyridyl Porphyrin Compound by weight of the isolate. In one embodiment, the isolate contains at least 95% of an N-Benzyl-Substituted Pyridyl Porphyrin Compound by weight of the isolate.

The term "is substantially free of its corresponding other isomers" as used herein means has no more than about 10% by weight of its corresponding other isomers; in one embodiment, no more than about 5% by weight, in another embodiment, no more than about 2% by weight, in another embodiment, no more than about 1% by weight, and in another embodiment, no more than about 0.1% by weight of its corresponding other isomers.

The term "OAc" as used herein means acetate; "OTf" means triflate; "OMs" means mesylate; and "OTs" means tosylate.

In the N-Benzyl-Substituted Pyridyl Porphyrin Compounds it is to be understood that the number of positively charged groups and the number of negatively charged groups can vary due to factors including pH.

Examples of positively charged groups within the scope of the invention include $M^+$ when f is 1, and each N-benzyl-substituted pyridyl group (1-4). In some embodiments, the amino acid residue can have a protonated amino group. In these embodiments, each protonated amino group is a positively charged group.

Similarly, in some embodiments, the amino acid residue can have one or more carboxylate groups. In these embodiments, each carboxylate group is a negatively charged group.

It is to be understood that while the N-Benzyl-Substituted Pyridyl Porphyrin Compounds are depicted as having a particular structure in which each of two pyrrole nitrogen atoms forms a bond to the metal M, one of skill in the art will recognize that the pyrrole nitrogen atoms can also form a tetracoordinate species, often depicted as having four equivalent bonds, each between a pyrrole nitrogen atom and the metal M. The depictions of the N-Benzyl-Substituted Pyridyl Porphyrin Compounds set forth herein also encompass the tetracoordinate species.

5.3 Methods for Making the N-benzyl-substituted Pyridyl Porphyrin Compounds

The N-Benzyl-Substituted Pyridyl Porphyrin Compounds can be made using conventional organic synthesis or methods or by the following illustrative methods shown in Schemes 1-3 below.

Scheme 1 below illustrates a procedure that is useful for synthesizing porphyrin intermediate 1, which is useful for making the N-Benzyl-Substituted Pyridyl Porphyrin Compounds.

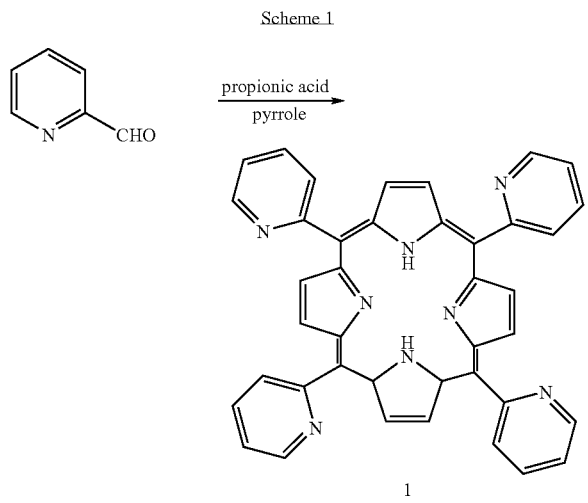

Pyridine-2-carboxaldehyde can be reacted with propionic acid and pyrrole in the presence of about 10% xylene or toluene at a temperature of from about 120° C. to reflux, for example at a temperature in the range of from about 130° C. to about 140° C., to provide the pyridyl porphyrin 1.

Scheme 2, below, illustrates a method useful for making the hydroxymetallo-porphyrin intermediates of Formula (IV), which are useful for making the N-Benzyl-Substituted Pyridyl Porphyrin Compounds wherein f is 1 and M is defined above for the N-Benzyl-Substituted Pyridyl Porphyrin Compounds.

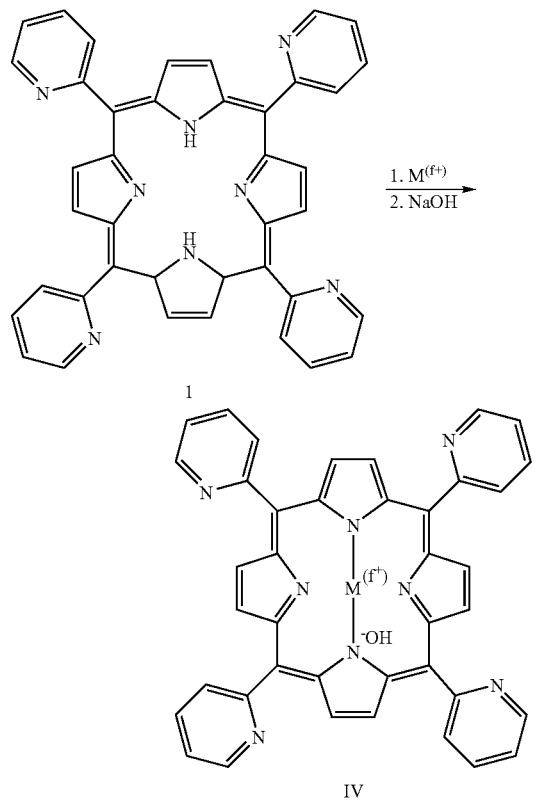

The porphyrin intermediate 1 can be reacted with a metallating agent in refluxing hydrochloric acid to form a metallated porphyrin complex that can be treated at room temperature with a hydroxide base, such as sodium hydroxide or potassium hydroxide, to provide the hydroxy-metallated porphyrin intermediates of Formula (IV). Metallating agents that are useful in the method of Scheme 2 include, but are not limited to, ferrous chloride, ferric chloride, ferric sulfate, ferrous acetate, ferrous ammonium sulfate, manganese(III) acetate, manganese(II) acetate, and manganese(II) chloride.

Scheme 3, below, shows a method for making the N-Benzyl-Substituted Pyridyl Porphyrin Compounds wherein n is 4 or 5; and R, M, and f are as defined above for the N-Benzyl-Substituted Pyridyl Porphyrin Compounds.

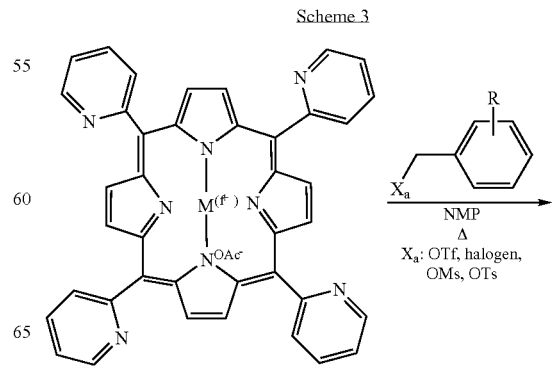

-continued

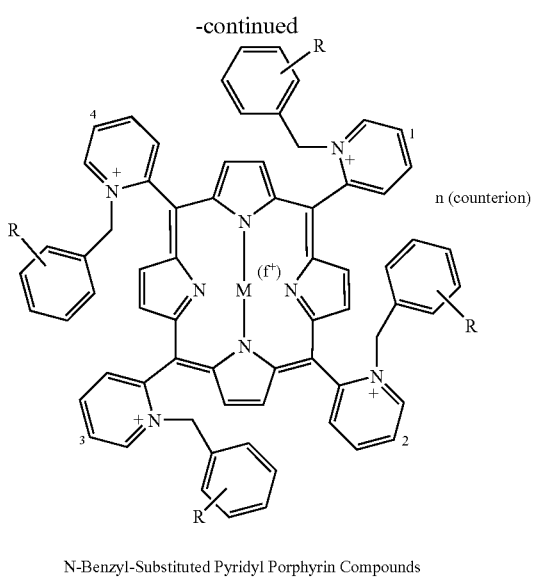

N-Benzyl-Substituted Pyridyl Porphyrin Compounds

The pyridyl groups of the hydroxy-metallated porphyrin intermediates of Compound 3 can be N-benzylated using excess of, for example, an α-bromo benzyl compound in N-methylpyrrolidinone (NMP) at elevated temperature (about 50° C.-130° C.). This method provides N-Benzyl-Substituted Pyridyl Porphyrin Compounds wherein R, M, f, and n are as defined above for the N-Benzyl-Substituted Pyridyl Porphyrin Compounds.

An α-bromo benzyl compound of Scheme 3 can be prepared, for example, by reacting the corresponding bromomethylbenzoic acid chloride or bromomethylbenzenesulfonic acid chloride with an amino acid in the presence of 2,6-lutidine and NMP. Alternatively, an α-bromo benzyl compound of Scheme 3 can be prepared, for example, by reacting the corresponding bromomethylbenzoic acid chloride or bromomethylbenzenesulfonic acid chloride with an amino acid ester, such as ethyl, methyl, or t-butyl ester, optionally as its acid salt, in the presence of 2,6-lutidine and dichloromethane, then converting the ester, e.g., via hydrolysis, to provide the corresponding acid functionality.

Other α-halo benzyl compounds of Scheme 3 can be prepared, for example, from the corresponding α-bromo benzyl compounds. The α-OTf, α-OMs, and α-OTs benzyl compounds of Scheme 3 can be prepared by reacting the corresponding α-OH benzyl compounds with, for example, trifluoromethanesulfonyl chloride, methanesulfonyl chloride, toluenesulfonyl chloride, trifluoromethanesulfonic acid anhydride, methanesulfonic acid anhydride, or toluenesulfonic acid anhydride.

If desired, the N-Benzyl-Substituted Pyridyl Porphyrin Compounds can be purified using methods well-known to one skilled in the art including, but not limited to, flash column chromatography, high-performance liquid chromatograpy (HPLC), medium-pressure liquid chromatography (MPLC), preparative thin-layer chromatograpy, anion-exchange chromatography, and recrystallization.

5.4 Therapeutic Uses of the N-benzyl-substituted Pyridyl Porphyrin Compounds In accordance with the invention, the N-Benzyl-Substituted Pyridyl Porphyrin Compounds can be administered to a subject in need of treatment or prevention of a Condition or prolongation of the half-life of an oxidation-prone compound.

In one embodiment, the N-Benzyl-Substituted Pyridyl Porphyrin Compounds treat or prevent a Condition or to prolong the half-life of an oxidation-prone compound by scavenging or neutralizing one or more reactive species that are generated in vivo due to the interaction of ionizing radiation with a subject's tissue. Such reactive species include, but are not limited to, reactive oxygen species, including superoxides and peroxides; and reactive nitrogen species, including $^-$ONOO, nitric oxide, and nitroxyl species, such as NO$^-$, NOH, or ONO.

5.4.1 Treatment of Prevention of Injury Due to Exposure to a Reactive Species The N-Benzyl-Substituted Pyridyl Porphyrin Compounds can be used to treat or prevent cell or tissue injury due to exposure to a reactive species. In one embodiment, the reactive species is an oxidant or a free radical, including, but not limited to reactive oxygen species, such as superoxides and peroxides, and reactive nitrogen species, such as $^-$ONOO, nitric oxide, and nitroxyl species, such as NO$^-$, NOH, and ONO.

Examples of injury due to exposure to a reactive species are skin wrinkling, skin aging, sunburn erythema, UV-induced skin injury, and UV-induced skin disease, such as cancer.

5.4.2 Prolonging the Half-life of an Oxidation-prone Compound

The N-Benzyl-Substituted Pyridyl Porphyrin Compounds can be used to prolong the half-life of an oxidation-prone compound in vivo. In another embodiment, when an oxidation-prone compound, such as hyaluronic acid, which is useful for treating osteoarthritis, is administered to a subject, an N-Benzyl-Substituted Pyridyl Porphyrin Compound can also be administered to treat or prevent oxidative injury caused by the oxidation-prone compound or to inhibit the degradation and, accordingly, enhance the efficacy of the oxidation-prone compound. In one embodiment, N-Benzyl-Substituted Pyridyl Porphyrin Compounds inhibit the oxidative damage of hyaluronic acid. In another embodiment, the N-Benzyl-Substituted Pyridyl Porphyrin Compounds enhance the efficacy of the oxidation-prone compound.

5.4.3 Treatment or Prevention of Erectile Dysfunction

The N-Benzyl-Substituted Pyridyl Porphyrin Compounds are useful for treating or preventing erectile dysfunction. Erectile dysfunction includes an inability to achieve or maintain a full erection, particularly that which is sufficient to achieve or maintain sexual intercourse. The inability can be a total inability, an inconsistent ability, or a tendency to maintain only a brief erection. Erectile dysfunction that is treatable or preventable according to the methods described herein includes idiopathic erectile dysfunction, as well as that which can result, for example, from trauma, including mechanical trauma, particularly that resulting from surgery, to the nerves (such as during prostatectomy); diabetes mellitus; a cardiovascular disease, including atherosclerosis; radiation; or certain drugs. The erectile dysfunction can also be age-related.

The N-Benzyl-Substituted Pyridyl Porphyrin Compounds can be used to treat or prevent erectile dysfunction caused by surgery. In one embodiment, the surgery is surgery of the prostate or the colon.

In a further embodiment the erectile dysfunction results from prostate nerve injury.

5.4.4 Treatment or Prevention of Urinary Incontinence

The N-Benzyl-Substituted Pyridyl Porphyrin Compounds are also useful for treating or preventing urinary incontinence. Urinary incontinence that is treatable or preventable according to the methods described herein, can result, for example, from trauma, including mechanical trauma, particularly during childbirth or that resulting from surgery, to the nerves (such as during prostatectomy or gynecological surgery); diabetes mellitus; a cardiovascular disease, including atherosclerosis; radiation; or certain drugs. The urinary incontinence can also be age-related.

In one embodiment the subject in need of urinary incontinence treatment or prevention is male.

In one embodiment the subject in need of urinary incontinence treatment or prevention is female.

5.4.5 Treatment or Prevention of Lung Disease

The N-Benzyl-Substituted Pyridyl Porphyrin Compounds can be used to treat or prevent a lung disease. In one embodiment, the lung disease is cystic fibrosis, hyperoxic lung injury, emphysema, or adult respiratory distress syndrome.

5.4.6 Treatment or Prevention of Hyperoxia

The N-Benzyl-Substituted Pyridyl Porphyrin Compounds can be used to treat or prevent injury due to hyperoxia. In one embodiment, the injury due to hyperoxia is hyperoxia-induced eye injury or hyperoxia-induced lung injury.

5.4.7 Treatment or Prevention or Neurodegenerative Disease

The N-Benzyl-Substituted Pyridyl Porphyrin Compounds can be used to treat or prevent a neurodegenerative disease. In one embodiment, the neurodegenerative disease is Parkinson's disease, Alzheimer's disease, Huntington's disease, or amyotrophic lateral sclerosis.

5.4.8 Treatment or Prevention of Liver Disease

The N-Benzyl-Substituted Pyridyl Porphyrin Compounds can be used to treat or prevent a liver disease. In one embodiment, the liver disease is hepatitis, liver failure, or drug-induced liver injury.

5.4.9 Treatment or Prevention of Mycocardial Damage During Cardioplegia

In one embodiment, the invention provides methods for inducing or maintaining cardioplegia comprising administering to a subject in need thereof an effective amount of a cardioplegia-inducing agent and an N-Benzyl-Substituted Pyridyl Porphyrin Compound. Cardioplegia-inducing agents useful in the present invention include, but are not limited to, potassium chloride, procaine, lidocaine, novocaine, bupivocaine, nicorandil, pinacidil, halothane, St. Thomas solution, Fremes solution, 2,3-butanedione monoxime, or esmolol.

In one embodiment, the cardioplegia-inducing agent is lidocaine.

In one embodiment, a cardioplegia-inducing agent and an N-Benzyl-Substituted Pyridyl Porphyrin Compound are present within the same composition. The N-Benzyl-Substituted Pyridyl Porphyrin Compounds are useful for preventing or minimizing myocardial damage from occurring during cardioplegia.

In still another embodiment, the invention provides methods for protecting a subject's heart against myocardial damage during cardioplegia, the method comprising administering to a subject in need thereof an effective amount of: (a) a cardioplegia-inducing agent; and (b) an N-Benzyl-Substituted Pyridyl Porphyrin Compound.

In one embodiment, the cardioplegia-inducing agent is administered prior to the administration of the N-Benzyl-Substituted Pyridyl Porphyrin Compound.

In another embodiment, the N-Benzyl-Substituted Pyridyl Porphyrin Compound is administered prior to the administration of the cardioplegia-inducing agent.

In a further embodiment, the cardioplegia-inducing agent and the N-Benzyl-Substituted Pyridyl Porphyrin Compound are administered concurrently.

In a further embodiment, the cardioplegia-inducing agent and the N-Benzyl-Substituted Pyridyl Porphyrin Compound are present within the same composition.

In another embodiment, the cardioplegia-inducing agent and the N-Benzyl-Substituted Pyridyl Porphyrin Compound are administered such that the N-Benzyl-Substituted Pyridyl Porphyrin Compound exerts its prophylactic effect of protection against myocardial damage while the cardioplegia-inducing agent exerts its cardioplegic effect.

In one embodiment, a invention provides a composition comprising an N-Benzyl-Substituted Pyridyl Porphyrin Compound and a cardioplegia-inducing agent.

5.4.10 Treatment or Prevention of an Inflammatory Condition

The N-Benzyl-Substituted Pyridyl Porphyrin Compounds can be used to treat or prevent an inflammatory condition. Inflammatory conditions can arise where there is an inflammation of the body tissue. Examples of inflammatory conditions that are treatable or preventable using the N-Benzyl-Substituted Pyridyl Porphyrin Compounds include, but are not limited to, transplant rejection; chronic inflammatory disorders of the joints, such as arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome (ARDS), and chronic obstructive airway disease; inflammatory disorders of the eye such as corneal dystrophy, trachoma, onchocerciasis, uveitis, sympathetic ophthalmitis and endophthalmitis; chronic inflammatory disorders of the gum, such as gingivitis and periodontitis; tuberculosis; leprosy; inflammatory diseases of the kidney such as uremic complications, glomerulonephritis and nephrosis; inflammatory disorders of the skin such as sclerodermatitis, psoriasis and eczema; inflammatory diseases of the central nervous system, such as chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases such as diabetes mellitus, immune-complex vasculitis, systemic lupus erythematosus (SLE); inflammatory diseases of the heart such as cardiomyopathy, ischemic heart disease hypercholesterolemia, and atherosclerosis; as well as inflammation resulting from various diseases such as preeclampsia, chronic liver failure, brain and spinal cord trauma, and cancer. The N-Benzyl-Substituted Pyridyl Porphyrin Compounds can also be used to treat or prevent reduce the progression of an inflammatory condition and/or to reduce the symptoms of the inflammatory condition. In one embodiment, the N-Benzyl-Substituted Pyridyl Porphyrin Compounds are useful for treating or preventing pain associated with an inflammatory condition.

The inflammatory condition that is treatable or preventable by administration of an effective amount of an N-Benzyl-Substituted Pyridyl Porphyrin Compound can also be a systemic inflammation of the body. Examples of systemic inflammation include but are not limited to, gram-positive or gram negative shock, sepsis, septic shock, hemorrhagic or anaphylactic shock, (SIRS), or shock induced by cancer chemotherapy in response to a pro-inflammatory cytokine such as IL-2, interferon-γ, or GM-CSF.

In one embodiment, the inflammatory condition is circulatory shock, sepsis, systemic inflammatory response syndrome, hemorrhagic shock, cardiogenic shock, or systemic inflammation induced by an anticancer immunotherapy such as IL-2.

In one embodiment, an N-Benzyl-Substituted Pyridyl Porphyrin Compound can be used to treat or prevent an inflammatory skin disease. In one embodiment, the inflammatory skin disease is contact dermatitis, erythema, or psoriasis.

In one embodiment, the inflammatory condition results from exposure to a reactive species.

5.4.11 Treatment or Prevention of a Reperfusion Injury

A reperfusion injury can be treated or prevented by administration of an effective amount of an N-Benzyl-Substituted Pyridyl Porphyrin Compound. Reperfusion injury can result following a naturally occurring episode, such as a myocardial infarction, stroke, or during a surgical procedure where blood flow in vessels is intentionally or unintentionally blocked.

Reperfusion injuries that can be treated or prevented by administering an effective amount of an N-Benzyl-Substituted Pyridyl Porphyrin Compound include, but are not limited to, intestinal reperfusion injury, stroke, neurotrauma, neuroinjury, myocardial infarction, and reperfusion injury resulting from cardiopulmonary bypass surgery, organ transplantation surgery, thoracoabrominal aneurysm repair surgery, carotid endarerectomy surgery, or hemorrhagic shock.

In one embodiment, the reperfusion injury results from cardiopulmonary bypass surgery, thoracoabrominal aneurysm repair surgery, carotid endarerectomy surgery or hemorrhagic shock.

In one embodiment, an N-Benzyl-Substituted Pyridyl Porphyrin Compound is administered during myocardial reperfusion. In one embodiment, the reperfusion results from cardiopulmonary bypass. In another embodiment, the reperfusion results in a myocardial infarction injury.

In one embodiment, the reperfusion injury is a reoxygenation injury resulting from surgery, particularly organ transplantation surgery.

In one embodiment, the organ transplantation is cardiac transplantation or kidney transplantation.

In another embodiment, the organ transplantation is heart transplantation, kidney transplantation, liver transplantation, or lung transplantation.

In one embodiment, the reperfusion injury that results from exposure to a reactive species.

5.4.12 Treatment or Prevention of an Ischemic Condition

An ischemic condition can be treated or prevented by administration of an effective amount of an N-Benzyl-Substituted Pyridyl Porphyrin Compound.

Ischemic conditions that can be treated or prevented by administering an effective amount of an N-Benzyl-Substituted Pyridyl Porphyrin Compound include, but are not limited to, stable angina, unstable angina, myocardial ischemia, hepatic ischemia, mesenteric artery ischemia, intestinal ischemia, critical limb ischemia, chronic critical limb ischemia, erebral ischemia, acute cardiac ischemia, and an ischemic disease of the central nervous system, such as stroke or cerebral ischemia.

In one embodiment, the ischemic condition is myocardial ischemia, stable angina, unstable angina, stroke, ischemic heart disease or cerebral ischemia.

In one embodiment, the ischemic condition results from exposure to a reactive species.

5.4.13 Treatment or Prevention or a Cardiovascular Disease

A cardiovascular disease can be treated or prevented by administration of an effective amount of an N-Benzyl-Substituted Pyridyl Porphyrin Compound.

Cardiovascular diseases that can be treated or prevented by administering an effective amount of an N-Benzyl-Substituted Pyridyl Porphyrin Compound include, but are not limited to, chronic heart failure, atherosclerosis, congestive heart failure, circulatory shock, cardiomyopathy, cardiac transplant, myocardial infarction, and a cardiac arrhythmia, such as atrial fibrillation, supraventricular tachycardia, atrial flutter, and paroxysmal atrial tachycardia.

In one embodiment, the cardiovascular disease is a cardiac arrhythmia, congestive heart failure, circulatory shock or cardiomyopathy.

In another embodiment, the cardiac arrhythmia is atrial fibrillation, supraventricular tachycardia, atrial flutter or paroxysmal atrial tachycardia.

In one embodiment, the cardiovascular disease is heart failure.

In another embodiment, the cardiovascular disease is balloon-induced vascular injury, coronary stenting, atherosclerosis, or restenosis.

In another embodiment, the cardiovascular disease is acute heart failure, chronic heart failure, ischemic heart failure, drug-induced heart failure, idiopathic heart failure, alcoholic heart failure, or cardiac arrhythmia.

In one embodiment, the cardiovascular disease results from exposure to a reactive species.

5.4.14 Treatment or Prevention of Diabetes or a Diabetic Complication

Diabetes or a diabetic complication can be treated or prevented by administration of an effective amount of an N-Benzyl-Substituted Pyridyl Porphyrin Compound.

Types of diabetes that can be treated or prevented by administering an effective amount of an N-Benzyl-Substituted Pyridyl Porphyrin Compound include, but are not limited to, Type I diabetes (Insulin Dependent Diabetes Mellitus), Type II diabetes (Non-Insulin Dependent Diabetes Mellitus), gestational diabetes, an insulinopathy, diabetes resulting from pancreatic disease, diabetes resulting from another endocrine disease (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by β-cell toxins.

The N-Benzyl-Substituted Pyridyl Porphyrin Compounds can also be used to treat or prevent a diabetic complication. Examples of diabetic complications that are treatable or preventable by administering an effective amount of an N-Benzyl-Substituted Pyridyl Porphyrin Compound include, but are not limited to, diabetic cataract, glaucoma, retinopathy, nephropathy (such as microaluminuria and progressive diabetic nephropathy), polyneuropathy, gangrene of the feet, atherosclerotic coronary arterial disease, peripheral arterial disease, nonketotic hyperglycemic-hyperosmolar coma, mononeuropathy, autonomic neuropathy, a skin or mucous membrane complication (such as an infection, a shin spot, a candidal infection or necrobiosis lipoidica diabeticorumobesity), a peripheral vascular disesase, hyperlipidemia, hypertension, syndrome of insulin resistance, coronary artery disease, diabetic neuropathy, mononeuropathy, a foot ulcer, a joint disease, a fungal infection, a bacterial infection, neuropathy, angiopathy, cardiomyopathy, and erectile dysfunction.

5.4.15 Treatment or Prevention of a Side Effect of Cancer Chemotherapy

A side effect of cancer chemotherapy can be treated or prevented by administration of an effective amount of an N-Benzyl-Substituted Pyridyl Porphyrin Compound.

Examples of a side effect of cancer chemotherapy include, but are not limited to, nausea, vomiting, alopecia, myelosuppression, anorexia, neuropathy, headache, pain, dry mouth, mouth sores, bone marrow suppression, hyperpigmentation, skin rash, fluid retention, diarrhea, cardiotoxicity, anaphylaxis, fever and chills, leucopenia, thrombocytopenia, lethargy, nephrotoxicity, ototoxicity, hot flashes, hyperglycemia, and pancreatitis.

In one embodiment, the cancer chemotherapy comprises administering a platinum-based antitumor agent. Accordingly, the present invention encompasses methods for treating or preventing a side effect resulting from administration of a platinum-based antitumor agent, comprising administering to a subject in need thereof an effective amount of an N-Benzyl-Substituted Pyridyl Porphyrin Compound. Side effects resulting from administration of a platinum-based antitumor agent are those side effects of cancer chemotherapy listed above. In certain embodiments, platinum-based antitumor agents include, but are not limited to, cisplatin, carboplatin, aroplatin, and oxaliplatin.

In one embodiment, the cancer chemotherapy comprises admininstering doxorubicin or cisplatin.

In a specific embodiment, an N-Benzyl-Substituted Pyridyl Porphyrin Compound is administered to a subject in need of treatment or prevention of a side effect of doxorubicin.

In another specific embodiment, an N-Benzyl-Substituted Pyridyl Porphyrin Compound is administered to a subject in need of treatment or prevention of a side effect of cisplatin.

5.4.16 Treatment or Prevention of a Radiation-induced Injury

A radiation-induced injury can be treated or prevented by administration of an effective amount of an N-Benzyl-Substituted Pyridyl Porphyrin Compound to a subject.

Examples of a radiation-induced injury that is treatable or preventable using the present methods include, but are not limited to, an acute radiation syndrome, such as a cerebral syndrome; a gastrointestinal syndrome; a hematopoietic syndrome; acute radiation sickness; pulmonary fibrosis; radiation proctitis; neuropathy; nausea; vomiting; alopecia; pain; headache; esophageal stricture; gastric ulcer; radiation pneumonitis; cardiomyopathy; photodamaged skin, which is characterized by locally exaggerated pigmentation, looseness, fine lines, wrinkles, enlarged pores, and the development of darkened plugs in the sebaceous glands; skin cancer; sunburn; solar dermatitis; photoallergic dermnatitis; sun spots; age spots; and sun poisoning.

In one embodiment, treating a radiation-induced injury includes increasing a subject's survival time following exposure to radiation.

In another embodiment, death is an example of a radiation-induced injury that is preventable according to the present invention.

The N-Benzyl-Substituted Pyridyl Porphyrin Compounds are also useful for protecting bystander healthy tissue from a radiation-induced injury during administration of therapeutic radiation.

A radiation-induced injury may result from exposure of a subject to ionizing radiation from numerous sources including, but not limited to, a nuclear weapon, such as an atomic bomb, a neutron bomb, or a "dirty bomb;" an industrial source, such as a nuclear power plant, a nuclear submarine, or a nuclear waste disposal site; a diagnostic or therapeutic medical or dental application, such as x-rays, CT scans, external radiation therapy, internal radiation therapy (e.g., radioactive "seed" implants used in cancer therapy). The injury might result from an accident, an act of war or terrorism, cumulative exposure at the home or workplace, purposeful exposure during medical diagnosis or treatment, or exposure to ultraviolet radiation, such as from sunlight.

Examples of a radiation-induced injury caused by exposure to sunlight include, but are not limited to photodamaged skin, which is characterized by locally exaggerated pigmentation, looseness, fine lines, wrinkles, enlarged pores, and the development of darkened plugs in the sebacious glands; skin cancer; sunburn; solar dermatitis; photoallergic dermatitis; sun spots; age spots; and sun poisoning. In one embodiment, a subject being treated for a radiation-induced injury caused by exposure to sunlight has been sensitized to sunlight by a disease or by medication (drug-induced sensitivity).

In one embodiment, the injury is induced by radiation from a nuclear weapon.

In another embodiment, the injury is induced by radiation from a nuclear power plant.

In still another embodiment, the injury is induced by radiation from radiation therapy that the subject is receiving for the treatment of a non-radiation related disorder.

In still another embodiment, the injury is induced by radiation from radiation therapy that the subject is receiving for the treatment of cancer.

In one embodiment, the injury is induced by radiation from a radioactive material that is exposed or administered to a subject.

In one embodiment, the radiation-induced injury results from exposure to a reactive species.

5.4.17 Treatment or Prevention of Cancer

The invention encompasses methods for treating or preventing cancer, comprising administering to a subject in need thereof an effective amount of an N-Benzyl-Substituted Pyridyl Porphyrin Compound.

Examples of cancers that are treatable or preventable using the N-Benzyl-Substituted Pyridyl Porphyrin Compounds include, but are not limited to, the cancers disclosed below in Table 1 and metastases thereof.

TABLE 1

Solid tumors, including but not limited to:

fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon cancer
colorectal cancer
kidney cancer
pancreatic cancer
bone cancer
breast cancer
ovarian cancer
prostate cancer
esophageal cancer
stomach cancer
oral cancer
nasal cancer
throat cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma
glioma
glioblastoma multiforme
astrocytoma
medulloblastoma
craniopharyngioma
ependymoma
pinealoma
hemangioblastoma TABLE 1-continued acoustic neuroma
oligodendroglioma
meningioma
skin cancer
melanoma
neuroblastoma
retinoblastoma blood-borne cancers, including but not limited to:

acute lymphoblastic leukemia ("ALL")
acute lymphoblastic B-cell leukemia
acute lymphoblastic T-cell leukemia
acute myeloblastic leukemia ("AML")
acute promyelocytic leukemia ("APL")
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia ("CML")
chronic lymphocytic leukemia ("CLL")
hairy cell leukemia
multiple myeloma acute and chronic leukemias:

lymphoblastic
myelogenous
lymphocytic
myelocytic leukemias

Lymphomas:

Hodgkin's disease
non-Hodgkin's Lymphoma
Multiple myeloma
Waldenström's macroglobulinemia
Heavy chain disease
Polycythemia vera In one embodiment, the cancer is pancreatic cancer, colorectal cancer, mesothelioma, a malignant pleural effusion, peritoneal carcinomatosis, peritoneal sarcomatosis, renal cell carcinoma, small cell lung cancer, non-small cell lung cancer, testicular cancer, bladder cancer, breast cancer, head and neck cancer, or ovarian cancer.

In still another embodiment, the subject in need of treatment or prevention has previously undergone treatment for cancer. Such previous treatments include, but are not limited to, prior chemotherapy, radiation therapy, surgery or immunotherapy, such as cancer vaccines.

The N-Benzyl-Substituted Pyridyl Porphyrin Compounds are also useful for the treatment or prevention of a cancer caused by a virus. For example, human papilloma virus can lead to cervical cancer (see, e.g., Hernandez-Avila et al., Archives of Medical Research (1997) 28:265-271), Epstein-Barr virus (EBV) can lead to lymphoma (see, e.g., Herrmann et al., J Pathol (2003) 199(2):140-5), hepatitis B or C virus can lead to liver carcinoma (see, e.g., El-Serag, J Clin Gastroenterol (2002) 35(5 Suppl 2):S72-8), human T cell leukemia virus (HTLV)-J can lead to T-cell leukemia (see e.g., Mortreux et al., Leukemia (2003) 17(1):26-38), human herpesvirus-8 infection can lead to Kaposi's sarcoma (see, e.g., Kadow et al., Curr Opin Investig Drugs (2002) 3(11):1574-9), and Human Immune deficiency Virus (HIV) infection contribute to cancer development as a consequence of immunodeficiency (see, e.g., Dal Maso et al., Lancet Oncol (2003) 4(2):110-9).

The N-Benzyl-Substituted Pyridyl Porphyrin Compounds can also be administered to prevent the progression of a cancer, including but not limited to the cancers listed in Table 1. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 68-79 (2d ed. 1976). Hyperplasia is a form of controlled cell proliferation involving an increase in cell number in a tissue or organ, without significant alteration in structure or function. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of an N-Benzyl-Substituted Pyridyl Porphyrin Compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions that can be treated or prevented according to the present invention.

In another embodiment, fibrocystic disease (e.g., cystic hyperplasia, mammary dysplasia, particularly adenosis (benign epithelial hyperplasia)) can be treated or prevented according to the present invention.

In other embodiments, cancer in a subject who exhibits one or more of the following predisposing factors for malignancy can be treated by administration of an effective amount of an N-Benzyl-Substituted Pyridyl Porphyrin Compound: a chromosomal translocation associated with a malignancy, e.g., the Philadelphia chromosome for chronic myelogenous leukemia or t(14;18) for follicular lymphoma; familial polyposis or Gardner's syndrome; benign monoclonal gammopathy; a first degree kinship with persons having a cancer or precancerous disease showing a Mendelian (genetic) inheritance pattern, e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome (see Robbins and Angell, Basic Pathology, 112-112 (2d ed. 1976); and exposure to carcinogens, e.g., smoking, and inhalation of or contacting with certain chemicals.

In another specific embodiment, the N-Benzyl-Substituted Pyridyl Porphyrin Compounds are administered to a human subject to prevent progression to breast, colon, ovarian, or cervical cancer.

5.5 Therapeutic/Prophylactic Administration and Compositions of the Invention Due to their activity, the N-Benzyl-Substituted Pyridyl Porphyrin Compounds are advantageously useful in veterinary and human medicine. As described above, the N-Benzyl-Substituted Pyridyl Porphyrin Compounds are useful for treating or preventing a Condition or for prolonging the half-life of an oxidation-prone compound in a subject in need thereof.

When administered to a subject, the N-Benzyl-Substituted Pyridyl Porphyrin Compounds can be administered as a component of a composition that comprises a physiologically acceptable carrier or vehicle. The present compositions, which comprise an N-Benzyl-Substituted Pyridyl Porphyrin Compound, can be administered orally. The N-Benzyl-Substituted Pyridyl Porphyrin Compounds can also be administered by any other convenient route, for example, by infusion or bolus injection, by absorption through epithelial or mucocutaneous linings (e.g., oral, rectal, and intestinal mucosa) and can be administered together with another biologically active agent. Administration can be systemic or local. Various delivery systems are known, e.g., encapsulation in liposomes, microparticles, microcapsules, capsules, and can be administered.

Methods of administration include, but are not limited to, intradermal, intramuscular, intraperitoneal, intravenous, ocular, subcutaneous, intranasal, epidural, oral, sublingual, intracerebral, intravaginal, transdermal, rectal, by inhalation, or topical, particularly to the ears, nose, eyes, or skin. In some instances, administration will result in the release of the N-Benzyl-Substituted Pyridyl Porphyrin Compounds into the bloodstream. The mode of administration can be left to the discretion of the practitioner.

In one embodiment, the N-Benzyl-Substituted Pyridyl Porphyrin Compounds are administered orally.

In other embodiments, it can be desirable to administer the N-Benzyl-Substituted Pyridyl Porphyrin Compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the N-Benzyl-Substituted Pyridyl Porphyrin Compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon oar, synthetic pulmonary surfactant. In certain embodiments, the N-Benzyl-Substituted Pyridyl Porphyrin Compounds can be formulated as a suppository, with traditional binders and excipients such as triglycerides.

In another embodiment the N-Benzyl-Substituted Pyridyl Porphyrin Compounds can be delivered in a vesicle, in particular a liposome (see Langer, *Science* 249:1527-1533 (1990) and Treat or prevent et al., *Liposomes in the Therapy of Infectious Disease and Cancer* 317-327 and 353-365 (1989)).

In yet another embodiment the N-Benzyl-Substituted Pyridyl Porphyrin Compounds can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-1533 (1990) can be used. In one embodiment a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

In yet another embodiment a controlled- or sustained-release system can be placed in proximity of a target of the N-Benzyl-Substituted Pyridyl Porphyrin Compounds, e.g., the spinal column, brain, skin, lung, thyroid gland, colon or gastrointestinal tract, thus requiring only a fraction of the systemic dose.

The present compositions can optionally comprise a suitable amount of a pharmaceutically acceptable excipient so as to provide the form for proper administration to the subject.

Such pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment the pharmaceutically acceptable excipients are sterile when administered to a subject. Water is a particularly useful excipient when the N-Benzyl-Substituted Pyridyl Porphyrin Compounds is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment the composition is in the form of a capsule (see e.g. U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

In one embodiment the N-Benzyl-Substituted Pyridyl Porphyrin Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving an N-Benzyl-Substituted Pyridyl Porphyrin Compound are also suitable for orally administered compositions. In these latter platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In another embodiment the N-Benzyl-Substituted Pyridyl Porphyrin Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized-powder or water free concentrate in a hermetically sealed container such as an ampule or sachette indicating the quantity of active agent. Where the N-Benzyl-Substituted Pyridyl Porphyrin Compounds are to be administered by infusion, they can be dispensed, for example, with an infusion bottle containing sterile pharmaceutical grade water or saline. Where the N-Benzyl-Substituted Pyridyl Porphyrin Compounds are administered by injection, an ampule of sterile water for injection or saline can be provided so that the ingredients can be mixed prior to administration.

The N-Benzyl-Substituted Pyridyl Porphyrin Compounds can be administered by controlled-release or sustained-release means or by delivery devices that are well known to those skilled in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of an N-Benzyl-Substituted Pyridyl Porphyrin Compound to treat or prevent the Condition or to prolong the half-life of an oxidation-prone compound in a minimal amount of time. Advantages of controlled- or sustained-release compositions include extended activity of the drug, reduced dosage frequency, and increased subject compliance. In addition, controlled- or sustained-release compositions can favorably affect the time of onset of action or other characteristics, such as blood levels of the N-Benzyl-Substituted Pyridyl Porphyrin Compound, and can thus reduce the occurrence of adverse side effects.

Controlled- or sustained-release compositions can initially release an amount of an N-Benzyl-Substituted Pyridyl Porphyrin Compound that promptly produces the desired therapeutic or prophylactic effect, and gradually and continually release other amounts of the N-Benzyl-Substituted Pyridyl Porphyrin Compound to maintain this level of therapeutic or prophylactic effect over an extended period of time. To maintain a constant level of the N-Benzyl-Substituted Pyridyl Porphyrin Compound in the body, the N-Benzyl-Substituted Pyridyl Porphyrin Compound can be released from the dosage form at a rate that will replace the amount of N-Benzyl-Substituted Pyridyl Porphyrin Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the N-Benzyl-Substituted Pyridyl Porphyrin Compound that is effective in the treatment or prevention of a Condition or prolongation of the half-life of an oxidation-prone compound can be determined by standard clinical techniques. In addition, in vitro or in vivo assays can optionally be employed to help identify optimal dosage ranges. The precise dose to be employed can also depend on the route of administration, the time of the subject's exposure to radiation, the amount of radiation that a subject is exposed to, or the severity of the Condition being prevented or treated. Suitable effective dosage amounts, however, range from about 10 micrograms to about 5 grams about every 4 h, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0g, about 4.2 g, about 4.4 g, about 4.6 g, about 4.8 g, and about 5.0 g, every 4 hours. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered; that is, if more than one N-Benzyl-Substituted Pyridyl Porphyrin Compounds is administered, the effective dosage amounts correspond to the total amount administered.

When the N-Benzyl-Substituted Pyridyl Porphyrin Compounds are administered for prevention of a radiation-inducted therapy injury, the N-Benzyl-Substituted Pyridyl Porphyrin Compound can be administered 48 hours or less time prior to exposure to radiation. Administration cab be repeated at regular intervals as set forth above.

In one embodiment, an intial dose of an N-Benzyl-Substituted Pyridyl Porphyrin Compound is administered from about 5 minutes to about one hour prior to exposure to radiation with repeated doses optionally administered at regular intervals thereafter.

The N-Benzyl-Substituted Pyridyl Porphyrin Compounds can be assayed in vitro or in vivo for the desired therapeutic or prophylactic activity prior to use in humans.

The present methods for treating or preventing a Condition or for prolonging the half-life of an oxidation-prone compound in a subject in need thereof can further comprise administering another therapeutic agent to the subject being administered an N-Benzyl-Substituted Pyridyl Porphyrin Compound. In one embodiment the other therapeutic agent is administered in an effective amount.

Effective amounts of the other therapeutic agents are well known to those skilled in the art. However, it is well within the skilled artisan's purview to determine the other therapeutic agent's optimal effective amount range. In one embodiment of the invention, where-another therapeutic agent is administered to a subject, the effective amount of the N-Benzyl-Substituted Pyridyl Porphyrin Compound is less than its effective amount would be where the other therapeutic agent is not administered. In this case, without being bound by theory, it is believed that the N-Benzyl-Substituted Pyridyl Porphyrin Compounds and the other therapeutic agent act synergistically to treat or prevent a Condition or for prolonging the half-life of an oxidation-prone compound.

The other therapeutic agent can be an anti-inflammatory agent. Examples of useful anti-inflammatory agents include, but are not limited to, adrenocorticosteroids, such as cortisol, cortisone, fludrocortisone, prednisone, prednisolone, 6a-methylprednisolone, triamcinolone, betamethasone, and dexamethasone; and non-steroidal anti-inflammatory agents (NSAIDs), such as aspirin, acetaminophen, indomethacin, sulindac, tolmetin, diclofenac, ketorolac, ibuprofen, naproxen, flurbiprofen, ketoprofen, fenoprofen, oxaprozin, mefenamic acid, meclofenamic acid, piroxicam, meloxicam, nabumetone, rofecoxib, celecoxib, etodolac, and nimesulide.

The other therapeutic agent can be an anti-diabetic agent. Examples of useful anti-diabetic agents include, but are not limited to, glucagons; somatostatin; diazoxide; sulfonylureas, such as tolbutamide, acetohexamide, tolazamide, chloropropamide, glybenclamide, glipizide, gliclazide, and glimepiride; insulin secretagogues, such as repaglinide, and nateglinide; biguanides, such as metformin and phenformin; thiazolidinediones, such as pioglitazone, rosiglitazone, and troglitazone; and α-glucosidase inhibitors, such as acarbose and miglitol.

The other therapeutic agent can be an anti-cardiovascular disease agent. Examples of useful anti-cardiovascular disease agents include, but are not limited to, carnitine; thiamine; and muscarinic receptor antagonists, such as atropine, scopolamine, homatropine, tropicamide, pirenzipine, ipratropium, tiotropium, and tolterodine.

The other therapeutic agent can be an immunosuppressive agent. Examples of useful immunosuppressive agents include a corticosteroid, a calcineurin inhibitor, an antiproliferative agent, a monoclonal antilymphocyte antibody, a polyclonal antilymphocyte antibody, prednisone, methylprednisolone, cyclosporine, tacrolimus, mycophenolate mofetil, azathioprine, sirolimus, muromonab-CD3, interleukin-2 receptor antagonist, daclizumab, antithymocyte globulin-equine, and antithymocyte globulin-rabbit. In one embodiment, the methods for treating or preventing a reoxygenation injury resulting from organ transplantation further comprises administering an immunosuppressive agent.

The other therapeutic agent can be an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinol, thiethylperazine, thioproperazine, tropisetron, and mixtures thereof.

The other therapeutic agent can be an anticancer agent. The N-Benzyl-Substituted Pyridyl Porphyrin Compound and the other anticancer agent can act additively or synergistically. A synergistic use of an N-Benzyl-Substituted Pyridyl Porphyrin Compound and another anticancer agent allows the use of lower dosages of one or more of these agents and/or less frequent administration of the agents to a subject with cancer. The ability to utilize lower dosages of an N-Benzyl-Substituted Pyridyl Porphyrin Compound and/or additional anticancer agents and/or to administer the agents less frequently can reduce the toxicity associated with the administration of the agents to a subject without reducing the efficacy of the agents in the treatment of cancer. In addition, a synergistic effect can result in the improved efficacy of these agents in the treatment of cancer and/or the reduction of adverse or unwanted side effects associated with the use of either agent alone.

In one embodiment, the N-Benzyl-Substituted Pyridyl Porphyrin Compound and the anticancer agent can act synergistically when administered in doses typically employed when such agents are used as monotherapy for the treatment of cancer. In another embodiment, the N-Benzyl-Substituted Pyridyl Porphyrin Compound and the anticancer agent can act synergistically when administered in doses that are less than doses typically employed when such agents are used as monotherapy for the treatment of cancer.

In one embodiment, the additional anticancer agent can be, but is not limited to, a drug listed in Table 2.

TABLE 2

| Alkylating agents | |
|---|---|
| Nitrogen mustards: | Cyclophosphamide |
| | Ifosfamide |
| | Trofosfamide |
| | Chlorambucil |
| Nitrosoureas: | Carmustine (BCNU) |
| | Lomustine (CCNU) |
| Alkylsulphonates: | Busulfan |
| | Treosulfan |
| Triazenes: | Dacarbazine |
| | Procarbazine |
| | Temozolomide |
| Platinum containing complexes: | Cisplatin |
| | Carboplatin |
| | Aroplatin |
| | Oxaliplatin |
| Plant Alkaloids | |
| Vinca alkaloids: | Vincristine |
| | Vinblastine |
| | Vindesine |
| | Vinorelbine |
| Taxoids: | Paclitaxel |
| | Docetaxel |

TABLE 2-continued

| DNA Topoisomerase Inhibitors | |
|---|---|
| Epipodophyllins: | Etoposide |
| | Teniposide |
| | Topotecan |
| | 9-aminocamptothecin |
| | Camptothecin |
| | Crisnatol |
| Mitomycins: | Mitomycin C |
| | Anti-metabolites |
| Anti-folates: | |
| DHFR inhibitors: | Methotrexate |
| | Trimetrexate |
| IMP dehydrogenase Inhibitors: | Mycophenolic acid |
| | Tiazofurin |
| | Ribavirin |
| | EICAR |
| Ribonuclotide reductase Inhibitors: | Hydroxyurea |
| | Deferoxamine |
| Pyrimidine analogs: | |
| Uracil analogs: | 5-Fluorouracil |
| | Fluoxuridine |
| | Doxifluridine |
| | Ralitrexed |
| Cytosine analogs: | Cytarabine (ara C) |
| | Cytosine arabinoside |
| | Fludarabine |
| | Gemcitabine |
| | Capecitabine |
| Purine analogs: | Mercaptopurine |
| | Thioguanine |
| DNA Antimetabolites: | 3-HP |
| | 2'-deoxy-5-fluorouridine |
| | 5-HP |
| | Alpha-TGDR |
| | aphidicolin glycinate |
| | ara-C |
| | 5-aza-2'-deoxycytidine |
| | beta-TGDR |
| | cyclocytidine |
| | guanazole |
| | inosine glycodialdehyde |
| | macebecin II |
| | Pyrazoloimidazole |
| Hormonal therapies: Receptor antagonists: | |
| Anti-estrogen: | Tamoxifen |
| | Raloxifene |
| | Megestrol |
| LHRH agonists: | Goserelin |
| | Leuprolide acetate |
| Anti-androgens: | Flutamide |
| | Bicalutamide |
| Retinoids/Deltoids | |
| | Cis-retinoic acid |
| Vitamin A derivative: | All-trans retinoic acid (ATRA-IV) |
| Vitamin D3 analogs: | EB 1089 |
| | CB 1093 |
| | KH 1060 |
| Photodynamic therapies: | Vertoporfin (BPD-MA) |
| | Phthalocyanine |
| | Photosensitizer Pc4 |
| | Demethoxy-hypocrellin A |
| | (2BA-2-DMHA) |
| Cytokines: | Interferon-α |
| | Interferon-β |
| | Interferon-γ |
| | Tumor necrosis factor |
| Angiogenesis Inhibitors: | Angiostatin (plasminogen fragment) |
| | antiangiogenic antithrombin III |
| | Angiozyme |
| | ABT-627 |
| | Bay 12-9566 |

TABLE 2-continued

|  |  |
|---|---|
|  | Benefin |
|  | Bevacizumab |
|  | BMS-275291 |
|  | cartilage-derived inhibitor (CDI) |
|  | CAI |
|  | CD59 complement fragment |
|  | CEP-7055 |
|  | Col 3 |
|  | Combretastatin A-4 |
|  | Endostatin (collagen XVIII fragment) |
|  | Fibronectin fragment |
|  | Gro-beta |
|  | Halofuginone |
|  | Heparinases |
|  | Heparin hexasaccharide fragment |
|  | HMV833 |
|  | Human chorionic gonadotropin (hCG) |
|  | IM-862 |
|  | Interferon alpha/beta/gamma |
|  | Interferon inducible protein (IP-10) |
|  | Interleukin-12 |
|  | Kringle 5 (plasminogen fragment) |
|  | Marimastat |
|  | Metalloproteinase inhibitors (TIMPs) |
|  | 2-Methoxyestradiol |
|  | MMI 270 (CGS 27023A) |
|  | MoAb IMC-1C11 |
|  | Neovastat |
|  | NM-3 |
|  | Panzem |
|  | PI-88 |
|  | Placental ribonuclease inhibitor |
|  | Plasminogen activator inhibitor |
|  | Platelet factor-4 (PF4) |
|  | Prinomastat |
|  | Prolactin 16 kD fragment |
|  | Proliferin-related protein (PRP) |
|  | PTK 787/ZK 222594 |
|  | Retinoids |
|  | Solimastat |
|  | Squalamine |
|  | SS 3304 |
|  | SU 5416 |
|  | SU6668 |
|  | SU11248 |
|  | Tetrahydrocortisol-S |
|  | Tetrathiomolybdate |
|  | Thalidomide |
|  | Thrombospondin-1 (TSP-1) |
|  | TNP-470 |
|  | Transforming growth factor-beta (TGF-β) |
|  | Vasculostatin |
|  | Vasostatin (calreticulin fragment) |
|  | ZD6126 |
|  | ZD 6474 |
|  | farnesyl transferase inhibitors (FTI) |
|  | Bisphosphonates |
| Antimitotic agents: | Allocolchicine |
|  | Halichondrin B |
|  | Colchicine |
|  | colchicine derivative |
|  | dolstatin 10 |
|  | Maytansine |
|  | Rhizoxin |
|  | Thiocolchicine |
|  | trityl cysteine |
| Others: |  |
| Isoprenylation inhibitors: |  |
| Dopaminergic neurotoxins: | 1-methyl-4-phenylpyridinium ion |
| Cell cycle inhibitors: | Staurosporine |
| Actinomycins: | Actinomycin D |
|  | Dactinomycin |

TABLE 2-continued

|  |  |
|---|---|
| Bleomycins: | Bleomycin A2 |
|  | Bleomycin B2 |
|  | Peplomycin |
| Anthracyclines: | Daunorubicin |
|  | Doxorubicin (adriamycin) |
|  | Idarubicin |
|  | Epirubicin |
|  | Pirarubicin |
|  | Zorubicin |
|  | Mitoxantrone |
| MDR inhibitors: | Verapamil |
| $Ca^{2+}$ ATPase inhibitors: | Thapsigargin |

Other additional anticancer agents that can be used in the compositions and methods of the present invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate, duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine hydrochloride; hydroxyurea; idarubicin hydrochloride; ifosfamide; ilmofosine; interleukin-2 (including recombinant interleukin-2, or rIL2), interferon alfa-2α; interferon alfa-2β; interferon alfa-n1; interferon alfa-n3; interferon beta-Iα; interferon gamma-Iβ; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride;

uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Further anticancer drugs that can be used in the methods and compositions of the invention include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta Lactam Derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene Analogues; clotrimazole; collismycin A; collismycin B; combretastatin A4; combretastatin Analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-acytidine; dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine Analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine Analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin Analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agents; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel Analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin;

vinorelbine; vinxaltine; vitaxin; vorozole; zanoterone; zeniplatin; zilascorb; and zinostatin stimalamer.

In one another embodiment, the other anticancer agent is interferon-α.

In another embodiment, the other anticancer agent is interleukin-2.

In one embodiment, the other anticancer agent is an alkylating agent, such as a nitrogen mustard, a nitrosourea, an alkylsulfonate, a triazene, or a platinum-containing agent.

In one embodiment, the other anticancer agent is a triazene alkylating agent.

In a specific embodiment, the other anticancer agent is temozolomide.

Temozolomide can be administered to a subject at dosages ranging from about 60 mg/m$^2$ (of a subject's body surface area) to about 250 mg/m$^2$ and from about 100 mg/m$^2$ to about 200 mg/m$^2$. In specific embodiments, the dosages of temozolomide are about 10 mg/m$^2$, about 1 mg/m$^2$, about 5 mg/m$^2$, about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 210 mg/m$^2$, about 220 mg/m$^2$, about 230 mg/m$^2$, about 240 mg/m$^2$, or about 250 mg/m$^2$.

In a particular embodiment, temozolomide is administered orally.

In one embodiment, temozolomide is administered orally to a subject at a dose ranging from about 150 mg/m$^2$ to about 200 mg/m$^2$.

In another embodiment, temozolomide is administered orally to a subject once per day for five consecutive days at a dose ranging from about 150 mg/m$^2$ to about 200 mg/m$^2$.

In a specific embodiment, temozolomide is administered orally to a subject once per day for five consecutive days at a dose ranging from about 150 mg/m$^2$ to about 200 mg/m$^2$ on days 1-5, then again orally once per day for five consecutive days on days 28-32 at a dose ranging from about 150 mg/m$^2$ to about 200 mg/m$^2$, then again orally once per day for five consecutive days on days 55-59 at a dose ranging from about 150 mg/m$^2$ to about 200 mg/m$^2$.

In a specific embodiment, the other anticancer agent is procarbazine.

Procarbazine can be administered to a subject at dosages ranging from about 50 mg/m$^2$ (of a subject's body surface area) to about 100 mg/m$^2$ and from about 60 mg/m$^2$ to about 100 mg/m$^2$. In specific embodiments, the dosages of procarbazine are about 10 mg/m$^2$, about 1 mg/m$^2$, about 5 mg/m$^2$, about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m, about 150 mg/m$^2$, about 160 mg/m$^2$, about 170 mg/m$^2$, about 180 mg/m$^2$, about 190 mg/m$^2$, about 200 mg/m$^2$, about 210 mg/m$^2$, about 220 mg/m$^2$, about 230 mg/m$^2$, about 240 mg/m$^2$, about 250 mg/m$^2$, about 260 mg/m$^2$, about 270 mg/m$^2$, about 280 mg/m$^2$, about 290 mg/m$^2$, about 300 mg/m$^2$, about 310 mg/m$^2$, about 320 mg/m$^2$, about 330 mg/m$^2$, about 340 mg/m$^2$, about 350 mg/m$^2$, about 360 mg/m$^2$, about 370 mg/m$^2$, about 380 mg/m$^2$, about 390 mg/m$^2$, about 400 mg/m$^2$, about 410 mg/m$^2$, about 420 mg/m$^2$, about 430 mg/m$^2$, about 440 mg/m$^2$, about 450 mg/m$^2$, about 460 mg/m$^2$, about 470 mg/m$^2$, about 480 mg/m$^2$, about 490 mg/m$^2$, or about 500 mg/m$^2$.

In a particular embodiment, procarbazine is administered intravenously.

In one embodiment, procarbazine is administered intravenously to a subject at a dose raining from about 50 mg/m$^2$ to about 100 mg/m$^2$.

In another embodiment, procarbazine is administered intravenously to a subject once per day for five consecutive days at a dose ranging from about 50 mg/m$^2$ to about 100 mg/m$^2$.

In a specific embodiment, procarbazine is administered intravenously to a subject once per day for five consecutive days at a dose ranging from about 50 mg/m$^2$ to about 100 mg/m$^2$ on days 1-5, then again intravenously once per day for five consecutive days on days 28-32 at a dose ranging from about 50 mg/m$^2$ to about 100 mg/m$^2$, then again intravenously once per day for five consecutive days on days 55-59 at a dose ranging from about 50 mg/m$^2$ to about 100 mg/m$^2$.

In another embodiment, procarbazine is administered once intravenously to a subject at a dose ranging from about 50 mg/m$^2$ to about 100 mg/m$^2$.

In a specific embodiment, the other anticancer agent is dacarbazine.

Dacarbazine can be administered to a subject at dosages ranging from about 60 mg/m$^2$ (of a subject's body surface area) to about 250 mg/m$^2$ and from about 150 mg/m$^2$ to about 250 mg/m$^2$. In specific embodiments, the dosages of dacarbazine are about 10 mg/m$^2$, about 1 mg/m$^2$, about 5 mg/m$^2$, about 10 mg/m$^2$, about 20 mg/m$^2$, about 30 mg/m$^2$, about 40 mg/m$^2$, about 50 mg/m$^2$, about 60 mg/m$^2$, about 70 mg/m$^2$, about 80 mg/m$^2$, about 90 mg/m$^2$, about 100 mg/m$^2$, about 110 mg/m$^2$, about 120 mg/m$^2$, about 130 mg/m$^2$, about 140 mg/m$^2$, about 150 mg/m$^2$, about 160 mg/m$^2$, about 170 mg/m$^2$, about 180 mg/m$^2$, about 190 mg/m$^2$, about 200 mg/m$^2$, about 210 mg/m$^2$, about 220 mg/m$^2$, about 230 mg/m$^2$, about 240 mg/m$^2$, about 250 mg/m$^2$, about 260 mg/m$^2$, about 270 mg/m$^2$, about 280 mg/m$^2$, about 290 mg/m$^2$, about 300 mg/m$^2$, about 310 mg/m$^2$, about 320 mg/m$^2$, about 330 mg/m$^2$, about 340 mg/m$^2$, about 350 mg/m$^2$, about 360 mg/m$^2$, about 370 mg/m$^2$, about 380 mg/m$^2$, about 390 mg/m$^2$, about 400 mg/m$^2$, about 410 mg/m$^2$, about 420 mg/m$^2$, about 430 mg/m$^2$, about 440 mg/m$^2$, about 450 mg/m$^2$, about 460 mg/m$^2$, about 470 mg/m$^2$, about 480 mg/m$^2$, about 490 mg/m$^2$, or about 500 mg/m$^2$.

In a particular embodiment, dacarbazine is administered intravenously.

In one embodiment, dacarbazine is administered intravenously to a subject at a dose ranging from about 150 mg/m$^2$ to about 250 mg/m$^2$.

In another embodiment, dacarbazine is administered intravenously to a subject once per day for five consecutive days at a dose ranging from about 150 mg/m$^2$ to about 250 mg/m$^2$.

In a specific embodiment, dacarbazine is administered intravenously to a subject once per day for five consecutive days at a dose ranging from about 150 mg/m$^2$ to about 250 mg/m$^2$ on days 1-5, then again intravenously once per day for five consecutive days on days 28-32 at a dose ranging from about 150 mg/m$^2$ to about 250 mg/m$^2$, then again intravenously once per day for five consecutive days on days 55-59 at a dose ranging from about 150 mg/m$^2$ to about 250 mg/m$^2$.

In one embodiment, dacarbazine is administered once intravenously to a subject at a dose ranging from about 150 mg/m$^2$ to about 250 mg/m$^2$.

In a specific embodiment, the other anticancer agent is doxorubicin.

Doxorubicin can be administered to a subject at dosages ranging from about 50 mg/m$^2$ (of a subject's body surface area) to about 100 mg/m$^2$ and from about 60 mg/m$^2$ to about 100 mg/m². In specific embodiments, the dosages of doxorubicin are about 10 mg/m², about 1 mg/m², about 5 mg/m², about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 110 mg/m², about 120 mg/m², about 130 mg/m², about 140 mg/m², about 150 mg/m², about 160 mg/m², about 170 mg/m², about 180 mg/m², about 190 mg/m², about 200 mg/m², about 210 mg/m², about 220 mg/m², about 230 mg/m², about 240 mg/m², about 250 mg/m², about 260 mg/m², about 270 mg/m², about 280 mg/m², about 290 mg/m², about 300 mg/m², about 310 mg/m², about 320 mg/m², about 330 mg/m², about 340 mg/m², about 350 mg/m², about 360 mg/m², about 370 mg/m², about 380 mg/m², about 390 mg/m², about 400 mg/m², about 410 mg/m², about 420 mg/m², about 430 mg/m², about 440 mg/m², about 450 mg/m², about 460 mg/m², about 470 mg/m², about 480 mg/m2, about 490 mg/m², or about 500 mg/m².

In a particular embodiment, doxorubicin is administered intravenously.

In one embodiment, doxorubicin is administered intravenously to a subject at a dose ranging from about 50 mg/m² to about 100 mg/m².

In another embodiment, doxorubicin is administered intravenously to a subject once per day for five consecutive days at a dose ranging from about 50 mg/m² to about 100 mg/m².

In a specific embodiment, doxorubicin is administered intravenously to a subject once per day for five consecutive days at a dose ranging from about 50 mg/m² to about 100 mg/m² on days 1-5, then again intravenously once per day for five consecutive days on days 28-32 at a dose ranging from about 50 mg/m² to about 100 mg/m², then again intravenously once per day for five consecutive days on days 55-59 at a dose ranging from about 50 mg/m² to about 100 mg/m².

In another embodiment, doxorubicin is administered once intravenously to a subject at a dose ranging from about 50 mg/m² to about 100 mg/m².

In one embodiment, the other anticancer agent is a Topoisomerase I inhibitor, such as etoposide, teniposide, topotecan, irinotecan, 9-aminocamptothecin, camptothecin, or crisnatol.

In a specific embodiment, the other anticancer agent is irinotecan.

Irinotecan can be administered to a subject at dosages ranging from about 50 mg/m² (of a subject's body surface area) to about 150 mg/m² and from about 75 mg/m² to about 150 mg/m². In specific embodiments, the dosages of irinotecan are about 10 mg/m², about 1 mg/m², about 5 mg/m², about 10 mg/m², about 20 mg/m², about 30 mg/m², about 40 mg/m², about 50 mg/m², about 60 mg/m², about 70 mg/m², about 80 mg/m², about 90 mg/m², about 100 mg/m², about 110 mg/m², about 120 mg/m², about 130 mg/m², about 140 mg/m², about 150 mg/m², about 160 mg/m², about 170 mg/m², about 180 mg/m², about 190 mg/m², about 200 mg/m², about 210 mg/m², about 220 mg/m², about 230 mg/m², about 240 mg/m², about 250 mg/m², about 260 mg/m², about 270 mg/m², about 280 mg/m², about 290 mg/m², about 300 mg/m², about 310 mg/m², about 320 mg/m², about 330 mg/m², about 340 mg/m², about 350 mg/m², about 360 mg/m², about 370 mg/m², about 380 mg/m², about 390 mg/m², about 400 mg/m², about 410 mg/m², about 420 mg/m², about 430 mg/m², about 440 mg/m², about 450 mg/m², about 460 mg/m², about 470 mg/m², about 480 mg/m², about 490 mg/m², or about 500 mg/m².

In a particular embodiment, irinotecan is administered intravenously.

In one embodiment, irinotecan is administered intravenously to a subject at a dose ranging from about 50 mg/m² to about 150 mg/m².

In another embodiment, irinotecan is administered intravenously to a subject once per day for five consecutive days at a dose ranging from about 50 mg/m² to about 150 mg/m².

In a specific embodiment, irinotecan is administered intravenously to a subject once per day for five consecutive days at a dose ranging from about 50 mg/m² to about 150 mg/m² on days 1-5, then again intravenously once per day for five consecutive days on days 28-32 at a dose ranging from about 50 mg/m² to about 150 mg/m², then again intravenously once per day for five consecutive days on days 55-59 at a dose ranging from about 50 mg/m² to about 150 mg/m².

In one embodiment, the other anticancer agent is O-6-benzylguanine.

In another embodiment, the other anticancer agent is O-6-benzylguanine and temozolomide.

In another embodiment, the other anticancer agent is O-6-benzylguanine and procarbazine.

In still another embodiment, the other anticancer agent is O-6-benzylguanine and dacarbazine.

5.5.1 Multi-therapy for Cancer

The N-Benzyl-Substituted Pyridyl Porphyrin Compounds can be administered to a subject that has undergone, is currently undergoing, or is about to undergo one or more additional anticancer treatments including, but not limited to, surgery, radiation therapy, or immunotherapy, such as administration of a cancer vaccine.

The present methods for treating cancer can further comprise administering surgery, radiation therapy, or immunotherapy.

In one embodiment, the anticancer treatment is immunotherapy.

In one embodiment, the immunotherapy is a cancer vaccine.

In one embodiment, the anticancer treatment is radiation therapy.

In another embodiment, the anticancer treatment is surgery.

In a specific embodiment, an N-Benzyl-Substituted Pyridyl Porphyrin Compound is administered concurrently with radiation therapy. In another specific embodiment, the additional anticancer treatment is administered prior or subsequent to the administration of the N-Benzyl-Substituted Pyridyl Porphyrin Compound, in one embodiment at least an hour, five hours, 12 hours, a day, a week, a month, or several months (e.g., up to three months), prior or subsequent to administration of the N-Benzyl-Substituted Pyridyl Porphyrin Compounds.

When the additional anticancer treatment is radiation therapy, any radiation therapy protocol can be used depending upon the type of cancer to be treated or prevented. For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered.

Additionally, the invention provides methods of treatment of cancer using the N-Benzyl-Substituted Pyridyl Porphyrin Compounds as an alternative to chemotherapy or radiation therapy where the chemotherapy or the radiation therapy results in negative side effects in the subject being treated. The subject being treated can, optionally, be treated with another anticancer treatment modality such as surgery, radiation therapy, or immunotherapy.

The N-Benzyl-Substituted Pyridyl Porphyrin Compounds can also be used in vitro or ex vivo, such as for the treatment of certain cancers, including, but not limited to leukemias and lymphomas, such treatment involving autologous stem cell transplants. This can involve a process in which the subject's autologous hematopoietic stem cells are harvested and purged of all cancer cells, the subject's remaining bone-marrow cell population is then eradicated via the administration of an N-Benzyl-Substituted Pyridyl Porphyrin Compound and/or radiation therapy, and the stem cell graft is infused back into the subject.

An N-Benzyl-Substituted Pyridyl Porphyrin Compound and the other therapeutic agent can act additively or, in one embodiment synergistically. In one embodiment an N-Benzyl-Substituted Pyridyl Porphyrin Compound is administered concurrently with another therapeutic agent. In one embodiment a composition comprising an effective amount of an N-Benzyl-Substituted Pyridyl Porphyrin Compound and an effective amount of another therapeutic agent can be administered. Alternatively, a composition comprising an effective amount of an N-Benzyl-Substituted Pyridyl Porphyrin Compound and a different composition comprising an effective amount of another therapeutic agent can be concurrently administered. In another embodiment, an effective amount of an N-Benzyl-Substituted Pyridyl Porphyrin Compound is administered prior or subsequent to administration of an effective amount of another therapeutic agent. In this embodiment the N-Benzyl-Substituted Pyridyl Porphyrin Compound is administered while the other therapeutic agent exerts its therapeutic effect, or the other therapeutic agent is administered while the N-Benzyl-Substituted Pyridyl Porphyrin Compound exerts its preventative or therapeutic effect for treating or preventing a Condition or for prolonging the half-life of an oxidation-prone compound.

A composition of the invention can be prepared by a method comprising admixing an N-Benzyl-Substituted Pyridyl Porphyrin Compound and a physiologically acceptable carrier or vehicle. Admixing can be accomplished using methods well known for admixing a compound and a physiologically acceptable carrier or vehicle. In one embodiment the N-Benzyl-Substituted Pyridyl Porphyrin Compound is present in the composition in an effective amount.

5.6 Kits

The invention encompasses kits that can simplify the administration of an N-Benzyl-Substituted Pyridyl Porphyrin Compound to a subject.

A typical kit of the invention comprises a unit dosage form of an N-Benzyl-Substituted Pyridyl Porphyrin Compound. In one embodiment the unit dosage form is within a container, which can be sterile, containing an effective amount of an N-Benzyl-Substituted Pyridyl Porphyrin Compound and a physiologically acceptable carrier or vehicle. The kit can further comprise a label or printed instructions instructing the use of the N-Benzyl-Substituted Pyridyl Porphyrin Compound to treat or prevent a Condition or to prolong the half-life of an oxidation-prone compound. The kit can also further comprise a unit dosage form of another therapeutic agent, for example, a container containing an effective amount of the other therapeutic agent. In one embodiment the kit comprises a container containing an effective amount of an N-Benzyl-Substituted Pyridyl Porphyrin Compound and an effective amount of another therapeutic agent. Examples of other therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not, of course, be construed as specifically limiting the invention described and claimed herein.

6. EXAMPLES

General Methods

Proton NMR spectra were obtained using a Varian 300 MHz spectrophotometer and chemical shift values ($\delta$) are reported in parts per million (ppm). TLC was performed using TLC plates precoated with silica gel 60 F-254. Intermediates and final compounds were characterized on the basis of $^1$H NMR and MS data, HPLC, and/or elemental analysis.

6.1 Example 1

Synthesis of Compound 1

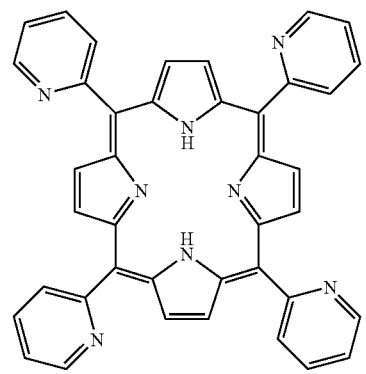

1

A 50 L three-neck reaction flask containing propionic acid (30 L) was equipped with two addition funnels and a reflux condenser. One addition funnel was charged with a solution of pyrrole (417 mL, 6.0 mol) in toluene (583 mL), and the second addition funnel was charged with a solution of 2-pyridinecarboxaldehyde (568 mL, 6.0 mol) in toluene (432 mL). The propionic acid was heated to reflux and then the contents of the addition funnels were added simultaneously at approximately equal rates-over 2 hours, with vigorous stirring to the refluxing propionic acid. The resultant dark red-brown reaction mixture was heated at reflux for 1 hour, then the heat source was removed and the reaction mixture was allowed to stir for about 18 hours at room temperature. The resultant black solution was filtered through #1 filter paper and concentrated in vacuo to provide a black oily residue. The black oily residue was diluted with toluene (5 L) and the resultant solution was stirred for 1 minute, then concentrated in vacuo. This dilution/concentration was repeated three times and the resultant black solid residue was diluted with ethyl acetate (5 L) and the resultant solution was stirred at room temperature for about 18 hours. The resultant solution was filtered through #1 filter paper, the collected solids were diluted with dichloromethane (2 L) and the resultant solution was purified using flash column chromatography on silica gel (10 kg) using dichloromethane: triethylamine (98:2 vol:vol) as eluent. The relevant fractions were combined and concentrated in vacuo, and the resultant black granular solid was diluted with 10% aqueous ammonium hydroxide (2 L), and the resultant suspension was stirred vigorously for 2 hours. The resultant suspension was filtered through #1 filter paper, and the collected black solids were washed with deionized water (4×1 L). The washed-solids were then suspended in ethyl acetate (2 L), and the resultant solution was stirred for 1 hour then filtered through #1 filter paper. The collected eggplant-colored granular solid was diluted with 1,2-dichloroethane (1 L) and the resultant solution was stirred for 2 hours, then filtered through #1 filter paper. The collected solids were washed with 1,2-dichloroethane (4×200 mL), then dried in vacuo overnight to provide Compound 1 as a brilliant deep metallic purple solid. Yield=64.26 g (7%). $R_f$=0.56 (silica, 9:1 dichloromethane: 7 N ammonia in methanol); $^1$H NMR (CDCl$_3$) δ 9.14 (d, J=3.9 Hz, 4H), 8.87 (S, 8H), 8.21 (d, J=7.5 Hz, 4H), 8.10 (dt, $J_1$=1.8 Hz, $J_2$=7.8 Hz, 4H), 7.71 (dd, $J_1$=5.1 Hz, $J_2$=7.5 Hz, 4H); $^{13}$C NMR (CDCl$_3$) δ 160.7, 148.8, 134.9, 132.2, 130.6, 122.6, 122.6, 119.0; mass spectrum ("MS") m/z=619 (M+H).

6.2 Example 2

Synthesis of Compound 2

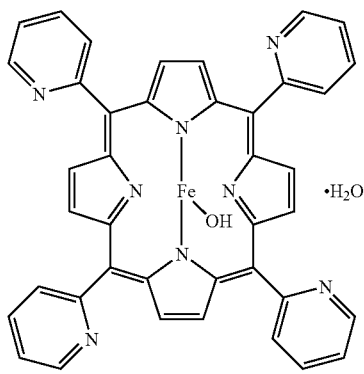

Ferric chloride (14.3 g; 88.89 mmol) was added to a suspension of Compound 1 (50.0 g, 80.39 mmol) in 1 N hydrochloric acid (245 mL, 3 eq.) and the resultant reaction mixture was heated to reflux and stirred for about 18 hours. The resultant dark brown reaction mixture was cooled to room temperature and basified using 5N sodium hydroxide (160 mL). The resultant precipitate was vacuum filtered through Whatman #50 filter paper and washed sequentially with deionized water (4×1.5 L) and diethyl ether (1.5 L). The resultant purple-black solid was subsequently dried in vacuo for 3 days at 100° C., then dissolved in dichloromethane (200 mL) and vacuum filtered through a one-inch pad of Celite. The Celite cake was washed with a solution of 9:1 (vol:vol) dichloromethane: methanol until the filtrate was nearly colorless. The filtrate was then concentrated in vacuo to provide Compound 2 as its monohydrate and as a purple-black iridescent powdered solid. Yield=25.74g (47%). MS m/z=672 (M+). Anal. Calc. for $C_{40}H_{27}FeN_8O_2$:67.91% C, 3.82% H, 7.90% Fe, 15.85% N, 4.53% O. Found: 67.84% C, 3.63% H, 7.70% Fe, 15.92% N.

6.3 Example 3

Synthesis of Compound 3

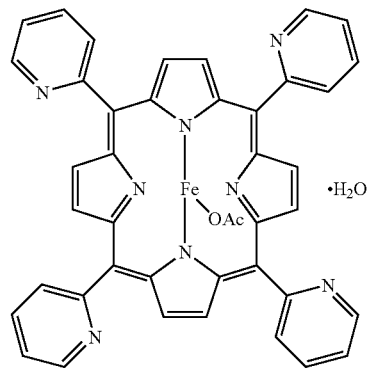

Compound 1 (200.0 g) was suspended in 3.2 L of acetic acid and 800 mL of deionized water, and 253.3 g (2.0 eq.) of ferrous ammonium sulfate hexahydrate were added. Air was bubbled slowly through the reaction mixture, which was then refluxed overnight. The hot reaction mixture was transferred to a rotary evaporator, and the solvent was removed in vacuo. The resultant solids were suspended with vigorous stirring for 3 hours in 4 L of 10% ammonium hydroxide, vacuum filtered through #50 paper, and washed four times with 1 L portions of deionized water. The slightly damp solids were stirred for 1 hour in 24 L ethanol and vacuum filtered through 500 g celite in a medium fritted funnel. The filtrate was transferred to the rotary evaporator and concentrated in vacuo. The resultant solids were dried under vacuum at 40° C. for 1 day to provide 164.0 g (68%) of Compound 3 as its monohydrate and as a deep-purple solid. MS m/z=672 (M$^+$).

6.4 Example 4

Synthesis of Compound 4

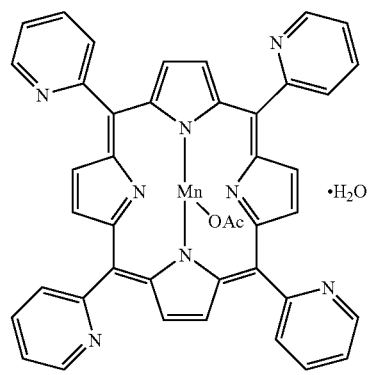

Compound 1 (1.00 g) was suspended in 10 mL of acetic acid, and 440 mg (1.01 eq.) of manganese (III) acetate dihydrate was added. The reaction mixture was refluxed overnight, and cooled to room temperature. The solvent was transferred to an evaporator flask and removed in vacuo. Ammonium hydroxide (30% aqueous, 20 mL) was added to the evaporator flask and subsequently removed in vacuo. The resultant solids were twice dissolved in methanol (20 mL), which was subsequently evaporated. The resultant black solid was dissolved in 50 mL of dichloromethane and vacuum filtered through a 3 cm thick bed of celite. The filtrate was concentrated in vacuo and the resultant solid was dried overnight to provide 1.28 g (95%) of Compound 4 as its monohydrate and as a metallic black solid. MS m/z=671 (M+).

6.5 Example 5

Synthesis of Compound 5

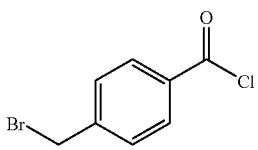

To 10 g of 4-bromomethylbenzoic acid in a 100 mL round bottom flask under a nitrogen atmosphere was added 25 mL of thionyl chloride at room temperature. The stirred suspension was refluxed for 4.5 h, and the solvent removed in vacuo. The resultant oil was twice dissolved in 50 mL toluene and the solvent removed in vacuo. Residual solvent was removed in vacuo to provide 10.92 g (100%) of Compound 5 as an off white solid.

6.6 Example 6

Synthesis of Compound 6

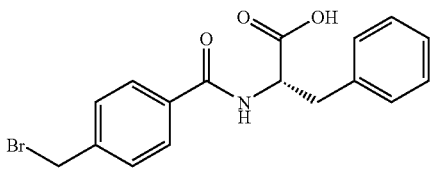

To a stirred suspension of 3.54 g L-phenylalanine in 2.74 mL (1.1 eq.), 2,6-lutidine and 21 mL N-methyl pyrrolidinone at 50° C. was added 5.00 g (1.0 eq.) of Compound 5. The suspension was stirred at 50° C. under a nitrogen atmosphere for 18 h, poured into 100 mL of rapidly stirred 1 N HCl, and extracted with 200 mL ethyl acetate. The resultant organic phase was washed with 100 mL each of 1 N HCl, water, and brine, dried over anhydrous MgSO₄, and concentrated in vacuo. The resultant gum was dissolved in 100 mL 5% acetic acid in dichloromethane and purified using flash chromatography on 300 g SiO₂. The column was eluted with 2 L each 5% acetic acid in dichloromethane, 1% acetic acid in 7:3 dichloromethane:ethyl acetate, and finally 1% acetic acid in ethyl acetate. 60 mL fractions were collected. Impurities eluted in 5% acetic acid in dichloromethane and Compound 6 eluted on addition of ethyl acetate. Compound 6-containing fractions were combined and the solvent was removed in vacuo to provide a yellow oil. The resultant oil was twice suspended in 100 mL volumes of toluene and concentrated in vacuo to remove acetic acid. The resultant solid was crystallized from ethyl acetate/toluene at −20° C. The crystals were vacuum filtered, washed with room temperature toluene, and dried in vacuo for 18 h. The filtrate was concentrated in vacuo and a second crop of crystals was collected. Crop 1 yielded 1.14 g of white crystals, crop 2 yielded 0.868 g (26% overall) of Compound 6.

6.7 Example 7

Synthesis of Compound 7

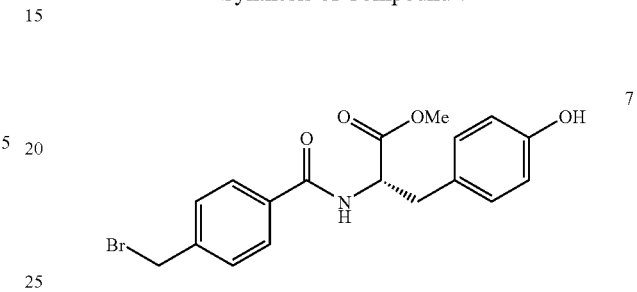

L-tyrosine methyl ester hydrochloride (4.96 g, 21.4 mmol) was suspended, with stirring, in 21 mL of dichloromethane and 5.2 mL (2.1 eq.) of 2,6-lutidine under nitrogen atmosphere. The suspension was cooled to 0° C. and Compound 5 (5.00 g, 21.4 mmol) was added. The suspension was allowed to warm to ambient temperature and stir for 18 h. The suspension was poured into 100 mL 1 N HCl and shaken in a separatory funnel. The resultant phases were separated and the aqueous phase twice extracted with 100 mL volumes of ethyl acetate. The combined dichloromethane and ethyl acetate organic phases were dried over anhydrous MgSO₄, filtered, and concentrated in vacuo to provide 7.22 g (86%) of Compound 7 as an off-white solid.

6.8 Example 8

Synthesis of Compound 8

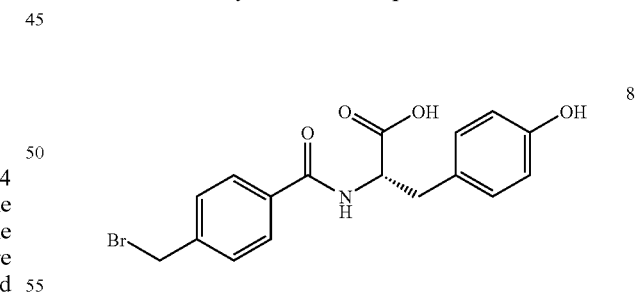

Compound 7 (7.20 g, 18.4 mmol) was suspended by stirring in 92 mL methanol. Sodium hydroxide (1 N aqueous, 55 mL) was added and the suspension stirred for 1.5 h, becoming a solution. Concentrated hydrochloric acid (4.6 mL, 3.0 eq.) was added and the methanol was removed in vacuo to provide a concentrated aqueous suspension of a red-white solid. The suspension was cooled on an ice bath for 15 min., then vacuum filtered. The resultant solids were washed with 100 mL 1 N HCl followed by 100 mL de-ionized water, then dried in vacuo at 40° C. for 18 h to yield 6.28 g (90%) of Compound 8.

6.9 Example 9

Synthesis of Compounds 9-16

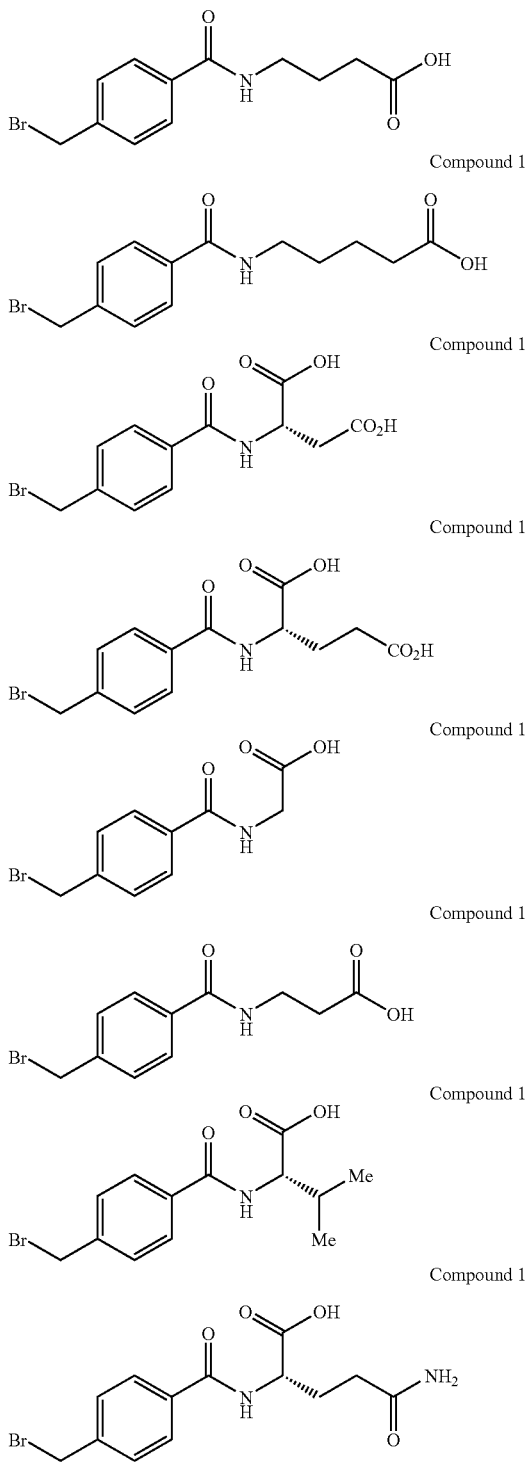

Compounds 9, 10, 11, 12, and 16 were synthesized following the procedure of Example 6, and Compounds 11, 13, 14, and 15 were synthesized following the procedure of Examples 7 and 8, by using γ-aminobutyric acid (Compound 9), 5-aminovaleric acid (Compound 10), L-aspartic acid methyl ester HCl (Compound 11), L-glutamic acid (Compound 12), glycine ethyl ester HCl (Compound 13), β-alanine methyl ester HCl (Compound 14), L-valine methyl ester HCl (Compound 15), and L-glutamine (Compound 16), respectively, in place of L-phenylalanine or L-tyrosine methyl ester HCl.

6.10 Example 10

Synthesis of Compound 17

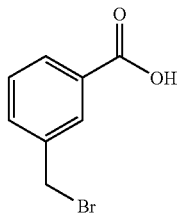

17

In a 1 L round bottom flask fitted with a reflux condenser, a stirred suspension of 10.00 g m-toluic acid and 14.37 g (1.1 eq.) N-bromosuccinimide in 735 mL chloroform was sparged for 0.5 h with nitrogen. The sparging was discontinued and the stirred suspension was irradiated under a nitrogen atmosphere using a 500 W quartz halogen lamp at 75% power, causing the solids to dissolve and the reaction to reflux. The red color of the reaction became clear after 1.25 h, and another 14.37 g of N-bromosuccinimide was added. The reaction mixture was stirred and irradiated under nitrogen atmosphere with a 500 W quartz halogen lamp at 75% power for another 1.5 h, at which time the solution was clear. The solvent volume was reduced in vacuo to about 100 mL, and then the solution was cooled to −20° C., forming crystals. The resultant suspension was vacuum filtered through a bed of dry silica, which was then eluted with 800 mL of chloroform. The chloroform filtrate volume was reduced in vacuo to about 100 mL, and then the chloroform was cooled to −20° C., forming crystals. The crystals were vacuum filtered and washed with 30 mL chloroformn and 50 mL hexanes, then dissolved in 250 mL chloroform and washed in a separatory funnel with 3×300 mL volumes of water, followed by one 300 mL volume of brine to remove traces of succinimide. The organic phase was dried over magnesium sulfate, vacuum filtered and concentrated in vacuo to provide 9.56 g (61%) of Compound 17 as a white crystalline power.

6.11 Example 11

Synthesis of Compound 18

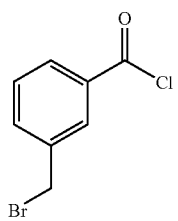

18

Compound 17 (10 g, 46.5 mmol) was suspended in 25 mL of $SOCl_2$. The suspension was heated to reflux under $N_2$ and the suspension became a clear pale yellow solution. After 4.5 h of reflux the reaction mixture was cooled and the excess reagent was removed in vacuo. Traces of thionyl chloride were removed by performing two iterations of diluting the residue with 50 mL toluene and removing the toluene in vacuo. The pale yellow oil was dried under vacuum to provide 10.8 g (quantitative yield) of Compound 18 as a pale yellow oil that solidified on standing.

6.12 Example 12

Synthesis of Compound 19

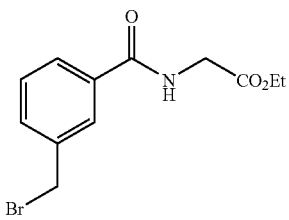

19

A solution of glycine ethyl ester HCl (2.98 g, 21.4 mmol) and 2,6-lutidine (5.71 mL, 2.3 eq) in 21 mL of dry methylene chloride was cooled in an ice/water bath under $N_2$. Compound 18 (5 g, 21.4 mmol) was added and the solution was allowed to warm to room temperature overnight with stirring. The reaction mixture was poured into 100 mL 1N HCl. The resultant aqueous solution was extracted with 2×150 mL ethyl acetate, and the combined organic phases were dried over $MgSO_4$, filtered and concentrated in vacuo to provide 5.9 g (92% yield) of Compound 19.

6.13 Example 13

Synthesis of Compounds 20-23 and 25

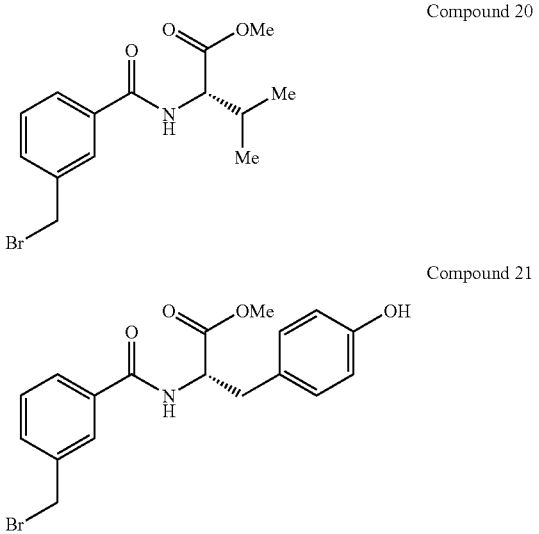

Compound 20

Compound 21

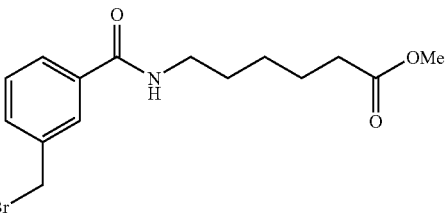

Compound 22

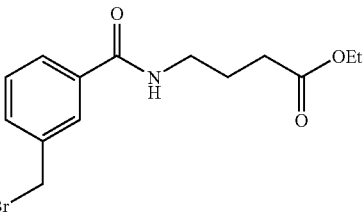

Compound 23

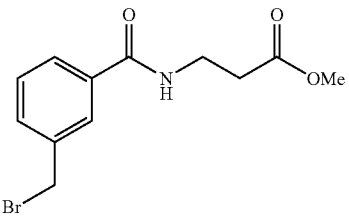

Compound 25

Following the procedure of Example 12, Compounds 20-23 were prepared by substituting glycine ethyl ester with L-valine methyl ester HCl, L-tyrosine methyl ester HCl, methyl 6-amino hexanoate HCl, and ethyl 4-amino butyrate HCl, respectively, with yields >90%.

Compound 25 was prepared following the procedure of Example 12 by substituting glycine ethyl ester HCl with β-alanine methyl ester.

6.14 Example 14

Synthesis of Compound 26

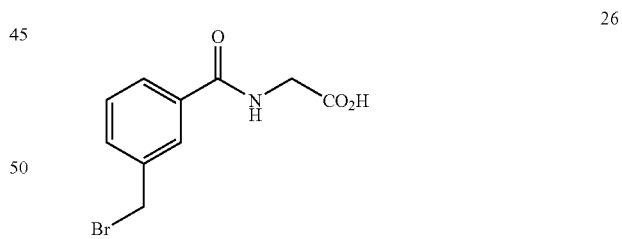

26

Compound 19 (5.9 g, 19.7 mmol) was dissolved in 90 mL EtOH, and 27.6 mL (1.4 eq) 1N NaOH (aq) was added in a steady stream at room temperature. After 10 min, the EtOH was removed in vacuo and the resultant solution was acidified with 1N HCl (aq). A heavy white precipitate was observed and the mixture was cooled in an ice/water bath to promote further solid formation. The solid was collected using vacuum filtration and dried in a vacuum oven at 40° C. overnight to provide 2.7 g of Compound 26. A second crop of solid was obtained by concentrating the filtrate to approximately half volume and cooling the solution in an ice/water bath. Upon vacuum filtration and drying, an additional 1.1 g of Compound 26 was obtained to provide a total yield of 71%.

6.15 Example 15

Synthesis of Compounds 27-30 and 32

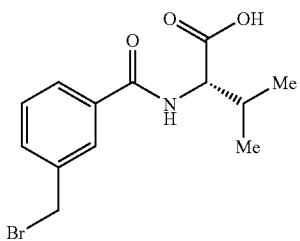
Compound 27

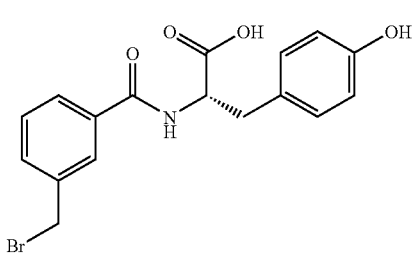
Compound 28

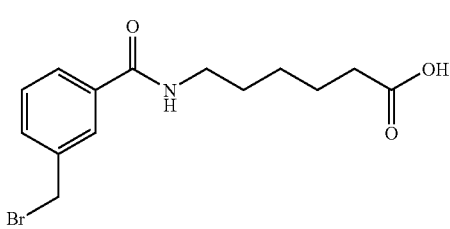
Compound 29

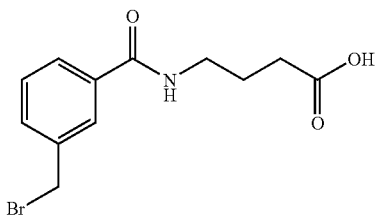
Compound 30

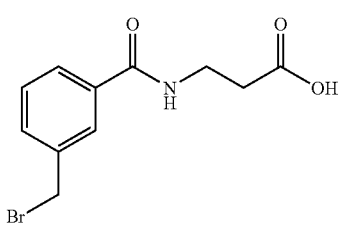
Compound 32

Following the procedure of Example 14, Compounds 27-30 and 32 were prepared from Compounds 20-23 and 25, respectively.

6.16 Example 16

Synthesis of Compound 33

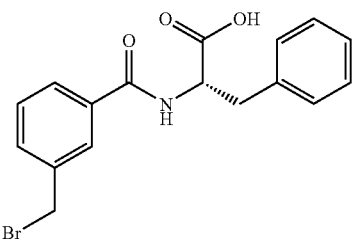
33

L-phenylalanine (3.54 g, 21.4 mmol), DMAP (0.5 g, 0.2 mmol) and 2,6-lutidine (2.73 mL, 1.1 eq) were suspended in 21 mL of anhydrous NMP and warmed to 50° C. Compound 18 was added at 50° C., providing a clear yellow solution. Stirring was continued overnight under $N_2$, which provided an orange reaction mixture having a white precipitate. The reaction mixture was poured into 100 mL 1N HCl(aq) and extracted with 250 mL ethyl acetate. The organic layer was washed with water and then brine. The organic layer was concentrated in vacuo to provide an orange oil. The oil was dissolved in 5% acetic acid/dichloromethane and loaded onto 300 g of silica gel packed in the same solvent. The column was eluted with 800 mL 5% acetic acid/methylene chloride, 200 mL 70:30 methylene chloride:ethyl acetate with 1% acetic acid, and 2×300 mL 1% acetic acid/ethyl acetate. The final two fractions contained Compound 33. Upon concentration and drying, 4.4 g (57% yield) Compound 33 was isolated as a white foam.

6.17 Example 17

Synthesis of Compound 34

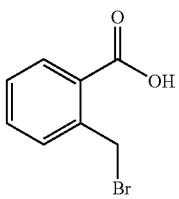
34

A stirred suspension of 10.00 g o-toluic acid and 19.56 g (1.5 eq.) N-bromosuccinimide in 735 mL chloroform was sparged for 0.5 h with nitrogen in a 1 L round bottom flask fitted with a reflux condenser. The sparging was discontinued and the stirred suspension was irradiated under a nitrogen atmosphere using a 500 W quartz halogen lamp at 75% power, causing the solids to dissolve and the reaction to reflux. The red color of the reaction disappeared after 1.5 h, and another 6.52 g (0.5 eq.) of N-bromosuccinimide was added. The reaction mixture was stirred and irradiated under nitrogen atmosphere using a 500 W quartz halogen lamp at 75% power for another 1.5 h, at which time the solution was clear. The solvent volume was reduced in vacuo to about 100 mL, and then cooled to −20° C. The resultant suspension was vacuum filtered through a 1 cm bed of dry silica in a 150 mL fritted funnel. The silica was eluted with 2.5 L of chloroform. The chloroform filtrate was reduced in vacuo to about 1 L and washed in a separatory funnel with 3×1 L volumes of water followed by one 1 L volume of brine to remove traces of succinimide, then dried over magnesium sulfate and vacuum filtered. The chloroform was concentrated in vacuo to 250 mL at reflux at 1 atmosphere and cooled at −20° C. for 3 days. The resultant crystals were vacuum filtered and washed with 30 mL chloroform followed by 50 mL hexanes, then placed in a vacuum oven at room temperature and full dynamic vacuum overnight. This provided 8.48 g (54%) of Compound 34 as a white crystalline power.

6.18 Example 18

Synthesis of Compound 35

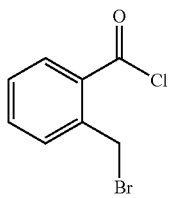

Following the procedure of Example 11, Compound 34 was converted to its corresponding acid chloride, Compound 35.

6.19 Example 19

Synthesis of Compound 36

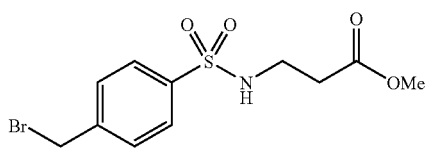

β-Alanine methyl ester HCl salt (1.79 g, 12.8 mmol) was suspended, with stirring, in 13 mL of dichloromethane and 3.1 mL (2.1 eq.) of 2,6-lutidine under nitrogen atmosphere. 4-bromomethylbenzenesulfonyl chloride (3.45 g, 1.0 eq.) was added. The suspension was stirred for 18 h, poured into 100 mL 1 N HCl, and extracted twice with 50 mL volumes of chloroform. The organic phases were dried over anhydrous MgSO$_4$, filtered, and the solvent removed in vacuo to provide 3.74 g (87%) of Compound 36 as a clear oil.

6.20 Example 20

Synthesis of Compound 37

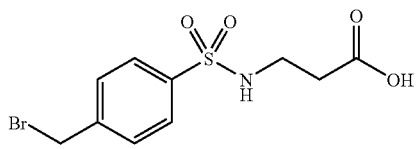

Compound 36 (3.66 g, 10.9 mmol) was dissolved by stirring in 54 mL methanol. Sodium hydroxide (1 N aqueous, 33 mL, 3 eq.) was added and the resultant suspension was stirred for 45 min. Hydrochloric acid (1 N aqueous, 40 mL) was added and the methanol was removed in vacuo to provide a concentrated aqueous suspension of a white solid. The suspension was cooled on an ice bath for 15 min., then vacuum filtered. The resultant solids were washed with 100 mL de-ionized water, then dried in vacuo at 40° C. for 18 h to yield 2.61 g (74%) of Compound 37.

6.21 Example 21

Synthesis of Compounds 38-39

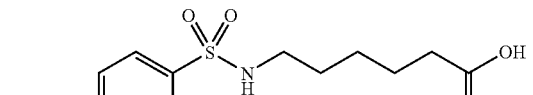

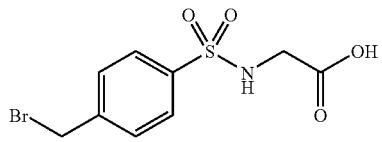

Compounds 38-39 were synthesized following the procedure of Examples 19-20 by substituting β-alanine methyl ester HCl salt with methyl 6-aminohexanoate and glycine ethyl ester HCl, respectively.

6.22 Example 22

Synthesis of Compound 40

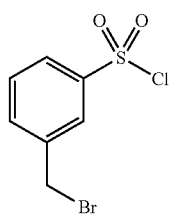

A 1 L round bottom flask was charged with 860 mL benzene, 24.50 g (128.5 mmol) m-toluenesulfonyl chloride, and 25.16 g (1.1 eq.) of N-bromo succinimide. The reaction was stirred under nitrogen and irradiated with a 500-watt quartz halogen lamp set at 60% of total power, which heated the reaction to reflux. After 6 h, additional N-bromo succinimide (4.57 g, 0.2 eq.) was added and the reaction mixture was irradiated at reflux for a further 6.5 h. Irradiation was discontinued and the reaction mixture was cooled on an ice bath for 1 h, causing a copious precipitate to form. The precipitate was vacuum filtered and washed with 100 mL toluene. The filtrate was washed three times with 600 mL volumes of water, followed by 600 mL of brine, and dried over 30 g anhydrous MgSO$_4$ and 23 g SiO$_2$. The resultant slurry was then vacuum filtered through a 2 cm thick bed of dry SiO$_2$ in a 150 mL medium fritted funnel. The filtered solids were washed in the funnel with 200 mL toluene, and the filtrate was concentrated in vacuo to provide 35.8 g of Compound 40 as a brown oil with white crystals. This was used in subsequent synthesis without further purification.

6.23 Example 23

Synthesis of Compound 41

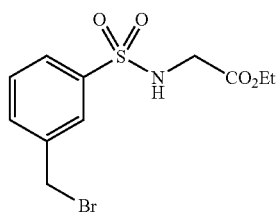

A suspension of glycine ethyl ester HCl (1.55 g, 11.1 mmol) and 2,6-lutidine (2.96 mL, 2.3 eq) in 12 mL methylene chloride was cooled in an ice/water bath. 3 Compound 40 (5 g, 11.1 mmol ~60% pure) was added to the reaction mixture, and the resultant dark brown solution was stirred and allowed to warm to room temperature overnight. TLC showed the presence of starting material, and an additional 0.75 g (5.37 mmol) of glycine ethyl ester HCl was added. The reaction was stirred for an additional 2 h. The reaction mixture was poured into 50 mL 1N HCl, and the resultant organic layer was washed with water and brine. Concentration of the organic layer in vacuo provided 5.6 g of a brown/orange oil. The oil was purified on 160 g silica. Less polar impurities were eluted with methylene chloride and Compound 41 was eluted with ethyl acetate. Concentration of the fractions containing Compound 41 provided 3.46 g of a dark brown oil. Its $^1$H NMR showed Compound 41 as well as ~25% of the di-bromo amide impurity. The mixture was used in subsequent reactions without further purification.

6.24 Example 24

Synthesis of Compound 42

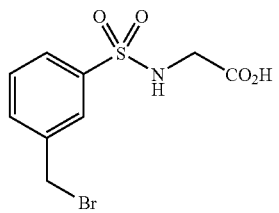

42

Compound 41 (1.67 g, 4.96 mmol) was dissolved in 25 mL ethanol and 7.5 mL (1.5 eq) 1N NaOH(aq) was added in a steady stream. After stirring at room temperature overnight, an additional 3 mL 1N NaOH (aq) was added. Stirring continued for 2 h. The reaction mixture was concentrated in vacuo to remove ethanol, and the resultant aqueous solution was washed with 50 mL EtOAc. The resultant aqueous layer was acidified with 1N HCl (aq) and concentrated. The resultant concentrate was extracted into ethyl acetate, and the organic phases were washed with brine. The organic layers were concentrated in vacuo to provide a brown oil, which was triturated with toluene to provide a tan solid (0.903 g). The tan solid contained Compound 42 as well as ~25% of a di-bromo impurity. The mixture was used in subsequent reactions without further purification.

6.25 Example 25

Synthesis of Compound 133

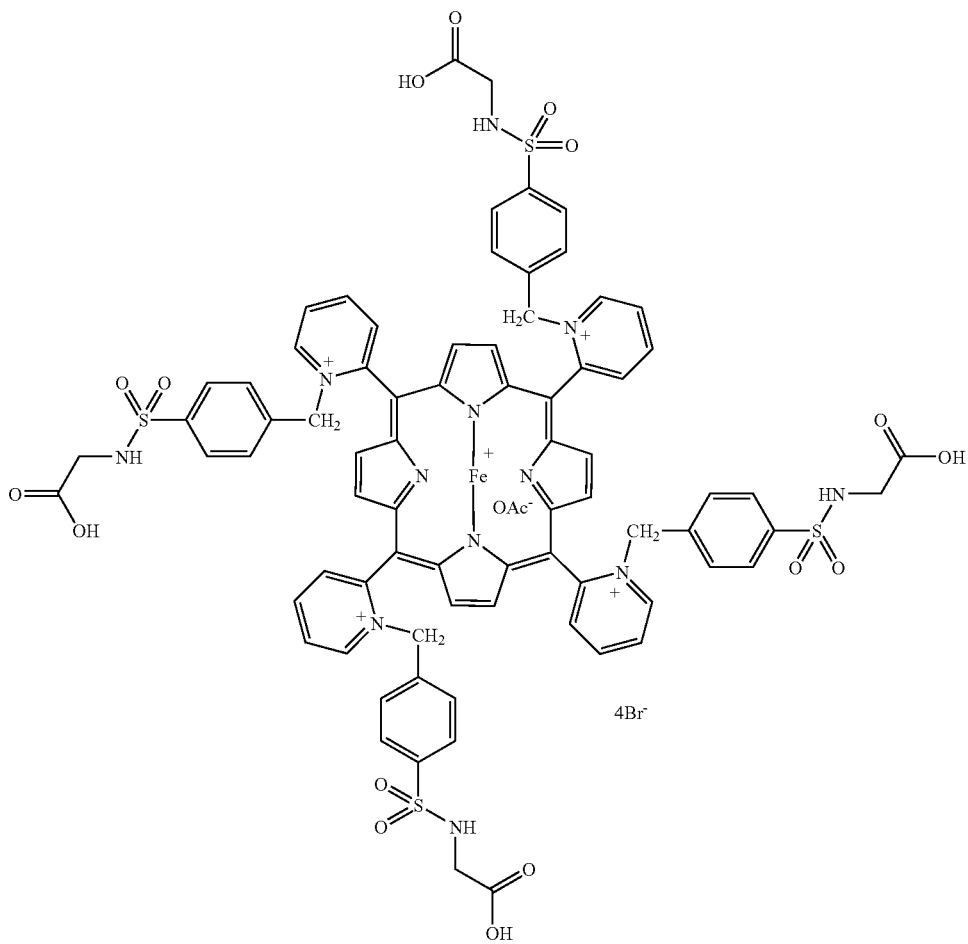

Compound 133

Compound 3 monohydrate (0.200 g, 0.267 mmol), Compound 39 (1.72 g, 20 eq.), and N-methyl pyrrolidinone (2 mL) were combined and stirred at 120° C. under nitrogen for 6 hrs. The reaction mixture was cooled to room temperature and 50 mL dichloromethane was added. The reaction mixture was stirred overnight at room temperature under nitrogen and then vacuum filtered through a 1 cm bed of celite in a 30 mL medium fritted funnel. The filtered solids were washed with 100 mL chloroform and the top layer of celite containing black adsorbed material was transferred to a 150 mL beaker. Chloroform (100 mL) was added to the beaker. The resultant suspension was stirred at reflux for 15 minutes, then vacuum filtered hot through a medium ftitted funnel. The filtered solids were returned to the beaker and the extraction was repeated. The filtered solids were then eluted in the fritted funnel with methanol until the filtrate and celite were nearly colorless. Combined filtrate was concentrated on a rotary evaporator and residual solvent was removed in vacuo for 18 hrs. The resultant black solid was dissolved in 50 mL of 4:1 water:methanol and purified via chromatography using 9.5 g of MCI-gel divinylbenzene polymeric resin packed in water in a 1 cm diameter column. The column was eluted with 200 mL each 4:1 water:methanol, 3:2 water:methanol, and 2:3 water:methanol. 30 mL fractions were collected and analyzed using HPLC. Fractions containing compounds of similar retention time were pooled together and analyzed using mass spectroscopy. The pooled fractions contained Compound 133. Fractions containing Compound 133 can be further purified using preparative HPLC to generate and isolate Compound 148 and its individual isomers, following the procedure of Example 26.2.

6.26 Example 26

6.26.1 Synthesis of Compound 107

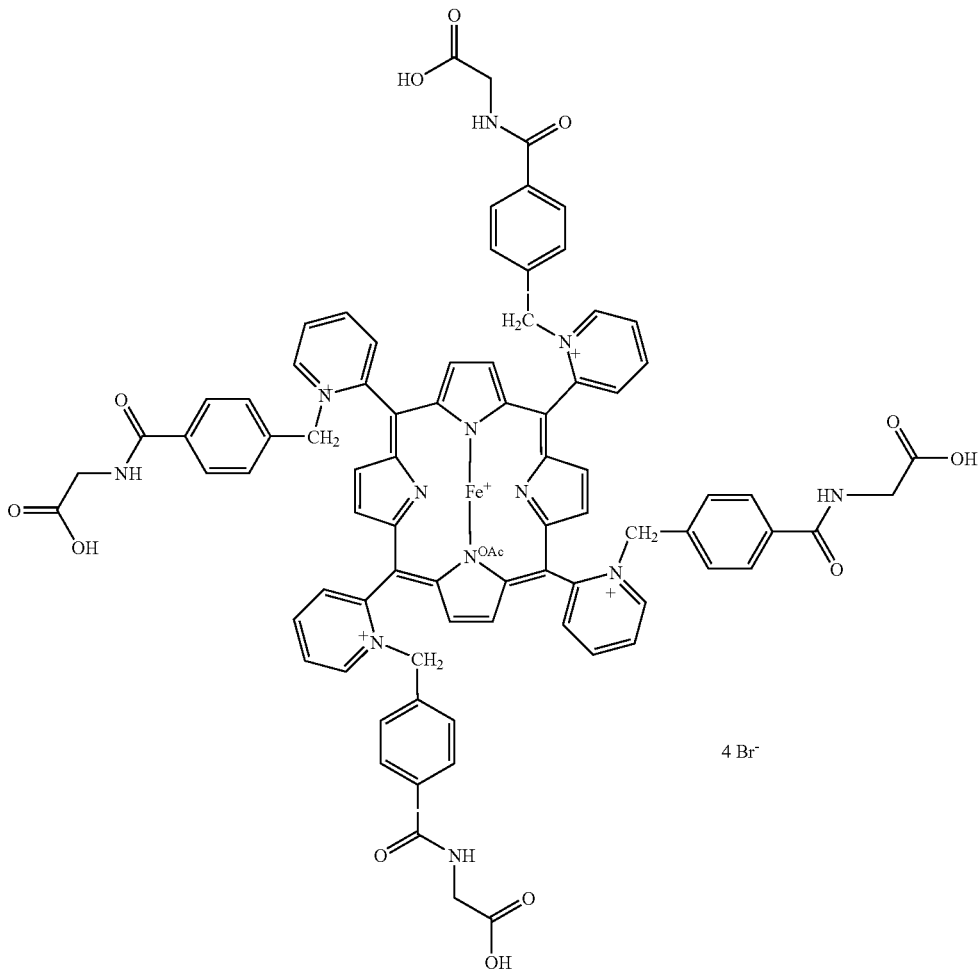

Compound 107

4 Br⁻

Compound 3 monohydrate (0.200 g, 0.267 mmol), Compound 13 (1.45 g, 20 eq.), and N- methyl pyrrolidinone (2 mL) were combined and stirred at 120° C. under nitrogen for 6.5 h. The reaction mixture was cooled to room temperature and 40 mL dichloromethane was added. The reaction mixture was stirred overnight at room temperature under nitrogen and then vacuum filtered through a 1 cm bed of celite in a 30 mL medium flitted funnel. The filtered solids were washed with 100 mL dichloromethane and the top layer of celite containing black adsorbed material was transferred to a 150 mL beaker. Dichloromethane (30 mL) was added to the beaker. The resultant suspension stirred at reflux for 15 minutes, then vacuum filtered hot through a medium fritted funnel. The filtered solids were returned to the beaker and the extraction was repeated. The filtered solids were then eluted in the fritted funnel with methanol until the filtrate and celite were nearly colorless. Combined filtrate was concentrated on the rotary evaporator and residual solvent removed in vacuo for 18 h. The resultant black solid was dissolved in 50 mL of deionized water and chromatographed on 9.5 g of MCI- gel divinylbenzene polymeric resin packed in water in a 1 cm diameter column. The column was eluted with 300 mL of water, then 200 mL each of 4:1 water:methanol, 3:2 water:methanol, and 2:3 water:methanol. 30 mL fractions were collected and analyzed by HPLC. Fractions containing compounds of similar retention time were pooled together and analyzed by mass spectroscopy. The solvent was removed in vacuo to give 264 mg of a black solid as a mixture of isomers. The pooled fractions contained Compound 107. The fractions containing Compound 107 were further purified by preparative HPLC.

6.26.2 Purification of Compound 107 Using Semi-preparative HPLC and Formation of Compound 122 by Anion Exchange The column dimensions were 250 mm×21.2 mm (diameter) and was packed by the manufacturer.

The column was equilibrated before injection by using 100% water with 0.1% trifluoroacetic acid (vol./vol.) at a flow rate of 20 mL/min for a minimum period of 30 minutes.

The filtered solution was injected (using 10 mL injection loop size) into the chromatograph, and the chromatographic separation was carried out using a two-component system of water with 0.1% (vol./vol.) trifluoroacetic acid ("solvent 1") and methanol with 0.1% (vol./vol.) trifluoroacetic acid ("Solvent 2") under the following gradient conditions:

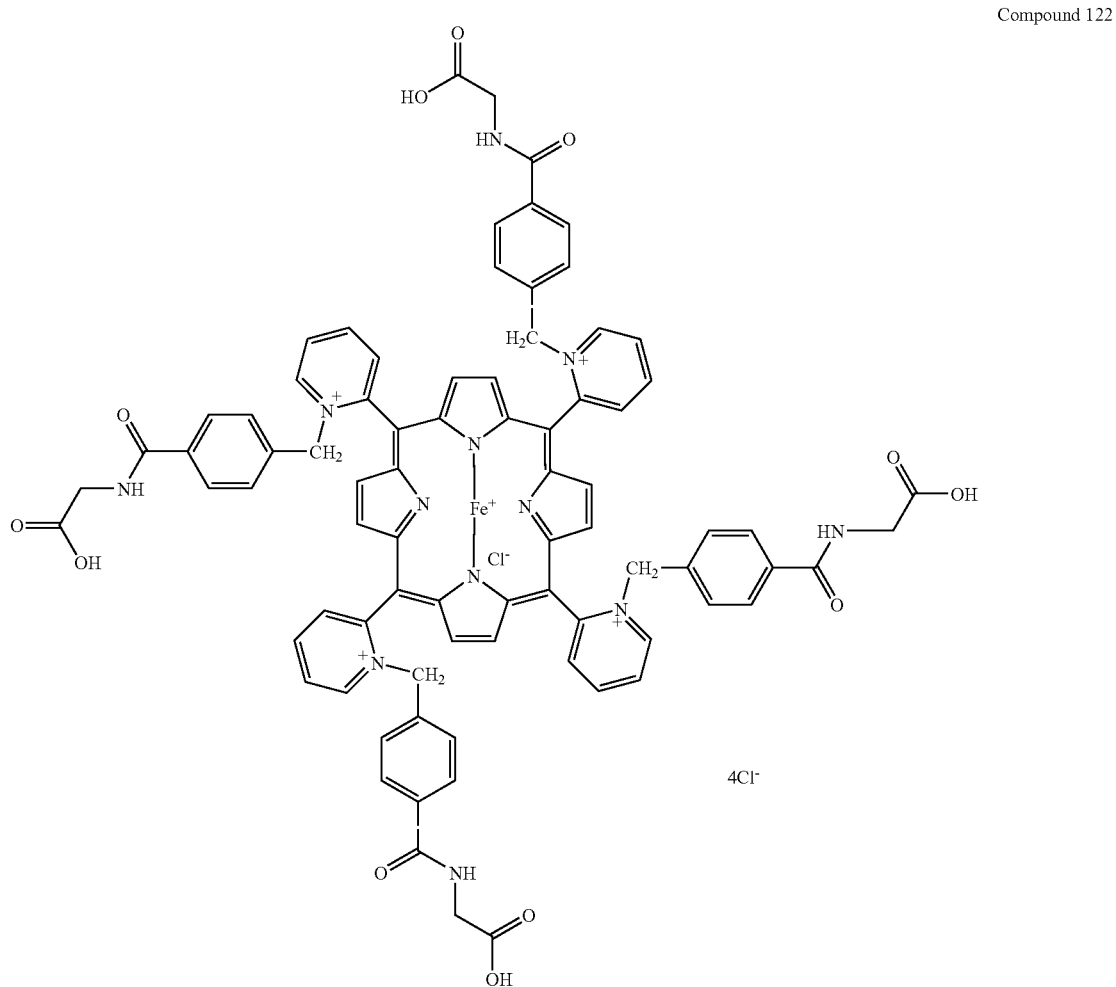

Compound 122

6.26.2.1 Semi-preparative Chromatography of Compound 107 Crude Mixture 245 milligrams of compound Compound 107 prepared according to the methods described in section 6.26.1 was dissolved in 7.5 mL of water having 0.1% trifluoroacetic acid (vol./vol.) and mixed for at least 30 minutes. The resultant solution was filtered through a 0.22 μm nylon membrane syringe filter and the final injection solution volume was ~8 mL. A Phenomenex, Synergi, POLAR-RP, 10 μm particle size, 80A pore size semi-preparative scale column was used.

| Time (min:sec) | Solvent 1 | Solvent 2 | Flow Rate |
|---|---|---|---|
| 0:00 (Inject) | 100% | 0% | 10 mL/min |
| 9:00 | 100% | 0% | 10 mL/min |
| 10:00 | 80% | 20% | 10 mL/min |
| 53:00 | 80% | 20% | 10 mL/min |
| 54:00 | 70% | 30% | 10 mL/min |
| 75:00 | 70% | 30% | 10 mL/min |
| 80:00 | 10% | 90% | 10 mL/min |
| 98:00 | 10% | 90% | 10 mL/min |
| 100:00 | 100% | 0% | 10 mL/min |

Fraction collection began at about 20 minutes (run time from point of injection) where the first major compound (i.e. >10% threshold@254 nm) began to elute. The set fraction volume taken was 10 mL (60 seconds). Fraction collection ended at about 100 minutes (where the threshold is <10%@254 nm) and the last of the components finished eluting from the column.

Individual fractions were analyzed on HPLC. Fractions shown to contain individual components of greater than or equal to 90 area %@254 nm were combined into their respective pools as follows ("RT" means retention time):

| Pool 1, Fraction 5: | RT 2.6 min. peak | Total vol. = 10 mL |
|---|---|---|
| Pool 2, Fractions 14-15: | RT 3.2 min. peak | Total vol. = 20 mL |
| Pool 3, Fractions 30-35: | RT 5.6 min. peak | Total vol. = 60 mL |

All of the above pools were concentrated in vacuo to dry residues using a rotary evaporator to provide residues.

6.26.2.2 Resin Treatment to Provide Compound 122

Each residue of Pool 1, Pool 2, and Pool 3 were diluted with water to a final volume of 3 mL each. Each resultant solution was then each stirred with DOWEX Marathon 11 (Chloride form) strongly-basic anion-exchange resin (1 mL of aqueous solution of settled resin for each respective sample) for a period of 4 hours at room temperature.

After resin treatment, each pool solution was filtered through a 0.22 μm nylon membrane syringe filter. The remaining resin was washed with 2 mL of methanol for each of the samples and each of those methanol washes were filtered through a 0.22 μm nylon membrane syringe filter and added to their respective solutions.

6.26.2.3 Drying and Final Products, Compound 122 Isomers 1-3

Each of the solutions was concentrated in vacuo and dried under high vacuum for a minimum period of 70 hours at room temperature to provide:

Compound 122, isomer 1 as a solid (6 milligrams, 93 area % purity@254 nm by HPLC) in Penta-Chloride form; RT of 2.6 min peak;

Compound 122, isomer 2 as a solid (5 milligrams, 91 area % purity@254 nm by HPLC) in Penta-Chloride form; RT of 3.2 min peak;

Compound 122, isomer 3 as a solid (15 milligrams, 93 area % purity@254 nm by HPLC) in Penta-Chloride form; RT of 5.6 min peak.

6.27 Example 27

Compounds 101, 102, 106, 108, 109, 112 and 113, of Formula (IA), were synthesized according to the procedure set forth in the Example section 6.25 and Example section 6.26.1, where Compound 9, Compound 10, Compound 6, Compound 8, Compound 11, Compound 14, and Compound 15, respectively, were used in place of Compound 39.

Compounds 103-105, 110, 111, and 114, of Formula (IA), were synthesized according to the procedure set forth in the Example section 6.25 and Example section 6.26.1, where Compound 4 was used in place of Compound 3, and where Compound 11, Compound 10, Compound 12, Compound 13, Compound 14, and Compound 16, respectively, were used in place of Compound 39.

Formula (IA):

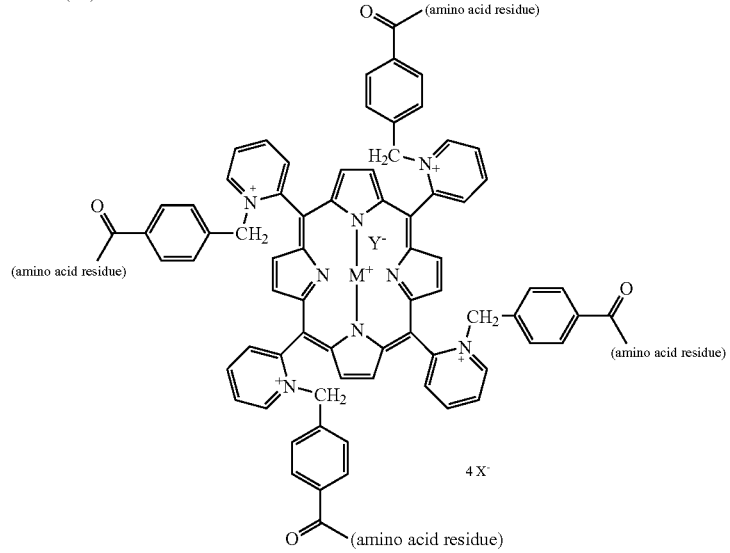

| Compound No. | Amino Acid of the Amino Acid Residue | M | Y⁻ | X⁻ |
|---|---|---|---|---|
| Compound 101 | γ-aminobutyric acid | Fe | OAc⁻ | Br⁻ |
| Compound 102 | 5-aminovaleric acid | Fe | OAc⁻ | Br⁻ |
| Compound 103 | L-aspartic acid | Mn | OAc⁻ | Br⁻ |
| Compound 104 | 5-aminovaleric acid | Mn | OAc⁻ | Br⁻ |
| Compound 105 | L-glutamic acid | Mn | OAc⁻ | Br⁻ |
| Compound 106 | L-phenylalanine | Fe | OAc⁻ | Br⁻ |
| Compound 108 | L-tyrosine | Fe | OAc⁻ | Br⁻ |
| Compound 109 | L-aspartic acid | Fe | OAc⁻ | Br⁻ |

Formula (IA):

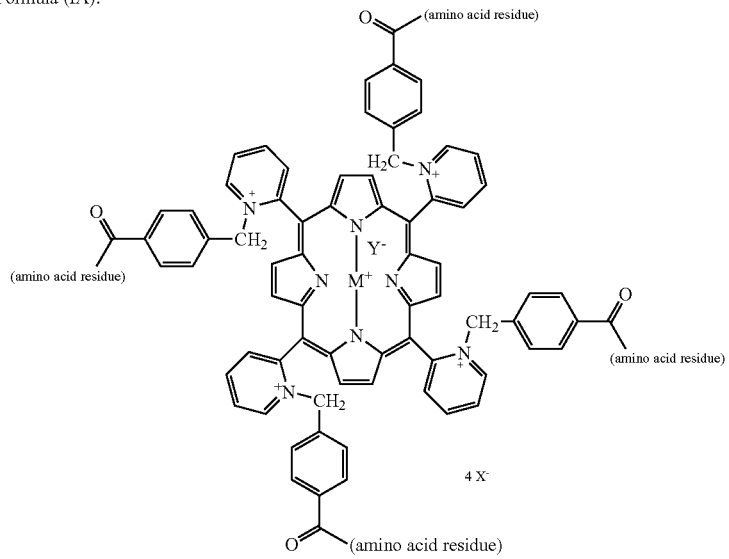

| Compound No. | Amino Acid of the Amino Acid Residue | M | Y⁻ | X⁻ |
|---|---|---|---|---|
| Compound 110 | glycine | Mn | OAc⁻ | Br⁻ |
| Compound 111 | β-alanine | Mn | OAc⁻ | Br⁻ |
| Compound 112 | β-alanine | Fe | OAc⁻ | Br⁻ |
| Compound 113 | L-valine | Fe | OAc⁻ | Br⁻ |
| Compound 114 | L-glutamine | Mn | OAc⁻ | Br⁻ |

Compounds 131 and 132 of Formula (IB) were synthesized according to the procedure set forth in the Example section 6.25 and Example section 6.26.1, where Compounds 38 and 37, respectively, were used in place of Compound 39.

Formula (IB):

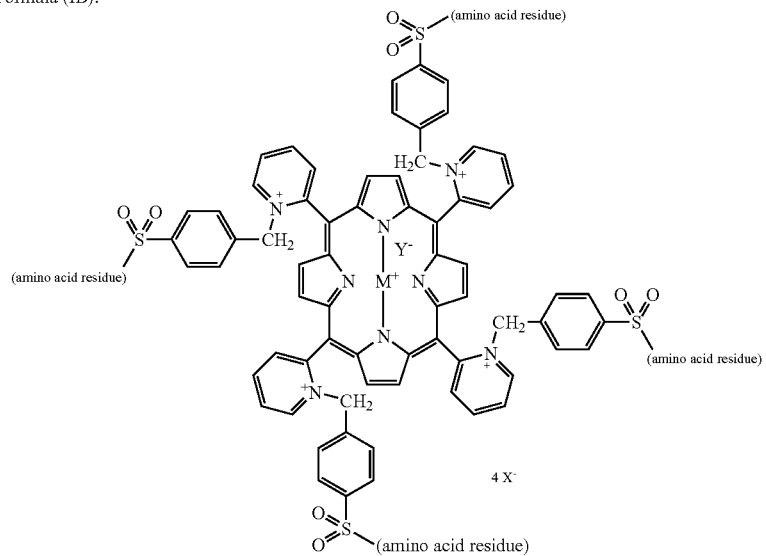

| Compound No. | Amino Acid of the Amino Acid Residue | M | Y⁻ | X⁻ |
|---|---|---|---|---|
| Compound 131 | 6-aminohexanoic acid | Fe | OAc⁻ | Br⁻ |
| Compound 132 | β-alanine | Fe | OAc⁻ | Br⁻ |

Compounds 161-163 and 165-167 of Formula (IIA) were synthesized according to the procedure set forth in the Example section 6.25 and Example section 6.26.1, where Compound 27, Compound 28, Compound 33, Compound 26, Compound 29, and Compound 30, respectively, were used in place of Compound 39.

Compound 164 of Formula (IIA) was synthesized according to the procedure set forth in the example section 6.25 and Example section 6.26.1, where Compound 4 was used in place of Compound 3, and Compound 32 was used in place of Compound 39.

ratio" is calculated by dividing the number of surviving mice by the total number of irradiated mice.

Pre-irradiation Treatment of Animals

Balb/c mice are divided into two groups of about ten mice each: a control group and a treatment group. Each mouse in the control group is subcutaneously administered 0.1 mL saline two hours prior to irradiation, followed by repeated subcutaneous administrations of 0.1 mL saline every 12 hours afterward. Each mouse in the treatment group is subcutaneously administered a 2 mg/kg dose of an N-Benzyl-Substi- Formula (IIA):

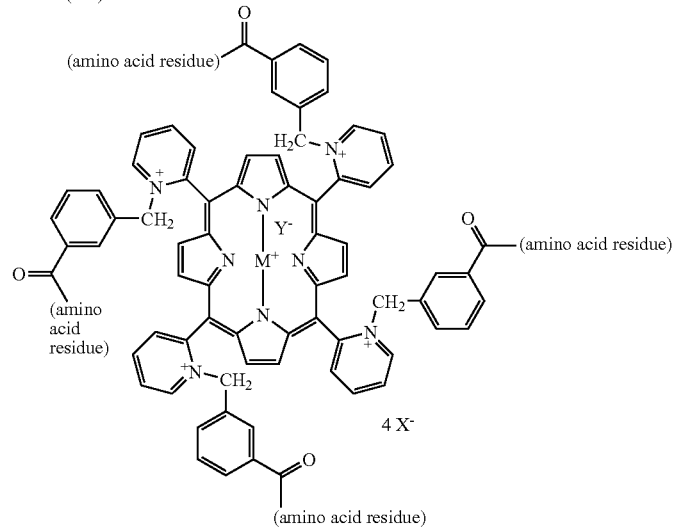

| Compound No. | Amino Acid of the Amino Acid Residue | M | Y⁻ | X⁻ |
|---|---|---|---|---|
| Compound 161 | L-valine | Fe | OAc⁻ | Br⁻ |
| Compound 162 | L-tyrosine | Fe | OAc⁻ | Br⁻ |
| Compound 163 | L-phenylalanine | Fe | OAc⁻ | Br⁻ |
| Compound 164 | β-alanine | Mn | OAc⁻ | Br⁻ |
| Compound 165 | glycine | Fe | OAc⁻ | Br⁻ |
| Compound 166 | 6-aminohexanoic acid | Fe | OAc⁻ | Br⁻ |
| Compound 167 | γ-aminobutyric acid | Fe | OAc⁻ | Br⁻ |

6.28 Example 28

In Vivo Efficacy of an N-Benzyl-Substituted Pyridyl Porphyrin Compound Against Radiation-Induced Death Materials and Methods Balb/c mice used in the following experiments are 8 weeks old, either male or female, and have an average body weight of 24 g. An N-Benzyl-Substituted Pyridyl Porphyrin Compound is administered to the treated animals subcutaneously as a solution in 0.9% normal saline with each individual dose administered in a total solution volume of 0.1 mL. Both treated and control mice are exposed to a 6 Gy dose of ionizing radiation, delivered via a Gammacell 3000 Elan Irradiator (MDS Nordion, Ontario, Canada). To administer the radiation dose, a mouse is placed in a beaker in the irradiation chamber with the sealed radiation source for approximately one minute to deliver a dose of 6 Gy. The animals' "survival tuted Pyridyl Porphyrin Compound (in 0.1 mL saline) two hours prior to irradiation, followed by repeated subcutaneous administrations of a 2 mg/kg dose of an N-Benzyl-Substituted Pyridyl Porphyrin Compound (in 0.1 mL saline) every 12 hours afterward. Dosing is continued in each animal in both the control and treatment groups until the death of all of the mice in the control group.

Post-irradiation Treatment of Mice

Balb/c mice are divided into two groups of about ten mice each: a control group and a treatment group: Each mouse in the control group is subcutaneously administered 0.1 mL saline ten minutes after irradition, followed by repeated subcutaneous administrations of 0.1 mL saline every 12 hours afterward. Each mouse in the treatment group is subcutaneously administered a 2 mg/kg dose of an N-Benzyl-Substituted Pyridyl Porphyrin Compound (in 0.1 mL saline) ten minutes after irradiation, followed by repeated subcutaneous administrations of a 2 mg/kg dose of the same N-Benzyl-Substituted Pyridyl Porphyrin Compound (in 0.1 mL saline) every 12 hours afterward. Dosing is continued in each animal in both the control and treatment groups until the death of all of the mice in the control group.

Post-irradiation Treatment of Mice

Balb/c mice are divided into two groups of about ten mice each; a control group and a treatment group. Each mouse in the control group is subcutaneously administered 0.1 mL saline ten minutes after irradition, followed by repeated subcutaneous administrations of 0.1 mL saline every 12 hours afterward. Each mouse in the treatment group is subcutaneously administered a 10 mg/kg dose of an N-Benzyl-Substituted Pyridyl Porphyrin Compound (in 0.1 mL saline) ten minutes after irradiation, followed by repeated subcutaneous administrations of a 10 mg/kg dose of the same N-Benzyl-Substituted Pyridyl Porphyrin Compound (in 0.1 mL saline) every 12 hours afterward. Dosing is continued in each animal in both the control and treatment groups until the death of all of the mice in the control group.

6.29 Effect of an N-Benzyl-Substituted Pyridyl Porphyrin Compound on Various Diseases Effect on Oxidant or Free-radical Damage A549 human epithelial cells and RAW murine macrophages were grown and cultured, then treated with oxidants or free radicals in the presence or absence of varying concentrations of an N-Benzyl-Substituted Pyridyl Porphyrin according to the method of C. Szabo et al., *Mol Med.*, 2002 October; 8(10):571-80. Illustrative N-Benzyl-Substituted Pyridyl Porphyrin Compounds dose-dependently protected against the suppression of cell viability (FIGS. 1-12) in murine RAW cells. 10 or 100 µM of each illustrative N-Benzyl-Substituted Pyridyl Porphyrin Compound was used, as indicated in FIG. 1-12.

These data indicate that Compounds 163, 165, 162, 161, 166, 167, 134, 105, 103, 122 isomer 1, 122 isomer 2, 122 isomer 3, 101, 102, 108, 112, 113, 133, 132, 131, 107, and 165 are useful for treating or preventing a Condition, and for prolonging the half-life of an oxidation-prone compound.

Effect on Myocardial Infarction in Rats

Rats are subjected to myocardial infarction by occlusion and reperfusion of the left anterior descending coronary artery as previously described in C. Y. Xiao et al., *J Pharmacol Exp Ther.*, 2004 August;310(2):498-504. An N-Benzyl-Substituted Pyridyl Porphyrin Compound is administered at doses of 1, 3, or 6 mg/kg i.v., 5 minutes prior to reperfusion.

Effect on Hemorrhagic Shock in Rats

Rats are subjected to 2 hours of hemorrhage, followed by resuscitation as previously described in O. V. Evgenov et al., *Crit Care Med.*, 2003 October;31(10):2429-36. An N-Benzyl-Substituted Pyridyl Porphyrin Compound is administered at a dose of 6 mg/kg i.v., 5 minutes prior to resuscitation. Rats are bled to reach mean BP of 40 mm Hg. This mean BP is maintained for 2 hours, followed by resuscitation with saline at a volume of 2× the shed blood volume. Rats are then observed for 3 hours, and the survival time is recorded. An N-Benzyl-Substituted Pyridyl Porphyrin Compound (6 mg/kg) is administered intravenously before the start of resuscitation. Left intraventricular systolic pressure (LVSP), dP/dt, –dP/dt are monitored continuously for 20 minutes from 40 minutes after resuscitation. An N-Benzyl-Substituted Pyridyl Porphyrin Compound (6 mg/kg) is administered intravenously before the start of resuscitation. Blood is taken 1 hour after resuscitation. An N-Benzyl-Substituted Pyridyl Porphyrin Compound (6 mg/kg) is administered intravenously before the start of resuscitation. Blood is taken at 1 hour after resuscitation. An N-Benzyl-Substituted Pyridyl Porphyrin Compound (6 mg/kg) is administered intravenously before the start of resuscitation.

Effect on Heart Failure in Mice

Mice are subjected to heart failure induced by aortic banding as previously described in C. Y. Xiao et al., *J Pharmacol Exp Ther.*, 2005 March;312(3):891-8. An N-Benzyl-Substituted Pyridyl Porphyrin Compound is administered at a dose of 3 mg/kg/day orally.

Effect on Rejection of Hearts During Heterotopic Heart Transplantation

Rats are subjected to heterotopic heart transplantation as described previously in H. Jiang et al., *Transplantation*, 2002 Jun. 15;73(11):1808-17. An N-Benzyl-Substituted Pyridyl Porphyrin Compound is administered at a dose of 10 mg/kg/day orally.

Effect on Vascular Injury

Rats are subjected to balloon-induced vascular injury of the carotid artery as previously described in C. Zhang et al., *Am J Physiol Heart Circ Physiol.*, 2004 August;287(2):H659-66.

Effect on Diabetes Mellitus

Mice are subjected to multiple low dose streptozocin diabetes as previously described in J. G. Mableyet al., *Br J Pharmacol.*, 2001 July;133(6):909-19.

The present invention is not to be limited in scope by the specific embodiments disclosed in the examples, which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All references cited herein are incorporated by reference in their entirety.

I claim:

1. A compound having the Formula (A):

Formula (A):

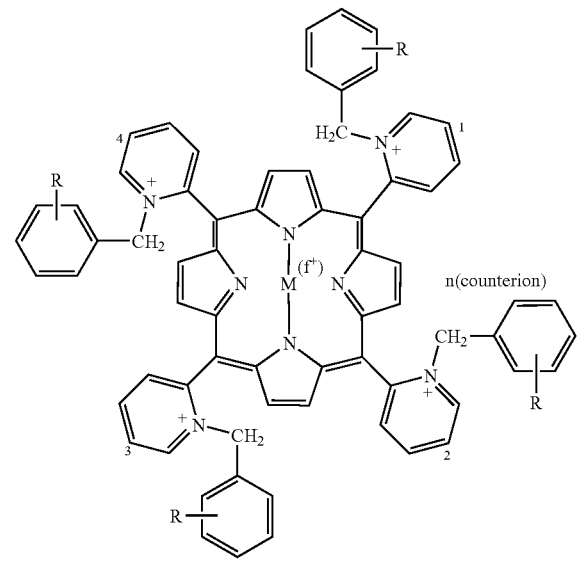

wherein:
M is Fe or Mn;
f is 0 or 1;

each R is independently —C(O)(amino acid residue) or —SO$_2$(amino acid residue); and n is the number of counterions sufficient to balance the charges of the compound of Formula (A).

2. The compound of claim 1, having the Formula (I):

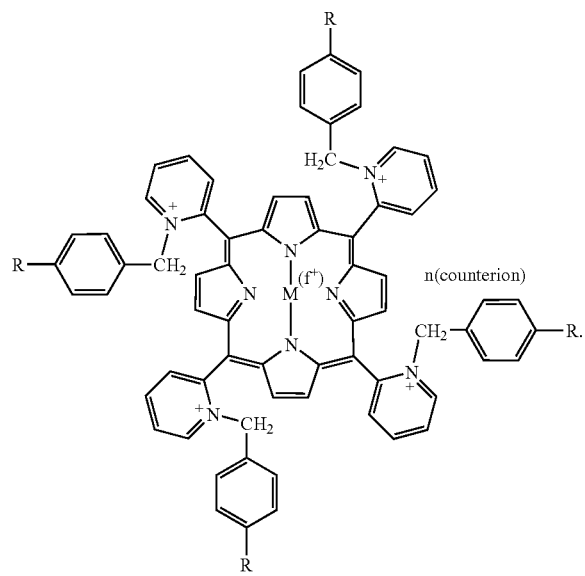

3. The compound of claim 1, having the Formula (II):

4. The compound of claim 1, having the Formula (III):

5. The compound of claim 1, wherein f is 1, each counterion is monovalent, n is 5, and each amino acid residue is uncharged.

6. The compound of claim 1, wherein f is 1, the counterion is monovalent, n is 1, and each amino acid residue has a —CO$_2^-$ moiety as its only charged group.

7. The compound of claim 1, wherein M is Fe.

8. The compound of claim 1, wherein M is Mn.

9. The compound of claim 1, wherein f is 0.

10. The compound of claim 1, wherein f is 1.

11. The compound of claim 1, wherein each counterion is Cl$^-$ or Br$^-$.

12. The compound of claim 1, wherein a counterion forms a bond with M.

13. The compound of claim 1, wherein each counterion is independently F$^-$, Cl$^-$, Br$^-$, I$^-$, HO$^-$, or CH$_3$C(O)O$^-$.

14. The compound of claim 1, wherein each R is —C(O)(amino acid residue).

15. The compound of claim 1, wherein each R is —SO$_2$(amino acid residue).

16. The compound of claim 1, wherein n is 1.

17. The compound of claim 1, wherein n is 5.

18. The compound of claim 6, wherein f is 1, and each counterion is Cl$^-$.

19. The compound of claim 17, wherein each R is —C(O)(amino acid residue).

20. The compound of claim 17, wherein each R is —SO$_2$(amino acid residue).

21. The compound of claim 1, wherein the amino acid of the amino acid residue is β-alanine, γ-aminobutyric acid, 6-aminohexanoic acid, 5-aminovaleric acid, L-aspartic acid, L-glutamine, L-glutamic acid, glycine, L-phenylalanine, L-tyrosine, or L-valine.

22. A composition comprising an effective amount of the compound of claim 1 and a physiologically acceptable carrier or vehicle.

* * * * *